United States Patent
Pfahl et al.

(10) Patent No.: US 7,071,218 B2
(45) Date of Patent: Jul. 4, 2006

(54) N-SUBSTITUTED HETEROCYCLES FOR THE TREATMENT OF HYPERCHOLESTEREMIA, DYSLIPIDEMIA AND OTHER METABOLIC DISORDERS; CANCER, AND OTHER DISEASES

(75) Inventors: Magnus Pfahl, Solana Beach, CA (US); Catherine Tachdjian, San Diego, CA (US); Lyle W. Spruce, Chula Vista, CA (US); Hussien A. Al-Shamma, Encinitas, CA (US); Mohamed Boudjelal, San Diego, CA (US); Andrea N. Fanjul, San Diego, CA (US); Torsten R. Wiemann, Encinitas, CA (US); David P. M. Pleynet, San Diego, CA (US)

(73) Assignees: Incyte San Diego Incorporated, San Diego, CA (US); Ortho McNeil Pharmaceutical Inc., Rariton, NJ (US)

( * ) Notice: Subject to any disclaimer, the term of this patent is extended or adjusted under 35 U.S.C. 154(b) by 172 days.

(21) Appl. No.: 10/298,024

(22) Filed: Nov. 15, 2002

(65) Prior Publication Data

US 2003/0144329 A1  Jul. 31, 2003

Related U.S. Application Data

(60) Provisional application No. 60/362,732, filed on Mar. 8, 2002, provisional application No. 60/362,702, filed on Mar. 8, 2002, provisional application No. 60/334,794, filed on Nov. 15, 2001.

(51) Int. Cl.
  *A61K 31/426* (2006.01)
  *C07D 277/36* (2006.01)
  *C07D 401/02* (2006.01)
(52) U.S. Cl. .................. 514/342; 514/369; 548/183; 548/226; 548/317.1
(58) Field of Classification Search ............. 546/269.7; 548/183; 514/342, 369
  See application file for complete search history.

(56) References Cited

U.S. PATENT DOCUMENTS

| 4,051,842 A | 10/1977 | Hazel et al. |
|---|---|---|
| 4,140,122 A | 2/1979 | Kühl et al. |
| 4,383,529 A | 5/1983 | Webster |
| 4,668,506 A | 5/1987 | Bawa |
| 4,713,244 A | 12/1987 | Bawa et al. |
| 4,788,063 A | 11/1988 | Fisher et al. |
| 4,931,279 A | 6/1990 | Bawa et al. |
| 4,971,996 A | 11/1990 | Shiraishi et al. |
| 5,223,522 A | 6/1993 | Clark et al. |
| 5,330,998 A | 7/1994 | Clark et al. |
| 5,512,689 A | 4/1996 | Quallich |
| 5,523,314 A | 6/1996 | Bue-Valleskey et al. |
| 5,650,444 A | 7/1997 | Cagiano et al. |
| 5,691,376 A | 11/1997 | Cagiano et al. |
| 5,780,676 A | 7/1998 | Boehm et al. |
| 6,127,415 A | 10/2000 | Pfahl et al. |
| 6,262,044 B1 | 7/2001 | Møller et al. |
| 6,515,003 B1 | 2/2003 | Pfahl et al. |
| 6,765,013 B1 | 7/2004 | Pfahl et al. |
| 6,908,939 B1 * | 6/2005 | Bernardon et al. ......... 514/369 |
| 6,927,228 B1 | 8/2005 | Bernardon et al. |
| 2005/0165072 A1 * | 7/2005 | Ayer et al. ................. 514/369 |

FOREIGN PATENT DOCUMENTS

| EP | 0 212 617 | 3/1987 |
|---|---|---|
| EP | 0 304 493 | 3/1989 |
| EP | 0 343 643 | 11/1989 |
| EP | 1 048 659 | 11/2000 |
| EP | 1 142 885 | 10/2001 |
| JP | 55 038359 | 3/1980 |
| WO | WO 93/21146 | 10/1993 |
| WO | WO 94/12880 | 6/1994 |
| WO | WO 97/00249 | 1/1997 |
| WO | WO 97/03682 | 2/1997 |
| WO | WO 97/27191 | 7/1997 |
| WO | WO 99/09965 | 3/1999 |
| WO | WO 99/24415 | 5/1999 |
| WO | WO 99/58127 | 11/1999 |
| WO | WO 00/10573 | 3/2000 |
| WO | WO 00/18748 | 4/2000 |
| WO | WO 00/32598 | 6/2000 |
| WO | WO 00/63196 | 10/2000 |

(Continued)

OTHER PUBLICATIONS

Acheson et al., "Two Hypothetical Metabolites of Proguanil," *J. Chem. Soc.*, 10:4727-4731 (1956).

(Continued)

*Primary Examiner*—Fiona T. Powers
(74) *Attorney, Agent, or Firm*—Needle & Rosenberg, P.C.

(57) ABSTRACT

The present invention relates to certain compounds of Formula (I) which can be useful in the treatment of diseases, such as, cancer, metabolic disorders, Type 2 Diabetes, dyslipidemia and/or hyperchloesterolemia:

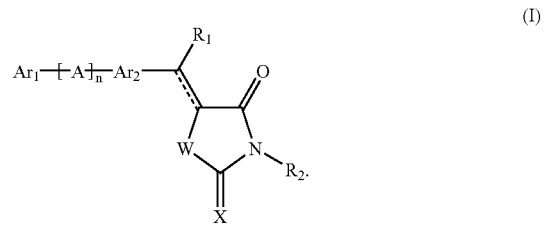

45 Claims, 13 Drawing Sheets

FOREIGN PATENT DOCUMENTS

| WO | WO 00/066167 | 11/2000 |
|----|--------------|---------|
| WO | WO 01/16122  | 3/2001  |
| WO | WO 01/16123  | 3/2001  |
| WO | WO 01/36402  | 5/2001  |
| WO | WO 02/12210  | 2/2002  |
| WO | WO 02/071827 | 9/2002  |
| WO | WO 02/072099 | 9/2002  |
| WO | WO 02/072543 | 9/2002  |
| WO | WO 02/080935 | 10/2002 |

OTHER PUBLICATIONS

Alley et al., "Feasibility of Drug Screening with Panels of Human Tumor Cell Lines Using a Microculture Tetrazolium Assay," *Cancer Res.* 48:589-601 (1988).

Aman et al., "The Inositol Phosphatase SHIP Inhibits Akt/PKB Activation in B Cells" *J. Biol. Chem.*, 273(51)33922-33928 (1998).

Amin et al., "Nitric Oxide Synthase and Cyclooxygenases: Distribution, Regulation, and Intervention in Arthritis," *Nitric pin. Rheumatol*, 11(3):202-209 (1999).

Arakawa et al., "Novel Benzoxazole 2,4-Thiazolidinediones as Potent Hypoglycemic Agents. Synthesis and Structure-Acitivity Relationships," *Chem. Pharm. Bull.*, 42(12) 1984-1993 (1997).

Aranyos et al., "Novel Electron-Rich Bulky Phospine Ligands Facilitate the Palladium-Catalyzed Preparation of Diaryl Ethers," *J. Am. Chem. Soc.* 121:4369-4378 (1999).

Baraldi et al., "Exhaled Nitric Oxide Concentrations During Treatment of Wheezing Exacerbation in Infants and Young Children," *Am. J. Respir. Crit. Care Med.*, 159 (4 Pt. 1):1284-1288 (1999).

Beilstein Registry No. 29-30, 1975, Compound Registry No. 1120438.

Beilstein Registry No. 52, 1978, Compund Registry No. 4939128.

Bellacosa et al., "Structure, express and chromosomal mapping of c-*akt*: relationship to v-*akt* and its implications," *Oncongene*, 8:745-754 (1993).

Black, "Simple Synthesis of 1-Azaadamantan-4-one," *Synthesis*, 829-830 (1981).

Blakemore et al., "A Stereoselective Synthesis of trans-1,2-Disubstituted Alkenes Based on the Condensation of Aldehydes with Metallated 1-Phenyl-1H-tetrazol-5-yl Sulfones," *Synlett*, 26-28 (1977).

Blondet et al., "Convenient Synthesis of 6-Methyl, 8-Methyl and 6,8-Dimethyl Derivatives of 5-Hydroxy-1,2,3,4-Tetrahydro-2-Quinolinone," *Organic Preparation and Procedures Int.*, 25(2):223-228 (1993).

Bradisher et al., "Aromatic Cyclodehydration XXIV. Cyclization of Derivatives of (2-biphenylly)pyruvic Acid," J. Org. Chem., 15(2) 374-376 (1950).

Bredt et al., "Isolation of Nitric Oxide Synthetase, a Calmodulin-Requiring Enzyme," *Proc. Natl. Acad. Sci.* 87:682-685 (1990).

Brennan et al., "Inhibitory Effect of TNFα Antibodies on Synovial Cell Interleukin-1 Production in Rheumatoid Arthritis," *Lancet*, 2:244-247 (1989).

Brown et al., "Purine Analogues as Amplifiers of Phleomycin. V* Thioethers of Several Heterocyclic Systems with One or Two Rings," *Aust. J. Chem* 32: 2713-2726 (1979).

Bryant et al., "Host-Guest Complexation. 53. Functional Groups Preorganized in Hemispherands for Binding Alkali Metal and Ammonium Cations[1]," *J. Org. Chem.*, 55:4622-4634 (1990).

Cantello et al., "A Versatile Route to 2-Arylmethyl-1,2-oxadiazolidine-3,5-diones via Regiospecific Alkyl-ation of 1,2,4-Oxadiazolidine-3,5-dione," *Synlett*, 263-264 (1997).

Cantello et al., "The Synthesis of BRL 49653—A Novel and Potent Antihyperglycaemic Agent," *Bioorganic & Medicinal Chemistry Letters*, 4:1181-1184 (1994).

Caron et al., "Directed Ortho Metalation of Neopentyl Benzoates with LDA: Preparation of Arylboronic Acids," *J. Org. Chem.*, 63:2054-2055 (1998).

Cervantes et al., "Generation of oxindole-2-thiones (thiols) via dilithiated N-tert-Boc-anilines. Synthesis of a sulfur analog of MK886[1]," *Can. J. Chem.*, 73:336-342 (1995).

Chan et al., "New N- and O-Arylations with Phenyloboronic Acids and Curpric Acetate," *Tetrahedron Letters* 39:2933-2936 (1998).

Chang et al., "Transformation of Chicken Cells by the Gene Encoding the Catalytic Subunit of PI 3-Kinase," *Science*, 276:(5320)1848-1850 (1997).

Chang et al., "The Upjohn Colony of Kka$^y$ Mice: A Model for Obese Type II Diabetes," *Elsevier Science Publishers B.V., Biomedical Division, Diabetes*, pp. 466-470 (1986).

Charpentier et al., "Synthesis, Structure—Affinity Relationships, and Biological Activites of Ligands Binding to Retinoic Acid Receptor Subtypes," *J. Med. Chem.* 38:4993-5006 (1995).

Choi et al., "Similarity of Colorectal Cancer in Crohn's Disease and Ulcerative Colitis: Implications for Carcinogenesis and Prevention," Gut, 35:950-954 (1994).

Cobb et al., "N-(2-Benzoylphenyl)-L-tyrosine PPARγ Agonists. 3. Structure-Activity Relationship and Optimization of the N-Aryl Substituent," *J. Med. Chem.* 41:5055-5069 (1998).

Coleman "Diabetes-Obesity Syndromes in Mice," *Diabetes*, 31(1):1-6 (Apr. 1982).

D'Amico, "Derivatives of 2-Benzothiazolesulfenamides. I. Novel Method for Preparation of N-Substituted Benzothizaolesulfenamides," J. Org. Chem. 26:3436-3445 (1961).

Darses et al., "Palladium-Catalyzed Cross-Coupling Reactions of Arenediazonium Tetrafluoroborates with Aryl- and Alkenylboronic Acids," *Bull. Soc. Chem. Fr.*, 133:1095-1102 (1996).

Dawson et al., "Conformational Effects on Retinoid Receptor Selectivity. 2. Effects of Retinoid Bridging Group on Retinoid X Receptor Activity and Selectivity," *J. Med. Chemistry*, 38:3368-3383 (1995).

Dawson et al., "The Synthetic Chemistry of Retinoids," *Biology, Chemistry, and Medicine*, 2$^{nd}$ Edition, Raven Press, Ltd., New York (1994).

DeSimone et al., "Substituted 3-(2-Benzoxazyl)-benzimidazol-2-(1H)-ones: A New Class of GABA$_A$ Brain Receptor Ligands," Bioorganic & Medicinal Chemistry Letters 10:2723-2726 (2000).

Di Cristofano et al., "Pten and p27$^{KIP1}$ cooperate in prostate cancer tumor suppression in the mouse," *Nature Genetics*, 27:222-224 (2001).

Dryanska et al., "a-Hydroxybenzylation and Benzylidenation of the Methyl Group in 2-Methyl-1,3-benzoxazole and 2-Methyl-1,3-benzothiazole," *Synthesis*, 37-38 (1976).

Ebisawa et al., "Novel Thiazolidinedione Derivatives with Retinoid Synergistic Activity," *Biol. Pharma. Bull.*, 21(5):547-549 (1998).

Ejmocki et al., "Synthesis of 5-Mono-, Di- and Trichloromethylsuflfonylbenzimidazoleurea and Benzimidazolethiocarbarnate Derivatives," *Polish Journal of Chemistry*, 59:1279-1284 (1985).

Elnagdi et al., "Studies with Polyfunctionally Substituted Herteroaromatics: A New Route to Polyfunctionally Substituted Annelated Mercaptophthalazines," *Phosphorus, Sulfur and Silicon*, 82:195-205 (1993).

El-Sherbeny, "Synthesis of Certain Pyrimido[2,1-b]benzothiazole and Benzothiazolo[2,3-b]quinazoline Derivatives for in vitro Antitumor and Antiviral Activities," *Arzneim. Forsch./Drug Res.*, 50(II):848-853 (2000).

Evans et al., "Synthesis of Diaryl Ethers through the Copper-Promoted Arylation of Phenols with Arylboronic Acids. An Expedient Synthesis of Thyroxine," *Tetrahedron Letters* 39:2937-2940 (1998).

Farahat et al., "Cytokine Epression in Synovial Membranes of Patients with Rheumatoid Arthritis and Osteoarthritis," *Ann. Rheum. Dis.*, 52: 870-875 (1993).

Ferrell, "Tripping the Switch Fantastic: How A Protein Kinase Cascade Can Convert Graded Inputs into Switch-Like Outputs," *TIBS*, 21:460-466 (1996).

Firooznia et al., "Enantioselective Synthesis of 4-Substituted Phenylalanines By Cross-Coupling Reactions," *Tetrahedron Letters*, 40:213-216 (1999).

Förstermann et al., "Induced RAW 264.7 Macrophages Express Soluble and Particulate Nitric Oxide Synthase: Inhibition by Transforming Growth Factor-β," *Euro. J. Pharm.*, 225:161-165 (1992).

Fukuto et al., "Inhibition of Constitutive and Inducible Nitric Oxide Synthase: Potential Selective Inhibition," *Annu. Rev. Pharmacol. Toxicol.* 35:165-194 (1995).

Gahtan et al., "Inflammatory Pathogenesis in Alzheimer's Disease: Biological Mechanisms and Cognitive Sequetil," *Neurosci: Biobehav*, 23:615-633 (1999).

Garin et al., "Synthesis of Unsymmetrical Diheteroarylbenzenes: Benzoazole and Quinazoline Derivatives," *J. Heterocyclic Chem.*, 28:359-363 (1991).

Gilbert, "Perhaloketones XIX (1). Derivatives of Benzo-N-heterocycles," *J. Heterocyclic*, 6:483-490 (1969).

Glauser et al., "Pathogenesis and Potential Strategies for Prevention and Treatment of Septic Shock: An Update," *Clin. Infect Dis.* 18 (Suppl. 2):S205-216 (1994).

Gown, et al., "Human Atherosclerosis—II. Immunocytochemical Analysis of the Cellular Composition of Human Atherosclerotic Lesions," *Am. J. Pathol.*, 125(1):191-207 (1986).

Gray et al., "Practical Methylation of Aryl Halides by Suzuki-Miyaura Coupling," *Tetrahedron Letters*, 41:6237-6240 (2000).

Grivas et al., "Synthesis of Mutagenic Methyl- and Phenyhl-substituted 2-Amino-3H-imidazo[4,5-f]quinoxalines via 2,1,3,-Benzoselenadiazoles," *Acta Chemica Scandinavica*, 47:521-528 (1993).

Gudmundsson et al., "Synthesis and Antiviral Evaluation of Halongenated β-D- and -L-Erythrofuransylbenzimidazoles," *J. Med. Chem.*, 43:2464-2472 (2000).

Gupta et al., "Heterocyclic Systems Containing Bridgehead Nitrogen Atom: Part XXXVIII—Reaction of 6-Bromo-2-mercapto-4-methylbenz-imidazole with Chloroacetic Acid, α-Halogenoketones & 1,2-Dibromoethane," *Indian Journal of Chemistry*, 19B:1035-1037 (1980).

Haddach et al., "A New Method for the Synthesis of Ketones: The Palladium-Catalyzed Corss-Coupling of Acid Chlorides with Arylboronic Acids," *Tetrahedron Letters* 40:3109-3112 (1999).

Hansch et al., "The Vapor Phase Catalytic Synthesis of Thianaphthenes," *J. Am. Chem. Soc.*, 70:1561-1563 (1948).

Harris et al., "Localization of a Pioglitazone Response Element in the Adipocyte Fatty Acid-Binding Protein Gene," *Mol. Pharmacol.* 45:439-445 (1994).

Haviv et al., "3-[1-(2-Benzoxazolyl)hydrazino]propanenitrile Derivatives: Inhibitors of Immune Complex Induced Inflammation[1]," *J. Med. Chem.*, 31:1719-1728 (1988).

Hazelton et al., "2H-Benzimidazoles (Isobenzimidazoles). Part 10.[1,2] Synthesis of Polysubstituted o-Phenylenediamines and their Conversion into Heterocycles, Particularly 2-Substituted Benzimidazoles with Known or Potential Anthelminthic Activity," *Tetrahedron Letters,* 51(39):10771-10794 (1995).

Houpis et al., "Condensation of 2-Methylbenzoxazole with Aromatic Aldehydes Bearing Acidic Protons. A Convenient Coupling in the Synthesis of the HIV-Reverse Transcriptase Inhibitor L-696,229," *J. Org. Chem.*, 58:3176-3178 (1993).

Hudlicky, "Oxidations in Organic Chemistry," ACS Monograph 186:114-127 (1990).

Hudlicky, "Oxidations in Organic Chemistry," ACS Monograph 186:133-149 (1990).

Hultquist et al., "N-Heterocyclic Benzenesulfonamides," J. Am. Chem. Soc. 73:2558-2566 (1951) 2558.

Ibrahim et al., "Novel 2'-Substituted Amino-17-oxoestra-1(10),4-dieno[2,3-d]oxazole and Eastra-1,5(10)-dieno[4,3-d]oxazole Derivatives: Synthesis and in vitro Anabolic-Catabolic Activities (1)," J. Heterocyclic Chem. 19:761-768 (1982).

Indolese, "Suzuki-Type Coupling of Chloroarenes with Arylboronic Acids Catalysed by Nickel Complexes," *Tetrahedron Letters*, 38:3513-3516 (1997).

Ishiyama et al., "Palladium(0)-Catalyzed Cross-Coupling Reaction of Alkoxydiboron with Haloarenes: A Direct Procedure for Arylboronic Esters," *J. Org. Chem.*, 60:7508-7510 (1995).

Ishiyama et al., "Palladium-Catalyzed Carbonylative Cross-Coupling Reaction of Arylboronic Acids with Aryl Electrophiles: Synthesis of Biaryl Ketones," *J. Org. Chem.*, 63:4726-4731 (1998).

Ishiyama et al., "Synthesis of Arylboronates via the Palladium(0)-Catalyzed Cross-Coupling Reaction of Tetra(alkoxo)diborons with Aryl Triflates," *Tetrahedron Letters*, 38:3447-3450 (1997).

Ishiyama et al. "Synthesis of Unsymmetrical Biaryl Ketones via Palladium-Catalyzed Carbonylative Cross-Coupling Reaction of Arylboronic Acids with Iodoarenes," *Tetrahedron Letters*, 34:7595-7598 (1993).

Ito et al., "Heterocyclic Syntheses by Diaminocarbene-Palladium(II) Complex Intermediates," *Journal of Organometallic Chemistry*, 131:121-311 (1977).

Jung et al., "New Efficient Method for the Total Synthesis of (S,S)-Isodityrosine from Natural Amino Acids," *J. Org. Chem.* 64:2976-2977 (1999).

Kamidawa et al., "Palladium-Catalyzed Amination of Aryl Bromides Utilizing Arene-Chromium Complexes as Ligands," *J. Org. Chem.* 63:8407-8410 (1998).

Kantlehner et al., "Beiträge zur Chemie von Orthokohlensäureestern und, α,α,α-Trialkoxyacetonitrien," *Kiebigs Ann. Chem.*, 7:507-529 (1982).

Katsura et al., "Studies on Antiulcer Drugs III.[1]" Synthesis and Antiulcer Activities of Imidazo[1,2-α]pyridinylethyl-benzoxazoles and Related Compounds: A Novel Class of Histamine H$_2$-Receptor Antagonists," *Chem. Pharm. Bull.*, 40(6):1424-1438 (1992).

Kawai et al., "Enhancement of Rat Urinary Bladder Tumorigenesis by Lipopolysaccharide-induced inflammation," *Cancer Res.* 53:5172-5175 (1993).

Kawase et al., "Trifluoroacetylation of Methylpyridines and Other Methylazines: A Convenient Access to Trifluoroacetonylazines," *Heterocycles*, 48(10):2103-2109 (1998).

Kitagawa et al., "Preparation and Root Growth-Modulatory Activity of N-Substituted 2-Acetylamino-2-ehtoxycarbonyl-3-(2-furyl)propanamides," *Chem. Pharm. Bull.*, 49(3):335-339 (2001).

Kordik et al., "Pyrazolecarboxamide Human Neuropepetide Y5 Receptor Ligands with In Vivo Antifeedant Activity," *Bioorganic & Medicinal Chemistry Letters*, 11:2287-2290 (2001).

Kraus et al., "A novel Fremy's salt-mediated oxidation and rearrangement of anilines into amino ortho-diketones. Applications to the synthesis of pyrrolobenzodiazepines," *Tetrahedron Letters*, 40:2039-2040 (1999).

Kriegler et al., "A Novel Form of TNF/Cachectin is a Cell Surface Cytotoxic Transmembrane Protein: Ramifications for the Complex Physiology of TNF," *Cell*, 53:45-53 (1988).

Kubo et al., "Nonpeptide Angiotensin II Receptor Antagnoists. Synthesis and Biological Activity of Benzimidazolecarboxylic Acids[1]," *J. Med. Chem.*, 36:2182-2195 (1993).

Kyriakis et al., "Sounding the Alarm: Protein Kinase Cascades Activated by Stress and Inflammation," *J. Biol Chem.*, 271:24313-24316 (1996).

Lazer et al., "Benzoxazolamines and Benzothiazolamines: Potent, Enantiselective Inhibitors of Leukotriene Biosynthesis with a Novel Mechanism of Action," *J. Med. Chem.*, 37:913-923 (1994).

Littke et al., "A Convenient and General Method for Pd-Catalyzed Suzuki Cross-Couplings of Aryl Chlorides and Arylboronic Acids," *Angew. Chem. Int. Ed.*, 37:3387-3388 (1998).

López-Rodríguez et al., "Benzimidazole Derivatives. 2. Synthesis and Structure—Activity Relationships of New Azabicyclic Benzimidazole-4-carboxylic Acid Derivatives with Affinity for Serotoninergic 5-HT$_3$ Receptors," *J. Med. Chem.*, 42;5020-5028 (1999).

Louie et al., "Palladium-Catalyzed Amination of Aryl Triflates and Importance of Triflate Addition Rate," *J. Org. Chem.*, 62:1268-1273 (1997).

Madhusudana et al., "Chemical Ionization Mass Spectrometry Using Ammonia as Reagent Gas: Mass Spectra of Pentacyclic Triterpenes," *Indian Journal of Chemistry*, 22B:370-373 (1983).

Manickam et al., "New Parts for a Construction Set of Bifunctional Oligo(het)arylene Building Blocks for Modular Chemistry," *Synthesis*, 3:442-446 (2000).

Mathis et al., "A Lipophilic Thioflavin—T Derivative for Positron Emission Tomography (PET) Imaging of Amyloid in Brain," *Bioorganic & Medicinal Chemistry Letters*, 12:295-298 (2002).

McCann et al., "The Nitric Oxide Hypothesis of Aging," *Exp. Gerontol*, 33(7-8):813-826 (1998).

McCann, "The Nitric Oxide Hypothesis of Brain Aging," *Exp. Gerontol*. 32:431-440 (1997).

Miyaura et al., "Palladium-Catalyzed Cross-Coupling Reactions of Organoboron Compounds," *Chem. Rev.* 95:2457-2483 (1995).

Molina et al., "The Role of Nitric Oxide in Neurodegeneration—Potential for Pharmacological Intervention," *Drugs & Aging*, 12(4):251-259 (1998).

Moroz et al., "The Ullmann Ether Condensation," *Russ. Chem. Rev.* 43:679-689 (1974).

Mourtas et al., "Solid Phase Synthesis of Benzothizaolyl Compounds," *Tetrahedron Letters*, 42:2201-2204 (2001).

Musser et al., "Synthesis and Antiallergic Activities of 1,3-Oxazolo[4,5-h]quinolines," *J. Med. Chem.*, 28:1255-1259 (1985).

Nagaraja et al., "Tissue Distribution and Excretion of CDRI-81/470 In Rats," *J. Pharm. Pharmacol..*, 52:1257-1264 (2000).

Oliff, "The Role of Tumor Necrosis Factor (Cachectin) in Cachexia," *Cell*, 54:141-142 (1988).

Oram, "Molecular Basic of Cholesterol Homeostasis: Lessons from Tangier Disease and ABCA1," *Trends in Molecular Medicines*, 8(4):168-173 (2002).

Paradisi, "Arene Substitution via Nucleophilic Addition to Electron Deficient Arenes," *Comprehensive Organic Synthesis* 4:423-450 (1991).

Petrov et al., "The Arbuzov Rearrangement with Participation of Halogenoacetylenes as a Method of Synthesis of Ethynylphosphonates and other Organo-phosphorus Compounds," *Russ. Chem. Rev.* 52:1030-1035 (1983).

Phoon et al., "Biological Evaluation of Hepatitis C Virus Helicase Inhibitors," *Bioorganic & Medicinal Chemistry Letters*, 11:1647-1650 (2001).

Pohlman et al., "An Endothelial Cell Surface Factor(s) Induced in Vitro By Lipopolysaccharide, Interleukin 1, and Tumor Necrosis Factor-α Increases Neutrophil Adherence by a CDw18-Dependent Mechanism," *J. Immunol*, 136: 4548-4553 (1986).

Pollock et al., "Purification and Characterization of Particulate Endothelium-derived Relaxing Factor Synthase from Cultured and Native Bovine Aortic Endothelial Cells," *Proc. Nat. Acad. Sci.*, 88:10480-10484 (1991).

Pujol-Borrell et al., "HLA Class II Induction In Human Islet Cells By Interferon- Plus Tumour Necrosis Factor or Lymphotoxin," *Nature*, 326:304-306 (1987).

Racanè et al., "Synthesis of Bis-Substituted Amidinobenzothiazoles as Potential Anti-HIV Agents," *Heterocycles*, 55(11):2085-2098 (2001).

Reddy et al., "Synthesis of 2-(2-Amino-3-pyridyl)benzimidazoles," *Indian Journal of Chemistry*, 23(b):866-867 (1984).

Reich et al., "Design and Synthesis of Novel 6,7-Imidazotetrahydroquinoline Inhibitors of Thymidylate Synthase Using Iterative Protein Crystal Structure Analysis[1]," *J. Med. Chem.*, 35:847-858 (1992).

Robl et al., "A Novel Series of Highly Potent Benzimidazole-Based Microsomal Triglyceride Transfer Protein Inhibitors," *Journal of Medicinal Chemistry*, 44(6):851-856 (2001).

Rosin et al., "Inflammation, Chromosomal Instability, and Cancer: The Schistosomiasis Model" *Cancer Res.*, 54 (7 Suppl):1929s-1933s (1994).

Ross "Atherosclerosis—An Inflammatory Disease," *New England Journal of Medicine*, 340(2):115-126 (Jan. 1999).

Roulleau et al., "Chimie Des Sucres Sans Groupements Protecteurs: Esterification Regioselective De L'hydroxyle Anomere Du Lactose Libre," *Tetrahedron Letters*, 24(7):719-722 (1983).

Rust et al. "Tangier disease is caused by mutations in the gene encoding ATP-binding cassette transporter 1," *Nature Genetics*, 22:352-355 (Aug. 1999).

Sanders, "Asthma, Viruses, and Nitric Oxide," *Proc. Soc. Exp. Biol. Med.*, 220(3):123-132 (1999).

Sandm eyer, "Ueber die Einwirkung von Imidokohlensäureester auf aromatische Orthoverbindugen," *Chem. Ber.* 19:2650-2667 (1886).

Scarborough et al., "Novel Tricyclic Benzothiazolo[2,3-c]thiadiazine Antagonists of the Platelet ADP Receptor (P2Y$_{12}$)," *Bioorganic & Medicinal Chemistry Letters*, 11:1805-1808 (2001).

Schandendorf et al., "Retinoic Acid Receptor-γ Selective Retinoids Exert Antiproliferative Effects on Human Melanoma Cell Growth *In Vitro*," *International Journal of Oncology* 5:1325-1331 (1994).

Schoenwald et al., "Topical Carbonic Anhydrase Inhibitors," *J. Med. Chem.*, 27:810-812 (1984).

Serfaty-Lacrosniere et al., "Homozygous Tangier disease and cardiovascular disease," *Atherosclerosis*, 107:85-98 (1994).

Shao et al., "p53 Independent $G_0/G_1$ Arrest and Apoptosis Induced by a Novel Retinoid in Human Breast Cancer Cells," *Oncogene* 11:493-504 (1995).

Smith et al., "The Active Form of Tumor Necrosis Factor Is A Trimer," *J. Biol. Chem.*, 262:6951-6954 (1987).

Sparrow et al., "A Potent Synthetic LXR Agonist is More Effective than Cholesterol Loading at Inducing ABCA1 mRNA and Stimulating Cholesterol Efflux," *Journal of Biological Chemistry*, 277(12):10021-10027 (2002).

Spruce et al., "Heteroarotinoids. Synthesis, Characterization, and Biological Activity in Terms of an Assessment of these Systems to Inhibit the Induction of Ornithine Decarboxylase Activity and to Induce Terminal Differentiation of HL-60 Cells," *J. Med. Chem.* 30:1474-1482 (1987).

Standaert et al., "Insulin Activates Protein Kinases $C\text{-}^{(INSERT)}$ and $C^{(INSERT)}$ by an Autophosphorylation-depending Mechanism and Stimulates Their Translocation to GLUT4 Vesicles and Other Mebrane Fractions in Rat Adipocytes," *J. Biol. Chem.* 274:25308-25316 (1999).

Stanforth, "Catalytic Cross-Coupling Reactions in Biaryl Synthesis," *Tetrahedron*, 54:263-303 (1998).

Stirling et al., "Increase In Exhaled Nitric Oxide Levels in patients With Difficult Asthma and Correlation With Symptoms and Disease Severity Despite Treatment With Oral and Inhaled Corticosteroids," *Thorax*, 53(12):1030-1034 (1998).

Strieter et al., "Endothelial Cell Gene Expression of a Neutrophil Chemotactic Factor by TNF-α, LPS, and IL-1β," *Science*, 243:1467-1469 (1989).

Suter et al., "Studien über Benzthiazole als eventuelle orale Antidiabetica," *Helvetica Chimica Acta*, 50(4):1084-1086 (1967).

Suzuki, "New Synthetic Transformations Via Organoboron Compounds," *Pure & Applied Chem.*, 66:213-222 (1994).

Teboul et al., "Thiazolidinediones and Fatty Acids Convert Myogenic Cells Into Adipose-like Cells," *J. Biol. Chem.* 270:28183-28187 (1995).

Testa et al., "AKT plays a central role in tumorigenesis," *PNAS*, 98:(20)10983-10985 (2001).

Thompson et al., "Effect of carcinogen dose and age at administration on induction of mammary carcinogenesis by 1-methyl-1-nitrosourea," *Carginogenesis*, 13(9):1535-1539 (1992).

Thorns et al., "nNOS Expressing Neurons in the Entorhinal Cortex and Hippocampus Are Affected in Patients With Alzheimer's Disease," *Exp. Neurol*, 150:14-20 (1998).

Tietze et al., "The Knoevenagel Reaction," *Comprehensive Organic Synthesis*, 2:341-394 (1991).

Tracey et al., "Anti-Cachectin/TNF Monoclonal Antibodies Prevent Septic Shock During Lethal Bacteraemia," *Nature*, 330:662-664 (1987).

Tracey et al., "Tumor Necrosis Factor: A Pleiotropic Cytokine and Therapuetic Target," *Ann. Rev. Med.* 45:491-503 (1994).

Uysal et al., "Protection From Obesity-induced Insulin Resistance in Mice Lacking TNF-α Function," *Nature* 389:610-614 (1997).

Wadsworth, "Synthetic Applications of Phosphoryl-Stabilized Anions," *Organic Reactions* 25:73-253 (1977).

Walter et al., "The High Density Lipoprotein—and Apolipoprotein A-1-Induced Mobilization of Cellular Cholesterol is Impaired in Fibroblasts from Tangier Disease Subjects," *Biochemical and Biophysical Research Communications*, 205(1):850-856 (1994).

Watanabe et al., "Synthesis of Sterically Hindered Biaryls via the Palladium-Catalyzed Cross-Coupling Reaction of Arylboronic Acids or Their Esters With Haloarenes," *Synlett.* 207-210 (1992).

Webb et al., "Diaphenyl Cyancarbonimidate and Dichlorodipenoxymethane as Synthons for the Construction of Heterocyclic Systems of Medicinal Interest," *J. Heterocyclic Chem.*, 24:275-278 (1987).

Weiberth et al., "Copper(I)-Activated Addition of Grignard Reagents to Nitriles. Synthesis of Ketimines, Ketones, and Amines," *J. Org. Chem.* 52:3901-3904 (1987).

Willson et al., "The Structure-Activity Relationship Between Peroxisome Proliferator-Activated Receptor Agonism and the Antihyperglycemic Activity of Thiazolidinediones," *J. Med. Chem.*, 39:665-668 (1996).

Wolfe et al., "Scope and Limitations of the Pd/BINAP-Catalyzed Amination of Aryl Bromides," *J. Org. Chem.* 65:1144-1157 (2000).

Wolfe et al., "Simple, Efficient Catalyst System for the Palladium-Catalyzed Amination of Aryl Chlorides, Bromides and Triflates," *J. Org. Chem.* 65:1158-1174 (2000).

Yadav et al., "Zinc Promoted Simple and Convenient Synthesis of Carbamates: An Easy Access for Amino Group Protection," *Tetrahedron Letters*, 39:3259-3262 (1998).

Yun et al., "Neurobiology of Nitric Oxide," *Crit. Rev. Neurobiol.*, 10:291-316 (1996).

Zaidi et al., "New Anti-mycobacterial Hydantoins," *Pharmazie*, 35, H12 (1980).

Zask et al., "Synthesis of 3-Mercapto-2(5H)-Furanones via Reaction of Dilithio-2,4-thiazolidinedione With α-Halo Ketones," Tetrahedron Letters, 34 (17):2719-2722 (1993).

Zask et al., "Synthesis and Antihyperglycemic Activity of Novel 5-(naphthalenylsufonyl)-2,4-thiazolidinediones," *J. Med. Chem.*, 33:1418-1423 (1990).

Zhou et al., "Cytoplasmic localization of p21$^{Cip1/WAF1}$ by Akt-induced phosphorylation in HER-2/*neu*-overexpressing cells," *Nature Cell Biol.*, 3:245-252 (2001).

* cited by examiner

N-SUBSTITUTED HETEROCYCLES FOR THE TREATMENT OF HYPERCHOLESTEREMIA, DYSLIPIDEMIA AND OTHER METABOLIC DISORDERS; CANCER, AND OTHER DISEASES

RELATED APPLICATIONS

This application claims priority to the U.S. Provisional Application Ser. No. 60/334,794, filed Nov. 15, 2001, the disclosure of which application is hereby incorporated in its entirety by this reference. This application claims priority to U.S. Provisional Application No. 60/362,702, filed Mar. 8, 2002, the disclosure and description of which is hereby incorporated by reference in its entirety into the current application for all purposes, and particularly for its disclosures of potential structures for $Ar_1$ groups having amide groups incorporated therein, and methods for the precursors employed for the synthesis of the $Ar_1$ groups of the current invention. This application also claims priority to U.S. Provisional Application No. 60/362,732, filed Mar. 8, 2002. The disclosure of U.S. Provisional Application No. 60/362,732 is hereby incorporated by reference in its entirety into the current application for all purposes, and particularly for its disclosures of potential structures for bicyclic heterocyclic $Ar_1$ groups, and methods for the precursors employed for the synthesis of the bicyclic heterocyclic $Ar_1$ groups of the current invention.

BACKGROUND OF THE INVENTION

Metabolic disorders such as obesity, Type 2 diabetes, dyslipidemia and hypercholesteremia have dramatically increased in the United States, other developed countries and even in some developing countries due to a combination of high calorie, high lipid content diets and sedentary life styles. Among other things, patients suffering from the above disorders or diseases are at risk for the development of artherosclerosis and heart disease, which are the second most frequent cause of death in the U.S. Dietary restrictions combined with exercise are known to be useful for the prevention, and in some cases, reversal of the above metabolic disorders, but have turned out to be rather ineffective when looking at populations in general. Drug treatment, therefore, appears presently to be necessary to prevent and treat metabolic disorders such as obesity, Type 2 diabetes, dyslipidemia and hypercholesteremia, and thereby prevent the development of serious side effects in particular cardiovascular disease. While a number of drugs have been developed over the years to treat the various metabolic disorders, these drugs can often have side effects or are effective only for a limited time period or function only in combination with dietary restrictions.

Compounds having activity for treating diabetes and related metabolic disorders were disclosed in PCT publications WO 01/16122 and WO 01/16123, both published Mar. 8, 2001. The disclosures of both WO 01/16122 and WO 01/16123 are hereby incorporated in their entirities by this reference, for all purposes, and particularly for their disclosures of the structures of their compounds and their biological activities and utilities.

Additionally, solid tumors are the leading cause of death attributable to cancers worldwide. Conventional methods of treating cancer include surgical treatments, the administration of chemotherapeutic agents, and recently immune based treatments, which typically involve the administration of an antibody or antibody fragment. Although some encouraging results are being reported with the latter, an effective, life-prolonging treatment or a cure is not yet available for most cancers.

SUMMARY OF THE INVENTION

In accordance with the purposes of this invention, as embodied and broadly described herein, this invention, in one aspect, relates to certain novel compounds, compositions comprising the compounds, and methods related to the regulation of metabolism and the treatment of cancer by administering the compounds and/or compositions of the invention to animals and/or humans.

Described herein are novel substituted heterocyclic compounds that are useful for the treatment of certain metabolic disorders including Type 2 diabetes, dyslipidemia and hypercholesteremia. The compounds of the invention are believed to be ligands for the nuclear receptors RXR, PPARα, PPARγ, PPARδ, LXR and/or FXR or other targets wich could be important proteins such as kinases and/or phosphatases that are involved in metabolic disorders. The compounds of the invention can also have anticancer activities in view of their ability to inhibit AKT Kinase. AKT, also called PKB, is the cellular homologue of the transforming viral oncogene v-AKT. Deregulation of AKT activity can be associated with oncogenic activity, and AKT is overexpressed in certain cancers and/or diseases of uncontrolled cellular proliferation, including pancreatic and ovarian carcinomas. Therefore, the compounds of the invention that inhibit AKT can have anticancer activity. In summary, the compounds and/or compositions described herein are useful for the treatment of metabolic disorders and/or cancer.

Additional advantages of the invention will be set forth in part in the description which follows, and in part will be obvious from the description, or may be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

DETAILED DESCRIPTION

Definitions

Figure 1:
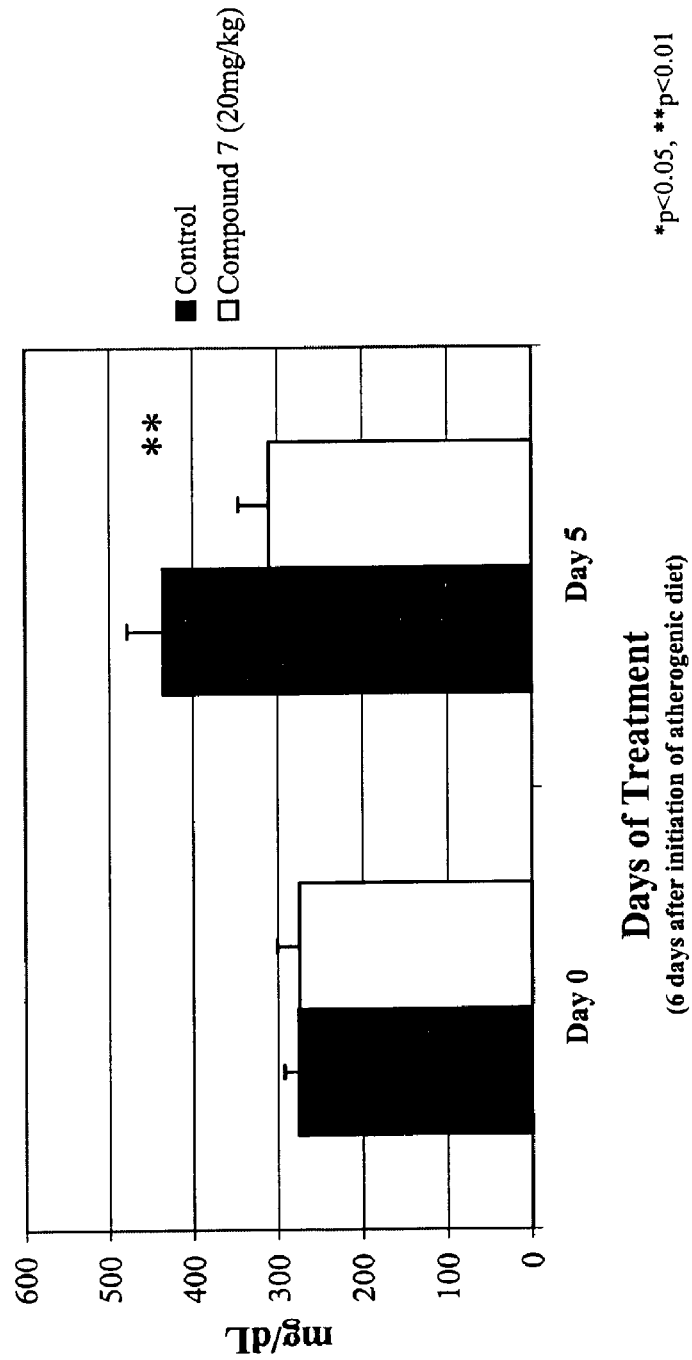
FIG. 1 shows the total cholesterol levels in HSD Rats maintained on an atherogenic diet after treatment with Compound 7.

In the specification and Formulae described herein the following terms are hereby defined:

The term "alkyl" denotes a saturated hydrocarbon radical containing 1 to 8 carbons. An alkyl is structurally similar to a non-cyclic alkane compound modified by the removal of one hydrogen from the non-cyclic alkane and the substitution therefore of a non-hydrogen group or radical. Alkyl radicals can be branched or unbranched. Lower alkyl radicals have 1 to 4 carbon atoms. Higher alkyl radicals have 5 to 8 carbon atoms. Examples of alkyl, lower alkyl and higher radicals include, but are not limited to, methyl, ethyl, n-propyl, iso-propyl, n-butyl, sec-butyl, t-butyl, amyl, t-amyl, n-pentyl, n-hexyl, i-octyl and like radicals.

The term "alkenyl" denotes an unsaturated hydrocarbon radical containing 1 to 8 carbons and at least one carbon-carbon double bond. The unsaturated hydrocarbon radical is similar to an alkyl radical as defined above that also comprises at least one carbon-carbon double bond. Examples include, but are not limited to, vinyl, allyl, 2-butenyl, 3-butenyl, 2-pentenyl, 3-pentenyl, 4-pentenyl, 2-hexenyl, 3-hexenyl, 4-hexenyl, 5-hexanyl, 2-heptenyl, 3-heptenyl, 4-heptenyl, 5-heptenyl, 6-heptenyl and the like. The term "alkenyl" includes dienes and trienes of straight and branch chains.

The term "alkynyl" denotes a hydrocarbon radical containing 1 to 8 carbons and at least one triple bond. Examples include, but are not limited to, ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl and the like. The term "alkynyl" includes di- and tri-ynes.

The term "substituted alkyl" denotes an alkyl radical as defined above that contains 1–8 carbon atoms and also has bonded thereto one or more organic or inorganic substituent radicals. In some embodiments, 1 or 2 organic or inorganic substituent radicals are employed. In some embodiments, each organic substituent radical comprises between 1 and 4, or between 5 and 8 carbon atoms. Suitable organic and inorganic substituent radicals include but are not limited to hydroxyl, halide, cycloalkyl, amino, mono-substituted amino, di-substituted amino, acyloxy, nitro, cyano, carboxy, carboalkoxy, alkylcarboxamide, substituted alkylcarboxamide, dialkylcarboxamide, substituted dialkylcarboxamide, alkylsulfonyl, alkylsulfinyl, thioalkyl, thiohaloalkyl, alkyl sulfonamide, aryl sulfonamide, heteroaryl sulfonamide, alkoxy, substituted alkoxy, haloalkoxy, haloalkyl, aryl, substituted aryl, heterocyclic, substituted heterocyclic, heteroaryl and substituted heteroaryl. When the substituted alkyl is bonded thereon with more than one substituent radical, then the substituent radicals may be the same or different.

The term "substituted alkenyl" denotes an alkenyl radical as defined above, containing 1 to 8 carbons bonded thereon with one or more organic or inorganic substituent radicals. In some embodiments, 1 or 2 organic or inorganic substituent radicals are employed. In some embodiments, each organic substituent radical comprise between 1 and 4, or between 5 and 8 carbon atoms. Suitable organic and inorganic substituent radicals include but are not limited to halogen, hydroxyl, cycloalkyl, amino, mono-substituted amino, di-substituted amino, acyloxy, nitro, cyano, carboxy, carboalkoxy, alkylcarboxamide, substituted alkylcarboxamide, dialkylcarboxamide, substituted dialkylcarboxamide, alkylsulfonyl, alkylsulfinyl, thioalkyl, thiohaloalkyl, alkoxy, substituted alkoxy, haloalkyl, haloalkoxy, aryl, hetercyclic, or heteroaryl. When the substituted alkenyl is bonded thereon with more than one substituent radical, then the substituent radicals may be the same or different.

The term "substituted alkynyl" denotes an alkynyl radical containing 1 to 8 carbons bonded thereon with one or more organic or inorganic substituent radicals. In some embodiments, 1 or 2 organic or inorganic substituent radicals are employed. In some embodiments, each organic substituent radical comprise between 1 and 4, or between 5 and 8 carbon atoms. Suitable organic and inorganic substituent radicals include but are not limited to halogen, hydroxyl, cycloalkyl, amino, mono-substituted amino, di-substituted amino, acyloxy, nitro, cyano, carboxy, carboalkoxy, alkylcarboxamide, substituted alkylcarboxamide, dialkylcarboxamide, substituted dialkylcarboxamide, alkylsulfonyl, alkylsulfinyl, thioalkyl, thiohaloalkyl, alkoxy, substituted alkoxy or haloalkoxy. When the substituted alkynyl is bonded thereon with more than one substituent radical, then the substituent radicals may be the same or different.

The term "cycloalkyl" denotes a saturaturated hydrocarbon radical containing 3 to 8 ring carbons that comprises part or all of a compound having a ring structure. A cycloalkyl radical is structurally similar to a cyclic alkane compound modified by the removal of one hydrogen from the cyclic alkane and the substitution therefore of a non-hydrogen group or residue. Examples include, but are not limited to, cyclopropyl, cyclobutyl, cyclopentyl, cyclopentyl, cyclohexyl, cycloheptyl and the like. It is understood that cycloalkyl radicals may be bonded or fused together with other radicals, such as, aryl radicals, to form fused cycloalkyl radicals that are within the scope of this definition. One example of such a fused cycloalkyl radical is represented by the 5,6,7,8 carbons of a 5,6,7,8-tetrahydro-2-naphthyl radical having the structure:

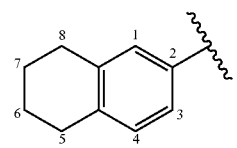

The 5,6,7,8-tetrahydro-2-naphthyl radical itself comprises an aryl radical and a cyclohexane radical, wherein the delocalized and relatively unreactive double bonds that are part of the aryl radical are not considered, for the purposes of this application, as a part of the cycloalkyl radical.

The term "substituted cycloalkyl" denotes a cycloalkyl as defined above having bonded thereon one or more additional organic or inorganic substituent radicals. In some embodiments the cycloalkyl residue comprises 1, 2, 3, or 4 substitutent radicals. Suitable organic and inorganic substituent radicals include but are not limited to halogen, alkyl, substituted alkyl, hydroxyl, alkoxy, substituted alkoxy, carboxy, carboalkoxy, alkylcarboxamide, substituted alkylcarboxamide, dialkylcarboxamide, substituted dialkylcarboxamide, amino, mono-substituted amino or di-substituted amino. When the substituted cycloalkyl is bonded thereon with more than one substituent radical, then the substituent radicals may be the same or different.

The term "cycloalkenyl" denotes a partially unsaturated analog of a cycloalkyl radical containing 3 to 8 ring carbons that further comprises at least one carbon-carbon double bond in the ring. Examples include, but are not limited to, cyclopropenyl, 1-cyclobutenyl, 2-cyclobutenyl, 1-cyclopentenyl, 2-cyclopentenyl, 3-cyclopentenyl, 1-cyclohexyl, 2-cyclohexyl, 3-cyclohexyl and the like. It is understood that cycloalkenyl radicals bonded together with other radicals, such as, aryl radicals, to form fused cycloalkenyl radicals are within the scope of this definition.

The term "substituted cycloalkenyl" denotes a cycloalkenyl radical having one or more organic or inorganic substituent groups or radicals. In some embodiments the cycloalkenyl residue comprises 1, 2, 3, or 4 substituent groups or radicals. Suitable organic and inorganic substituent radicals include but are not limited to halogen, alkyl, hydroxyl, alkoxy, substituted alkoxy, haloalkoxy, carboxy, carboalkoxy, alkylcarboxamide, substituted alkylcarboxamide, dialkylcarboxamide, substituted dialkylcarboxamide, amino, mono-substituted amino or di-substituted amino. When the substituted cycloalkenyl is bonded thereon with more than one substituent radical, then the substituent radicals may be the same or different.

The term "alkoxy" as used herein refers to an alkyl radical bound through a single, terminal ether linkage; that is, an "alkoxy" group can be defined as —OR where R is alkyl as defined above. Examples include, but are not limited to, methoxy, ethoxy, n-propoxy, iso-propoxy, n-butoxy, t-butoxy, iso-butoxy and the like.

The term "substituted alkoxy" denotes an alkoxy radical as defined above having one, two, or more additional organic or inorganic substituent radicals bound to the alkyl radical. Suitable organic and inorganic substituent radicals include but are not limited to hydroxyl, cycloalkyl, amino, mono-substituted amino, di-substituted amino, acyloxy, nitro, cyano, carboxy, carboalkoxy, alkylcarboxamide, substituted alkylcarboxamide, dialkylcarboxamide, substituted dialkylcarboxamide, alkylsulfonyl, alkylsulfinyl, thioalkyl, thiohaloalkyl, alkoxy, substituted alkoxy or haloalkoxy. When the alkyl of the alkoxy is bonded thereon with more than one substituent radical, then the substituent radicals may be the same or different.

The term "amino" denotes a substituted or unsubstituted trivalent nitrogen-containing radical or group that is structurally related to ammonia ($NH_3$) by the substitution of one or more of the hydrogen atoms of ammonia by a substituent radical.

The term "mono-substituted amino" denotes an amino substituted with one radical selected from alkyl, substituted alkyl or arylalkyl wherein the terms have the same definitions found herein.

The term "di-substituted amino" denotes an amino substituted with two radicals that may be same or different selected from aryl, substituted aryl, alkyl, substituted alkyl or arylalkyl wherein the terms have the same definitions as disclosed herein. Examples include, but are not limited to, dimethylamino, methylethylamino, diethylamino and the like. The two substituent radicals present may be the same or different.

The term "haloalkyl" denotes a alkyl radical, as defined above, substituted with one or more halogens, such as flourine, chlorine, bromine, or iodine preferably fluorine. Examples include but are not limited to trifluoromethyl, pentafluoroethyl and the like.

The term "haloalkoxy" denotes a haloalkyl, as defined above, that is directly bonded to oxygen to form trifluoromethoxy, pentafluoroethoxy and the like.

The term "acyl" denotes a radical containing a carbonyl (—C(O)—R group) wherein the R group is hydrogen or has 1 to 8 carbons. Examples include, but are not limited to, formyl, acetyl, propionyl, butanoyl, iso-butanoyl, pentanoyl, hexanoyl, heptanoyl, benzoyl and the like.

The term "acyloxy" denotes a radical containing a carboxyl (—O—C(O)—R) group wherein the R group comprises hydrogen or 1 to 8 carbons. Examples include, but are not limited to, acetyloxy, propionyloxy, butanoyloxy, iso-butanoyloxy, benzoyloxy and the like.

The term "aryl" denotes a radical comprising at least one unsaturated and conjugated six membered ring analogous to the six membered ring of benzene. Aryl radicals having such unsaturated and conjugated rings are also known to those of skill in the art as "aromatic" radicals. Preferred aryl radicals have 6 to 12 ring carbons. Aryl radicals include, but are not limted to, aromatic radicals comprising phenyl and naphthyl ring radicals.

The term "substituted aryl" denotes an aromatic radical wherein the aromatic ring is bonded to one or more additional organic or inorganic substituent radicals. In some embodiments the sustituted aryl residue comprises 1, 2, 3, 4, or 5 additional substitutent groups or radicals. Suitable organic and inorganic substituent radicals include, but are not limited to, hydroxyl, cycloalkyl, aryl, substituted aryl, heteroaryl, heterocyclic ring, substituted heterocyclic ring, amino, mono-substituted amino, di-substituted amino, acyloxy, nitro, cyano, carboxy, carboalkoxy, alkylcarboxamide, substituted alkylcarboxamide, dialkylcarboxamide, substituted dialkylcarboxamide, alkylsulfonyl, alkylsulfinyl, thioalkyl, alkoxy, substituted alkoxy or haloalkoxy radicals, wherein the terms are defined herein. Unless otherwise indicated herein, the organic substituents can comprise from 1 to 4 or from 5 to 8 carbon atoms. When a substituted aryl radical is bonded thereon with more than one substituent radical, then the substituent radicals may be the same or different.

The terms "halo," "halogen," or "halide" refers to a fluoro, chloro, bromo or iodo atom or ion.

The term "alkylsulfonyl" refers to a sulfone radical containing 1 to 8 carbons, linear or branched. Examples include, but are not limited to, methylsulfonyl, ethylsulfonyl, isopropylsulfonyl having the structures $CH_3S(O)_2$—, $CH_3CH_2S(O)_2$—, $(CH_3)_2CHS(O)_2$— respectively and the like.

The term "alkylsulfinyl" refers to a sulfoxide radical containing 1 to 8 carbons, linear or branched. Examples include but are not limited to methylsulfinyl, ethylsulfinyl, isopropylsulfinyl having the structures $CH_3S(O)$—, $CH_3CH_2S(O)$—, $(CH_3)_2CHS(O)$— respectively and the like.

The term "thioalkyl" refers to a sulfide radical containing 1 to 8 carbons, linear or branched. In one embodiment the thioalkyl refers a $C_1$–$C_8$ thioalkyl. In another embodiment the thioalkyl refers to a $C_5$–$C_8$ thioalkyl. In still another embodiment the thioalkyl refers to a $C_1$–$C_4$ thioalkyl. Examples include but are not limited to methylsulfide, ethyl sulfide, isopropylsulfide, pentylsulfide having the structures CH₃S—, CH₃CH₂S—, (CH₃)₂CHS—, CH₃(CH₂)₄S— respectively and the like.

The term "thiohaloalkyl" denotes a thioalkyl radical wherein the alkyl moiety is substituted with one or more halogens. Examples include but are not limited to trifluoromethylthio, 1,1-difluoroethylthio, 2,2,2-trifluoroethylthio and the like.

The term "carboalkoxy" refers to an alkyl ester of a carboxylic acid, wherein alkyl has the same definition as found above. Examples include but are not limited to carbomethoxy, carboethoxy, carboisopropoxy and the like.

The term "alkylcarboxamide" denotes a radical having the structure HN(R)—C(O)— or —C(O)—N(R)H wherein a single alkyl group R is attached to the nitrogen atom of an amide, i.e. Examples include but are not limited to N-methylcarboxamide, N-ethylcarboxamide, N-(iso-propyl)carboxamide and the like.

The term "substituted alkylcarboxamide" denotes a radical having "substituted alkyl" group attached to the nitrogen atom of an alkylcarboxamide radical.

The term "dialkylcarboxamide" denotes two alkyl radicals or groups (i.e., R' and R") that are the same or different attached to the nitrogen atom of a carboxamide (—C(O)—N(R')(R")) radical. Examples include, but are not limited to, N,N-dimethylcarboxamide, N-methyl-N-ethylcarboxamide and the like.

The term "substituted dialkylcarboxamide" denotes an dialkylcarboxamide residue having two alkyl radicals attached to the nitrogen of the dialkylcarboxyamide residue, where one or both groups is a "substituted alkyl", as defined above. It is understood that these groups may be the same or different. Examples include, but are not limited to, N,N-dibenzylcarboxamide, N-benzyl-N-methylcarboxamide and the like.

The term "alkylene" denotes an acyclic or cyclic hydrocarbyl radical containing one to nine carbons that bridges two groups, such as, for example, Ar₁ and Ar₂, to give Ar₁-alkylene-Ar₂. Examples of alkylene radicals include, but are not limited to: —CH₂—, —CH₂CH₂—,

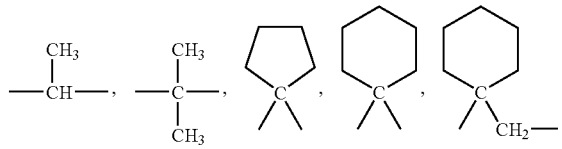

and the like.

The term "substituted alkylene" denotes an alkylene radical defined above containing one to nine carbons that is further substituted with at least one additional group, selected from but not limited to hydroxyl, cycloalkyl, amino, mono-substituted amino, di-substituted amino, acyloxy, nitro, cyano, carboxy, carboalkoxy, alkylcarboxamide, substituted alkylcarboxamide, dialkylcarboxamide, substituted dialkylcarboxamide, alkylsulfonyl, alkylsulfinyl, thioalkyl, thiohaloalkyl, alkoxy, substituted alkoxy, haloalkyl, or haloalkoxy. When the substituted alkylene is bonded thereon with more than one substituent radical then the substituent radicals may be the same or different.

The term "heterocyclic ring" is a radical that comprises at least a four, five-membered or six-membered ring that is completely or partially saturated and comprises one, two, or three ring heteroatoms, selected from nitrogen, oxygen and/or sulfur. Heterocyclic rings need not but often comprise one, two, three, four, or five carbon atoms. Examples include but are not limited to morpholino, piperidinyl, piperazinyl, tetrahydrofuranyl and the like.

The term "substituted heterocyclic ring" refers to a heterocyclic ring bonded to one, two, three, four, five, or more organic or inorganic substituent radicals. Suitable organic and inorganic substituent radicals include but are not limited to halogen, hydroxyl, alkyl, substituted alkyl, haloalkyl, phenyl, substituted phenyl, heteroaryl, amino, mono-substituted amino, di-substituted amino, acyloxy, nitro, cyano, carboxy, carboalkoxy, alkylcarboxamide, substituted alkylcarboxamide, dialkylcarboxamide, substituted dialkylcarboxamide, alkylsulfonyl, alkylsulfinyl, thioalkyl, alkoxy, substituted alkoxy or haloalkoxy. When the substituted heterocyclic ring is bonded thereon with more than one substitutent radical then the substitutent radicals may be the same or different.

The term "heteroaryl" denotes a radical that comprises at least a five-membered or six-membered unsaturated and conjugated aromatic ring containing at least two ring carbon atoms and 1 to 4 ring heteroatoms selected from nitrogen, oxygen and/or sulfur. Such heteroaryl radicals are often alternatively termed "heteroaromatic" by those of skill in the art. In some embodiments the heteroaryl radicals have from two to twelve carbon atoms, or alternatively 4 to 5 carbon atoms in the heteroaryl ring. Examples include, but are not limited to, pyridinyl, pyrimidinyl, pyrazinyl, pyrrolyl, furanyl, tetrazolyl, isoxazolyl, oxadiazolyl, benzothiophenyl, benzofuranyl, quinolinyl, isoquinolinyl and the like.

The term "substituted heteroaryl" denotes a heteroaryl radical wherein the heteroaryl ring is bonded to one or more organic or inorganic substituent radicals. In some embodiments the sustituted aryl residue comprises 1, 2, 3, 4, or 5 additional substitutent radicals. Suitable organic and inorganic substituent radicals include, but are not limited to, hydroxyl, cycloalkyl, aryl, substituted aryl, heteroaryl, heterocyclic ring, substituted heterocyclic ring, amino, mono-substituted amino, di-substituted amino, acyloxy, nitro, cyano, carboxy, carboalkoxy, alkylcarboxamide, substituted alkylcarboxamide, dialkylcarboxamide, substituted dialkylcarboxamide, alkylsulfonyl, alkylsulfinyl, thioalkyl, alkoxy, substituted alkoxy or haloalkoxy radicals, wherein the terms are defined herein. Unless otherwise indicated herein, the organic substituents may comprise from 1 to 4 or from 5 to 9 carbon atoms. When the substituted heteroaryl is bonded thereon with more than one substitutent radical then the substitutent radicals may be the same or different.

The term radical, as used in the specification and concluding claims, refers to a fragment, group, or substructure of a molecule described herein regardless of how the molecule is prepared. The number of carbon atoms in a radical is not critical to the present invention and may be as as few as zero. Examples of radicals containing no carbons are "inorganic radicals" that include, but are not limited to, amino, hydroxy, halogens, nitro, thiol, sulfate, or like inorganic radicals. An "organic radical" contains one or more carbon atoms, although it may optionally contain one or more heteroatoms such as O, S, N, P, halogens, and the like. Suitable organic radicals include but are not limited to alkyl, substituted alkyl, alkenyl, substituted alkenyl, alkynyl, substituted alkynyl, acyloxy, alkoxy, substituted alkoxy, acyl, mono-substituted amino, di-substituted amino, carboxy, carboalkoxy, alkylcarboxamide, substituted alkylcarboxamide, dialkylcarboxamide, substituted dialkylcarboxamide, alkylsulfonamide, arylsulfonamide, alkylurea, arylurea, alkylcarbamate, arylcarbamate, heteroaryl, haloalkoxy, alkylsulfonyl, alkylsulfinyl, thioalkyl or thiohaloalkyl. An organic radical may have twenty-six or less carbon atoms, twenty-one or carbon atoms, thirteen or less carbon atoms, 6 or less carbon atoms. Lower organic radicals comprise between one and four carbon atoms. One example, of a carbon containing radical is a 5,6,7,8-tetrahydro-2-naphthyl radical, i.e. fragments having the structure:

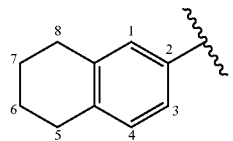

A 5,6,7,8-tetrahydro-2-naphthyl radical itself comprises a benzene radical and a cyclohexane radical, and can be further substituted with one or more other organic substitutent radicals, such as, for example, an alkoxy radical, a lower alkyl radical, etc., as disclosed elewhere herein. In some embodiments, one of the carbon atoms of the organic subtituent radical is bonded in a terminal fashion through a heteroatom or inorganic radical, such as oxygen, sulfur, nitrogen, phosphorus, phosphates, or the like, and the heteroatom or inorganic radical can itself have one, two, or more organic substituent radicals, such as for example, a trifluoromethoxy radical or a dimethylamino radical.

A residue of a chemical species, as used in the specification and concluding claims, refers to the moiety that is the resulting product of the chemical species in a particular reaction scheme or subsequent formulation or chemical product, regardless of whether the moiety is actually obtained from the chemical species. Thus, an ethylene glycol residue in a polyester refers to one or more —OCH$_2$CH$_2$O— repeat units in the polyester, regardless of whether ethylene glycol is used to prepare the polyester.

It must be noted that, as used in the specification and the appended claims, the singular forms "a," "an" and "the" can include plural referents unless the context clearly dictates otherwise. Thus, for example, reference to "an aromatic compound" includes mixtures of aromatic compounds.

Often, ranges are expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

Compounds

The invention includes compounds of Formula (I):

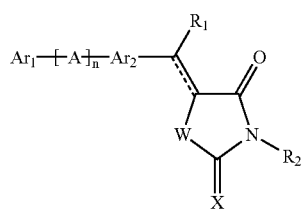

(I)

wherein
n is 0 or 1;
"- - -" is absent or present;
Ar$_1$ is a substituted or unsubstituted aryl radical or a substituted or unsubstituted heteroaryl radical;
Ar$_2$ is a substituted or unsubstituted aryl radical or a substituted or unsubstituted heteroaryl radical;
A is a substituted or unsubstituted bridging group or radical comprising from 1 to 12 C, O, S and/or N atoms, wherein N can be further substituted with hydrogen, or a substituted or unsubstituted radical comprising from one to 12 carbon atoms;
R$_1$ is hydrogen, a substituted or unsubstituted amino radical, or a substituted or unsubstituted organic radical;
R$_2$ is a substituted or unsubstituted organic radical;
W is —S—, —O— or —N—R$_3$ wherein R$_3$ is hydrogen, or a substituted or unsubstituted radical comprising from one to 12 carbon atoms; and
X is O or S;

or a pharmaceutically acceptable salt thereof.

The R$_1$ radicals of the compounds of Formula (I) are bonded to a methylene or methine carbon atom that bridges and/or connects the Ar$_2$ radical and a carbon atom of the N-substituted heterocyclic ring of the compounds of Formula (I). The R$_1$ radical can be hydrogen, or an organic radical that can be unsubstituted or substituted with one or more organic or inorganic substitutent radicals. In some embodiments, the R$_1$ radical can be hydrogen, alkyl, substituted alkyl, cycloalkyl, substituted cycloalkyl. In some embodiments, the R$_1$ radical can have from one to eight carbon atoms, or from one to six carbon atoms, or from one to four carbon atoms. In still another embodiment R$_1$ is hydrogen.

The methylene or methine carbon atom bonded to the R$_1$ radical will also be bonded to the N-substituted heterocyclic ring via a carbon-carbon single bond or a carbon-carbon double bond. In the embodiments of Formula (I) wherein the "- - -" is absent, a single carbon-carbon bond is present as shown in Formula (IIa). When the "- - -" in Formula (I) is present a carbon carbon double bond is present as shown in Formula (IIb).

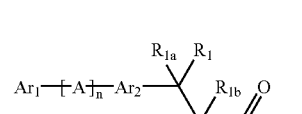

(IIa)

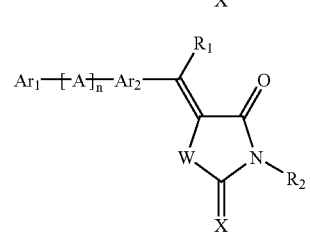

(IIb)

If the double bond of Formula I is absent, the methine carbon atom and the carbon atom of the N-substituted heterocyclic ring bonded thereto will each have an additional substituent radical (R$_{1a}$ and R$_{1b}$) as shown in Formula (Ia). The R$_{1a}$ and R$_{1b}$ substituent radicals can be the same or different, and are often both hydrogen, but $R_{1a}$ and $R_{1b}$ can also be inorganic radicals such as hydroxyl, halides, amino, thiol or the like, or can be another organic radical that can be the same or different than the $R_1$ radical.

In embodiments when the carbon-carbon double bond is present, both E and Z configurations of the double bond of compound (IIb) are possible. E configurations, Z configurations and mixtures of both E and Z configurations are within the scope of the invention. By way of examples, compounds of the present invention of Formula (I and/or IIb) can have one or both of the following structures:

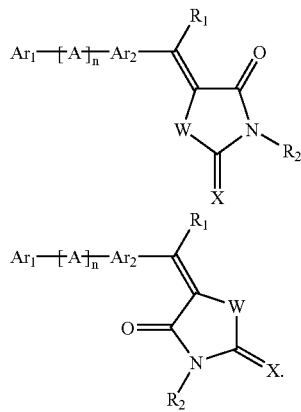

The $R_2$ radical is an N-substituent radical for the nitrogen atom of the heterocyclic ring of the compounds of Formula (I). $R_2$ is an organic radical and is not hydrogen.

$R_2$ can be a substituted or unsubstituted organic radical. In many embodiments, $R_2$ comprises one to twelve carbon atoms. The $R_2$ radical can be an alkyl, or an alkyl substituted with one, two, or more substitutent radicals. Suitable substitutent radicals for $R_2$ include but are not limited to hydroxyl, cycloalkyl, amino, mono-substituted amino, di-substituted amino, acyloxy, nitro, cyano, carboxy, carboalkoxy, alkylcarboxamide, substituted alkylcarboxamide, dialkylcarboxamide, substituted dialkylcarboxamide, alkylsulfonyl, alkylsulfinyl, alkyl sulfonamide, aryl sulfonamide, heteroaryl sulfonamide, thioalkyl, thiohaloalkyl, alkoxy, substituted alkoxy, haloalkoxy, aryl, substituted aryl, heteroaryl and substituted heteroaryl radicals. In some embodiments, the substituent radicals for the $R_2$ radical include but are not limited to hydroxyl, cycloalkyl, amino, mono-substituted amino, di-substituted amino, cyano, carboxy, carboalkoxy, alkylcarboxamide, alkylcarboxamide, dialkylcarboxamide, dialkylcarboxamide, alkylsulfonyl, alkylsulfinyl, thioalkyl, thiohaloalkyl, alkoxy, substituted alkoxy, haloalkoxy, aryl, substituted arl, hetercylic, substituted heterocyclic, heteroaryl and substituted heteroaryl radicals, or mixtures thereof. In some embodiments, each organic substituent radical comprises between 1 and 4, or between 5 and 8 carbon atoms. In some embodiments, the $R_2$ radical can be an alkyl, substituted alkyl, cycloalkyl or substituted cycloalkyl radical. In some embodiments, the $R_2$ radical can be alkyl or lower alkyl radical. In some embodiments, the $R_2$ radical can be an alkyl radical substituted with 1, 2, or 3 carboxy or heteroaryl radicals. In some embodiments, $R_2$ has the structure —$CH_2CO_2H$.

In many embodiment $R_2$ can be a $C_1$–$C_6$-alkyl, $C_3$–$C_8$ cycloalkyl, $C_2$–$C_6$ alkenyl, —$SO_2CH_3$, or —$(CH_2)_p$-SG where p is 0, 1, 2, or 3 and SG is cyano, —$OR_{10}$,

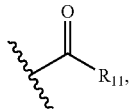

tetrazolyl, —$NR_{12}R_{13}$, —SH, $C_1$–$C_4$ alkylthio, or

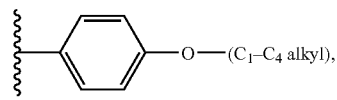

where $R_{10}$ is hydrogen, $C_1$–$C_4$ alkyl or

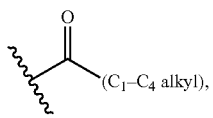

wherein $R_{11}$ is hydrogen $C_1$–$C_4$ alkyl $C_1$–$C_4$ alkoxy hydroxy or $NH_2$, and $R_{12}$ and $R_{13}$ are each independently hydrogen, $C_1$–$C_6$, $C_2$–$C_6$ alkenyl, phenyl, $C_1$–$C_4$ alkylphenyl, —$(CH_2)_qN(C_1$–$C_4$ alkyl$)_2$, or —$(CH_2)_q$—S—$(C_1$–$C_4$ alkyl$)_2$, where q is and an integer from 1 to 6, both inclusive, or $R_{12}$ and $R_{13}$, taken together with the nitrogen atom to which they are attached, form a morpholinyl, piperidinyl, or N-methylpiperazinyl ring. However, in embodiments of the present invention in which $Ar_1$ is a phenyl substituted with from one to three substitutents independently selected from $C_1$–$C_4$ alkylphenyl, phenyl, phenoxy, $C_1$–$C_4$ alkyloxyphenyl, thiophenyl, or $C_1$–$C_4$ alkylthiophenyl, the $R_2$ substituents recited in this paragraph may not be within the scope of this invention.

Certain embodiments of the invention relate to compounds wherein n is 0 or 1; i.e. the "A" radical bridging the $Ar_1$ and $Ar_2$ radicals can be either present or absent, so as to give compounds of the structures indicated below:

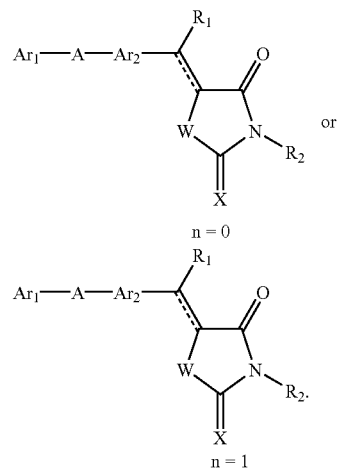

The A radical can be an organic or inorganic radical, and can comprise carbon, hydrogen, and a variety of heteroatoms. In some embodiments, the A radical comprises from 1 to 12 C, O, S and/or N atoms, wherein N can be further substituted with hydrogen. The A radical can also be a substituted or unsubstituted organic radical comprising from one to 12 carbon atoms. The A radical can comprise purely inorganic atoms or bridging radicals such as oxygen or sulfur atoms, sulfoxide, sulfone, sulfate, amino, and the like. The A radical can also comprise bridging organic radicals such as carbonyl, carboxy, alkylene, amide, and the like. In some embodiments, the A radical is not an aromatic or heteroaromatic group.

In some embodiments, the bridging A radical is a substituted or unsubstituted bridging radical, optionally comprising a connected chain of atoms, which comprises from 1 to 9 carbon atoms and optionally comprising one or more heteroatoms selected from O, S and N atoms. In some embodiments one or two heteroatoms are present. Any N atoms can optionally be further substituted with hydrogen, alkyl or substituted alkyl radicals. The bridging A radical can comprise additional organic or inorganic substitutent radicals, which can include but are not limited to hydrogen, alkyl, substituted alkyl, alkenyl, substituted alkenyl, alkynyl, substituted alkynyl, halogen, cyano, nitro, hydroxyl, acyloxy, alkoxy, substituted alkoxy, acyl, amino, mono-substituted amino, di-substituted amino, carboxy, carboalkoxy, alkylcarboxamide, substituted alkylcarboxamide, dialkylcarboxamide, substituted dialkylcarboxamide, alkylsulfonamide, arylsulfonamide, alkylurea, arylurea, alkylcarbamate, arylcarbamate, heteroaryl, haloalkoxy, alkylsulfonyl, alkylsulfinyl, thioalkyl or thiohaloalkyl radicals.

In some embodiments, the bridging A radical can comprise an alkylene or substituted alkylene radical optionally comprising 1, 2, or more heteroatoms selected from O, S and N. The heteroatoms can be substituted for a carbon atom of an alkylene or substituted alkylene. N atoms can be further substituted with a variety of substituent radicals, including hydrogen, alkyl or substituted alkyls.

Examples of bridging "A" radicals having heteroatoms therein include, for example:

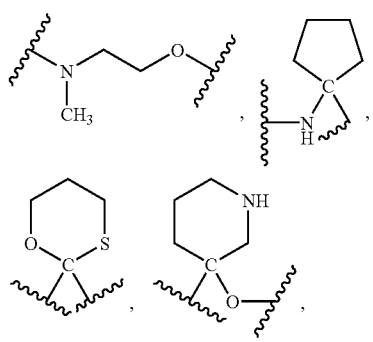

and the like.

In some embodiments, the bridging A radical can comprise O, S, SO, SO$_2$ or N wherein the N is further substituted with hydrogen, alkyl or substituted alkyl. In embodiments when A is an oxygen atom, Ar$_1$ is not an unsubstituted phenyl residue.

The Ar$_1$ radical of the compounds of Formula (I) comprise an aryl or heteroaryl radical. Although not wishing to be bound by theory, it is believed that the Ar$_1$ radical binds to certain relatively hydrophobic and/or nonpolar portions of the protein and/or nuclear receptor sites. Therefore in many embodiments, the Ar$_1$ radicals typically comprise organic moeities and/or radicals that are relatively non-polar and/or relatively hydrophobic, such as, for example, certain aryl or heteroaryl hydrocarbon radicals.

The Ar$_1$ radical comprises an aryl or heteroaryl radical that can be optionally substituted with one or more inorganic or organic substituent radicals. The Ar$_1$ radical can have 1, 2, 3, 4, or 5 substitutent radicals. Suitable substituent radicals include but are not limited to hydrogen, alkyl, substituted alkyl, alkenyl, substituted alkenyl, alkynyl, substituted alkynyl, halogen, cyano, nitro, hydroxyl, acyloxy, alkoxy, substituted alkoxy, acyl, amino, mono-substituted amino, di-substituted amino, carboxy, carboalkoxy, alkylcarboxamide, substituted alkylcarboxamide, dialkylcarboxamide, substituted dialkylcarboxamide, alkylsulfonamide, arylsulfonamide, alkylurea, arylurea, alkylcarbamate, arylcarbamate, heteroaryl, haloalkyl, haloalkoxy, alkylsulfonyl, alkylsulfinyl, thioalkyl or thiohaloalkyl.

Although the substituent radicals for the Ar$_1$ radical (and/or the A, Ar$_2$, R$_1$ and R$_2$ radicals also described herein) can have any number of carbon atoms indicated by the specific definitions elsewhere herein, each such organic substituent radical can have between 1 and 4, or between 5 and 8 carbon atoms. Relatively small substituent radicals having limited numbers of carbons atom, such as for example between 1 and 4 carbon atoms, can be preferred in order to fill the binding sites of the proteins and nuclear receptors without causing physical exclusion of the compounds of the invention from the bindins sites of the target proteins and/or nuclear receptors. Therefore, in some embodiments, the Ar$_1$ radical and any substituents radicals bonded thereto together comprise no more than about 40 carbon atoms, no more than about 35 carbons, or no more than about 30 carbon atoms, no more than about 25 carbons, no more than about 20 carbon atoms or no more than 15 carbon atoms.

In many embodiments, the Ar$_1$ radical is a substituted aryl or heteroaryl radical wherein two substituents thereon, together with the aryl or heteroaryl ring of Ar$_1$ form at least one additional ring radical. Described alternatively, in these embodiments, the Ar$_1$ radical has an aryl or heteroaryl residue fused to at least one additional ring radical, to form a larger fused bicyclic or polycyclic ring radical that may or may not be completely aromatic. Conceptual drawings to illustrate the structure of such fused aryl or heteroaryl Ar$_1$ rings are shown below.

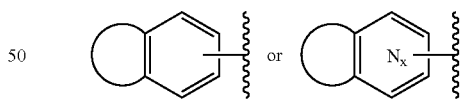

The additional ring radical fused to the aryl or heteroaryl ring of the Ar$_1$ radical can contain between three and five additional carbons, so that the additional ring radical is a five, six, or seven membered ring. The additional ring radical is in many embodiments at least partially saturated, so as to be a non-aromatic ring radical, and can comprise a cycloalkyl, a substituted cycloalkyl, a cycloalkenyl or a substituted cycloalkenyl radical. The additional ring radical can optionally comprise 1 or 2, or more heteroatoms or inorganic radicals, which can include for example O, S, SO, SO$_2$ or N. In these embodiments, the Ar$_1$ residue and/or the additional ring can be optionally further substituted with 1, 2, 3, 4, or 5 substituent radicals for the Ar$_1$ ring, as defined above. Any such N atoms in the additional ring can be further substituted with hydrogen, or substituted or unsubstituted organic radicals, including for example, alkyl or substituted alkyl.

In one embodiment the two substituents bonded to $Ar_1$ are ortho with respect to each other thereby forming a fused ring with $Ar_1$, one specific example of which is shown in Formula (IIIa):

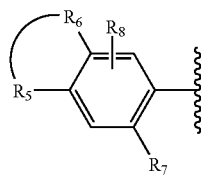

(IIIa)

wherein: $R_5$ and $R_6$ together with the aromatic ring form a cycloalkyl, substituted cycloalkyl, cycloalkenyl or substituted cycloalkenyl ring fused to the aromatic ring, optionally comprising 1, 2 or more heteroatoms or heteroatomic groups that can include O, S, SO, $SO_2$ and N, wherein N is optionally further substituted with groups or radicals that include hydrogen, alkyl or substituted alkyl. $R_7$ and $R_8$ can be independently or together one or more of hydrogen, alkyl, substituted alkyl, alkenyl, substituted alkenyl, alkynyl, substituted alkynyl, halogen, cyano, nitro, hydroxyl, acyloxy, alkoxy, substituted alkoxy, acyl, amino, mono-substituted amino, di-substituted amino, carboxy, carboalkoxy, alkylcarboxamide, substituted alkylcarboxamide, dialkylcarboxamide, substituted dialkylcarboxamide, alkylsulfonamide, arylsulfonamide, alkylurea, arylurea, alkylcarbamate, arylcarbamate, heteroaryl, haloalkyl, haloalkoxy, alkylsulfonyl, alkylsulfinyl, thioalkyl or thiohaloalkyl. In some embodiments, $R_7$ is a lower alkyl, a partially or fully fluorinated lower alkyl, an alkoxy group comprising a lower alkyl or lower fluorinated alkyl, or an amino disubstituted with two lower alkyl groups; and $R_8$ is hydrogen.

In one embodiment related to Formula (III), the additional ring residue formed by $R_5$ and $R_6$ contains between three and five ring atoms, so that the additional ring residue is a five, six, or seven membered ring. The additional ring residue can comprise carbon atoms or 1, 2, or more heteroatoms, or heteroatomic radicals, and the additional ring can be optionally further substituted with additional substituent residues, as disclosed above.

In another embodiment related to Formula (IIIa), $R_5$ and $R_6$ together with the aromatic rind bonded thereto form an indanyl radical of Formula (IIIb):

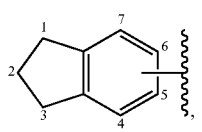

(IIIb)

In yet another embodiment $R_5$ and $R_6$ together with the aromatic ring bonded thereto form a indan-5-yl radical of Formula (IIIc):

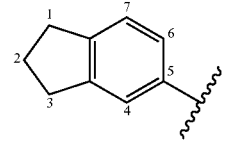

(IIIc)

In one embodiment related to Formula (IIIa), $R_5$ and $R_6$ together with the aromatic ring bonded thereto form a 5,6,7,8-tetrahydronaphthyl radical of Formula (IIId):

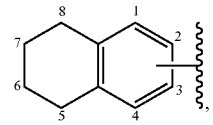

(IIId)

and in another embodiment $R_5$ and $R_6$ together with the aromatic ring bonded thereto form a 5,6,7,8-tetrahydro-2-naphthyl radical of Formula (IIIe):

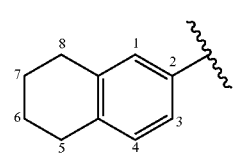

(IIIe)

In another embodiment related to Formula (IIIa), $R_5$ and $R_6$ together with the aromatic ring bonded thereto form a 6,7,8,9-tetrahydro-5H-benzocycloheptenyl radical of Formula (IIIf):

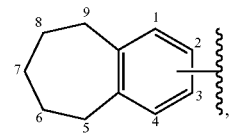

(IIIf)

and in another embodiment $R_5$ and $R_6$ together with the aromatic ring bonded thereto form a 6,7,8,9-tetrahydro-5H-benzocyclohepten-2-yl radical:

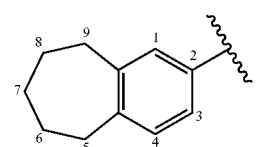

(IIIg)

In any of the radicals of Formulaes (IIIb) through (IIIg) the additional ring can be optionally substituted with one or more of any of the substituent groups or radicals disclosed herein as suitable for $Ar_1$, including alkyl, substituted alkyl, alkenyl, substituted alkenyl, alkynyl, substituted alkynyl, halogen, cyano, nitro, hydroxyl, acyloxy, alkoxy, substituted alkoxy, acyl, amino, mono-substituted amino, di-substituted amino, carboxy, carboalkoxy, alkylcarboxamide, substituted alkylcarboxamide, dialkylcarboxamide, substituted dialkylcarboxamide, alkylsulfonamide, arylsulfonamide, alkylurea, arylurea, alkylcarbamate, arylcarbamate, heteroaryl, haloalkoxy, alkylsulfonyl, alkylsulfinyl, thioalkyl or thiohaloalkyl.

In another embodiment related to Formula (III), $R_5$ and $R_6$ together with the aromatic ring bonded thereto form a 5,6,7,8-tetrahydro-2-napthyl radical substituted with 1, 2, 3 or 4 additional alkyl, substituted alkyl, alkenyl, substituted alkenyl, alkynyl, substituted alkynyl, halogen, cyano, nitro, hydroxyl, acyloxy, alkoxy, substituted alkoxy, acyl, amino, mono-substituted amino, di-substituted amino, carboxy, carboalkoxy, alkylcarboxamide, substituted alkylcarboxamide, dialkylcarboxamide, substituted dialkylcarboxamide, alkylsulfonamide, arylsulfonamide, alkylurea, arylurea, alkylcarbamate, arylcarbamate, heteroaryl, haloalkoxy, alkylsulfonyl, alkylsulfinyl, thioalkyl or thiohaloalkyl residues. In some embodiments, mono- or di-substitution at the 5- and 8-positions of the 5,6,7,8-tetrahydro-2-napthyl radical is favored.

In other embodiments related to Formula (III) $R_5$ and $R_6$ together with the aromatic ring bonded thereto form a cycloalkyl or substituted cycloalkyl, such as a polycyclic radical; wherein $R_7$ is methyl, ethyl, trifluoromethyl, methoxy or dimethylamino; and $R_8$ is hydrogen. Thus, in some exemplary embodiments the polycyclic radical is:

1)

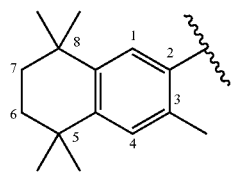

3,5,5,8,8-pentamethyl-5,6,7,8-tetrahydro-2-naphthyl,

2)

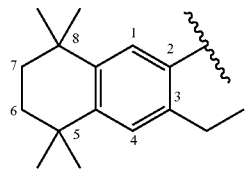

3-ethyl-5,5,8,8-tetramethyl-5 6,7,8-tetrahydro-2-naphthyl,

3)

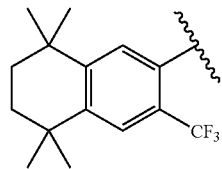

3-trifluoromethyl-5,5,8,8-tetramethyl-5,6,7,8-tetrahydro-2-naphthyl,

4)

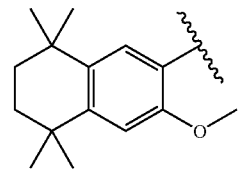

3-methoxy-5,5,8,8-tetramethyl-5,6,7 8-tetrahydro-2-naphthyl, or

5)

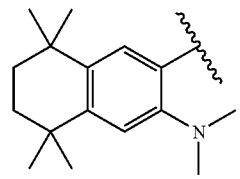

3-dimethylamino-5,5,8,8-tetramethyl-5,6,7,8-tetrahydro-2-naphthyl.

In one embodiment, $R_5$ and $R_6$ together with the $Ar_1$ of Formula (I) form a substituted cycloalkyl to give the 5,5,8,8-tetramethyl-5,6,7,8-tetrahydro-2-naphthyl radical:

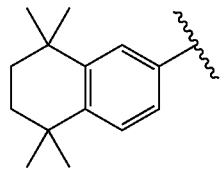

In some embodiments, the additional ring of the bicyclic or polycyclic $Ar_1$ comprises 1, 2, or more nitrogen heteroatoms to give a hetererocycle. One example of such a heterocyclic $Ar_1$ residue is a1-isopropyl-7-methyl-1,2,3,4-tetrahydro-6-quinolinyl radical;

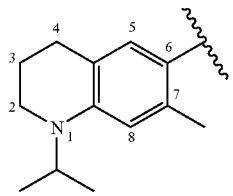

or the 1,4-diisopropyl-6-methyl-1,2,3,4-tetrahydro-7-quinoxalinyl radical:

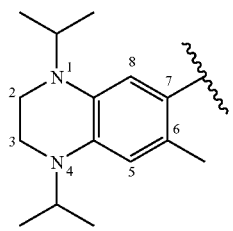

In some embodiments of the present invention, the additional ring fused to the aryl or heteroaryl ring of the $Ar_1$ group can comprise an amide group within the additional ring. The term "amide" as defined hereby and used in the instant specification refers to a functional group or residue that contains a carbonyl (CO) group bound to a nitrogen atom, i.e. a residue having the formula:

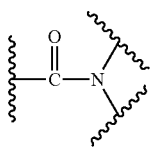

In particular the $Ar_1$ groups, can comprise an additional ring containing at least one amide group as shown by Formulae (205a–b, d–g, and j–k) illustrated below:

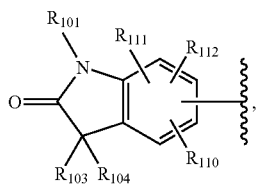
(205a)

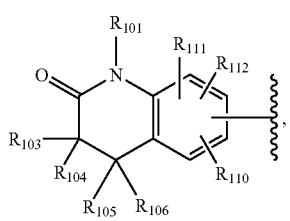
(205b)

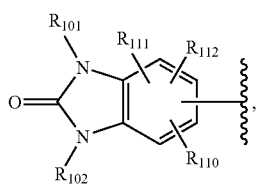
(205d)

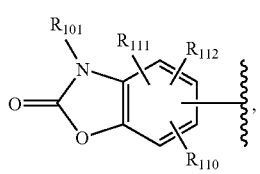
(205e)

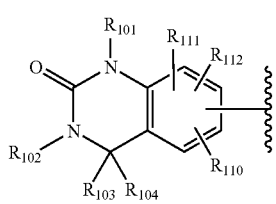
(205f)

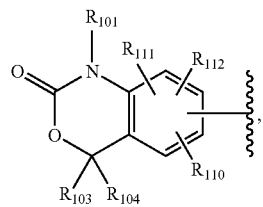
(205g)

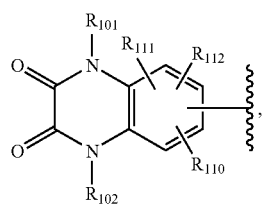
(205j)

or

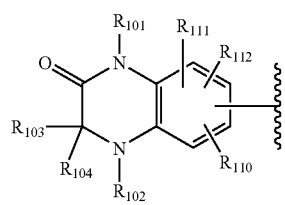
(205k)

wherein $R_{101}$, $R_{102}$, $R_{103}$, $R_{104}$, $R_{105}$ $R_{106}$, $R_{107}$, $R_{108}$, $R_{110}$, $R_{111}$ or $R_{112}$ can be independently selected from inorganic substitutents, which include but are not limited to inorganic substitutents such as hydrogen, halogen, cyano, nitro, hydroxyl, or amino. Alternatively and/or simultaneously, $R_{101}$, $R_{102}$, $R_{103}$, $R_{104}$, $R_{105}$, $R_{106}$, $R_{107}$, $R_{108}$, $R_{110}$, $R_{111}$ or $R_{112}$ can comprise an organic residue having from one to twelve carbon atoms, or from one to six carbons, or from one to four carbons. Examples of suitable organic residues include but are not limited to an alkyl, substituted alkyl, haloalkyl, alkenyl, substituted alkenyl, alkynyl, substituted alkynyl, acyloxy, amino, mono-substituted amino, di-substituted amino, alkylsulfonamide, arylsulfonamide, alkylurea, arylurea, alkylcarbamate, arylcarbamate, aryl, heteroaryl, alkoxy, substituted alkoxy, haloalkoxy, thioalkyl, thiohaloalkyl, carboxy, carboalkoxy, alkylcarboxamide, substituted alkylcarboxamide, dialkylcarboxamide or substituted dialkylcarboxamide residue. In some embodiments, preferred $R_{101}$, $R_{102}$, $R_{103}$, $R_{104}$, $R_{105}$, $R_{106}$, $R_{107}$, $R_{108}$, $R_{110}$, $R_{111}$ or $R_{112}$ groups are an alkyl, substituted alkyl, haloalkyl, alkoxy, substituted alkoxy, or haloalkoxy residues, particularly those comprising from 1 to 6 carbons, or 1 to four carbons.

Some embodiments of the invention relate to $Ar_1$ groups comprising lactam compounds of Formula (206):

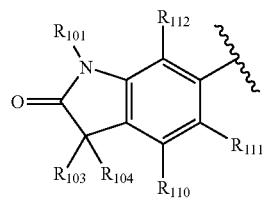
(206)

wherein the R groups are as defined above. In some embodiments of compounds Ar₁ groups of Formula (206), $R_{110}$ and $R_{112}$ are hydrogen, and $R_{101}$, $R_{103}$ and $R_{104}$ are lower alkyl groups.

Some embodiments of the invention relate to six-membered lactam compounds of Formula (207):

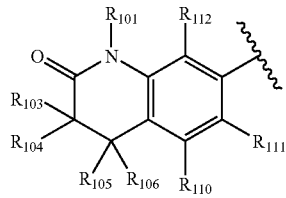
(207)

In some embodiments of compounds having Ar₁ groups of Formula (207), $R_{103}$, $R_{104}$, $R_{110}$, and $R_{112}$ are hydrogen, and $R_{101}$, $R_{105}$ and $R_{106}$ are lower alkyl groups.

Some embodiments of the invention relate to compounds havng Ar₁ groups of Formula (208):

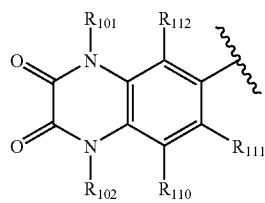
(208)

In some embodiments of compounds having Ar₁ groups of Formula (208), $R_{110}$, and $R_{112}$ are hydrogen, and $R_{101}$ and $R_{102}$ are lower alkyl groups.

In some embodiments $R_{101}$ is hydrogen, alkyl or substituted alkyl. In some examples $R_{101}$ is a straight or branched alkyl of $C_1$-$C_{12}$. In other examples $R_{101}$ is a straight or branched alkyl of $C_1$-$C_8$. In still other examples $R_{101}$ is a straight or branched alkyl of $C_1$-$C_6$. In yet other examples $R_{101}$ is a straight or branched alkyl of $C_1$-$C_4$.

Therefore, in some embodiments, the compounds of the present invention comprise a bicyclic heterocyclic Ar₁ radical having the Formulaes (305a–k):

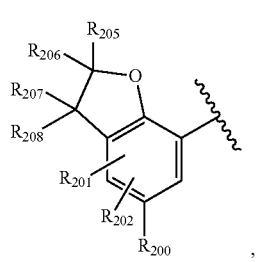
(305a)

-continued

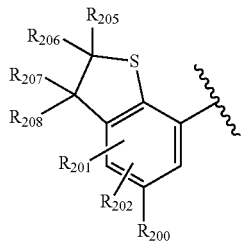
(305b)

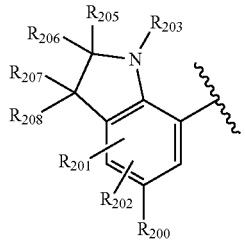
(305c)

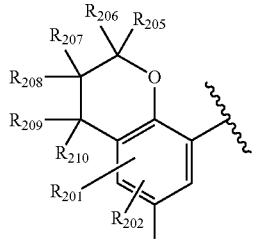
(305d)

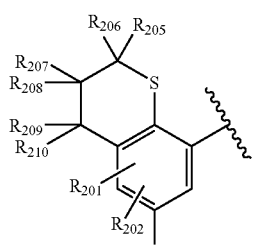
(305e)

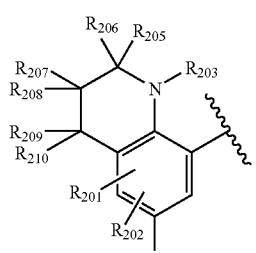
(305f)

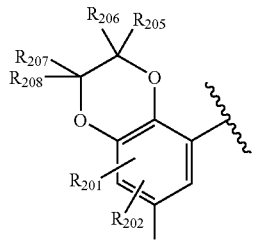
(305g)

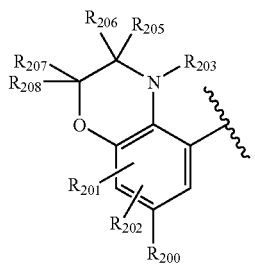

(305h)

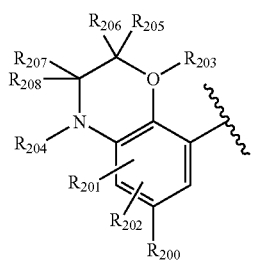

(305i)

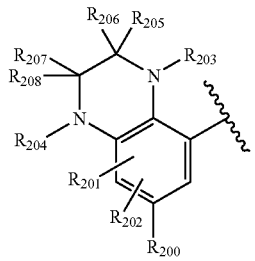

(305j)

, or

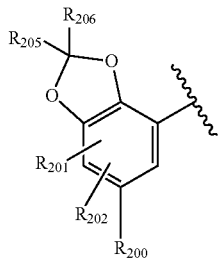

(305k)

wherein
R$_{200}$, R$_{201}$, R$_{202}$, R$_{203}$, R$_{204}$, R$_{205}$, R$_{206}$, R$_{207}$, R$_{208}$, R$_{209}$, and R$_{210}$ can be independently selected from hydrogen, halogen, cyano, nitro, hydroxyl, or an organic substitutent radical having from one to twelve carbon atoms, or one to six carbons, or from one to 4 carbons. Suitable organic substitutent radicals for R$_{200}$, R$_{201}$, R$_{202}$, R$_{203}$, R$_{204}$, R$_{205}$, R$_{206}$, R$_{207}$, R$_{208}$, R$_{209}$, and R$_{210}$ include but are not limited to an alkyl, substituted alkyl, haloalkyl, alkenyl, substituted alkenyl, alkynyl, substituted alkynyl, acyloxy, amino, mono-substituted amino, di-substituted amino, alkylsulfonamide, substituted alkylsulfonamide, arylsulfonamide, heteroaryl-sulfonamide, alkylurea, alkylthiourea, arylurea, acyl, substituted acyl, alkylcarbamate, arylcarbamate, alkylthiocarbamate, substituted alkylthiocarbamate, arylthiocarbamate, heteroaryl, substituted heteroaryl, alkoxy, substituted alkoxy, haloalkoxy, thioalkyl, alkylsulfoxide, alkylsulfonyl, thiohaloalkyl, carboxy, carboalkoxy, alkylcarboxamide, substituted alkylcarboxamide, dialkylcarboxamide or substituted dialkylcarboxamide radicals. In some embodiments of the Ar$_1$ groups of Formulaes (305a–k), R$_{200}$ is an organic substitutent radical having from one to twelve carbon atoms, and R$_{201}$ and R$_{202}$ are hydrogen or halogen.

Some embodiments of the Ar$_1$ groups of the invention relate to compounds having an Ar$_1$ group of Formula (306):

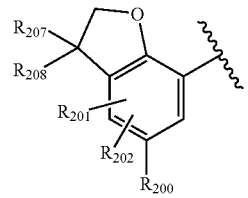

(306)

wherein:

R$_{200}$ can be hydrogen, alkyl, substituted alkyl, haloalkyl, alkenyl, substituted alkenyl, alkynyl, substituted alkynyl, halogen, cyano, nitro, hydroxyl, acyloxy, amino, mono-substituted amino, di-substituted amino, alkylsulfonamide, substituted alkylsulfonamide, arylsulfonamide, heteroaryl-sulfonamide, alkylurea, alkylthiourea, arylurea, acyl, substituted acyl, alkylcarbamate, arylcarbamate, alkylthiocarbamate, substituted alkylthiocarbamate, arylthiocarbamate, heteroaryl, substituted heteroaryl, alkoxy, substituted alkoxy, haloalkoxy, thioalkyl, alkylsulfoxide, alkylsulfonyl, thiohaloalkyl, carboxy, carboalkoxy, alkylcarboxamide, substituted alkylcarboxamide, dialkylcarboxamide or substituted dialkylcarboxamide. In some embodiments, R$_{200}$ is an organic substitutent radical having from one to twelve carbon atoms, R$_{201}$ and R$_{202}$ are hydrogen or halogen; and R$_{207}$ and R$_{208}$ are independently or together alkyl or substituted alkyl.

Certain similar embodiments of the Ar$_1$ groups of the invention have Formulas (307) and (308):

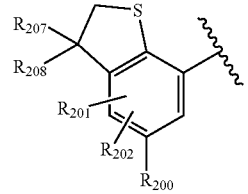

(307)

or

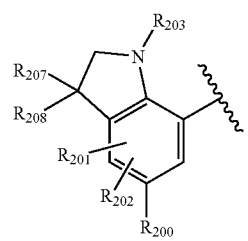

(308)

wherein R$_{200}$, R$_{201}$, R$_{202}$, R$_{207}$ and R$_{208}$ are as described above with respect to the compounds of formula (306).

In some embodiments, nitrogen is present in the aryl ring of the bicyclic Ar$_1$ group, to form a substituted or unsubstituted heteroaryl form a bicyclic pyridine ring system. Examples of such bicyclic pyridine include but are not limited to Formulaes (305l–m):

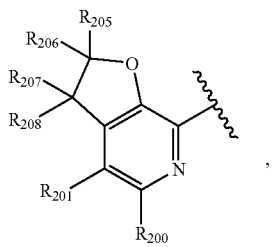
(305l)

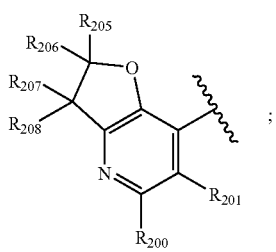
(305m)

where $R_{200}$, $R_{201}$, $R_{205}$, $R_{206}$, $R_{207}$ and $R_{208}$ have the same meaning as described hereinabove. Alternatively, the heteroaryl ring could comprise residues having two nitrogen atoms. An example of such a compound is shown below.

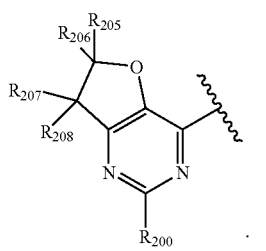
(305l)

In some embodiments of the invention, $Ar_1$ is not a fused ring radical as in the embodiments described above, but rather has only one a phenyl or pyridyl radical which is substituted with at least 1, and optionally at least 2, 3, 4, or 5 substituent radicals, selected from the substituent radicals taught hereinabove for the $Ar_1$ radical. In such embodiments wherein there is only 1 substituent radical, the substitutent radicals include alkyl radicals having 5 or more carbons, such as higher alkyl groups, but do not include lower $C_1$–$C_4$ groups. Stated alternatively, in some embodiments $Ar_1$ is not a $C_1$–$C_4$ alkylphenyl. In embodiments wherein n=0, $Ar_1$ is not a radical of the following formula:

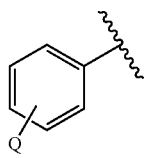

wherein Q is hydrogen, $C_1$–$C_4$ alkyl, alkoxy, thio or $C_1$–$C_4$ thioalkyl.

The $Ar_2$ radical of the compounds of Formula (I) is a substituted or unsubstituted aryl radical or a substituted or unsubstituted heteroaryl radical. The aryl rings of $Ar_2$ radical of the invention can include phenyl rings and napthyl rings. Further examples of heteroaryl radicals suitable for the practice of the invention are disclosed in Example 11, and the "B" component precursors for the $Ar_2$ ring disclosed therein.

The $Ar_2$ radical of the compounds of the invention often comprises an aryl or heteroaryl radical optionally substituted with 1, 2, or more inorganic or organic substituent groups or radicals. Suitable substituent groups or radicals for the $Ar_2$ ring include but are not limited to hydrogen, alkyl, substituted alkyl, alkenyl, substituted alkenyl, alkynyl, substituted alkynyl, halogen, cyano, nitro, hydroxyl, acyloxy, alkoxy, substituted alkoxy, hydroxyl, acyl, amino, mono-substituted amino, di-substituted amino, carboxy, carboalkoxy, alkylcarboxamide, substituted alkylcarboxamide, dialkylcarboxamide, substituted dialkylcarboxamide, alkylsulfonamide, arylsulfonamide, alkylurea, arylurea, alkylcarbamate, arylcarbamate, heteroaryl, alkoxy, substituted alkoxy, haloalkoxy, alkylsulfonyl, alkylsulfinyl, thioalkyl or thiohaloalkyl radicals. In some embodiments, the substituent radicals for the Ar2 radical comprise less than four carbon atoms.

In another embodiment of the invention $Ar_2$ is one of the following formulas:

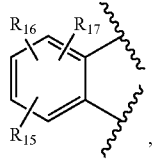
(IVa)

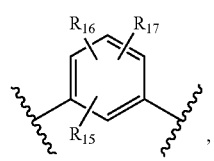
(IVb)

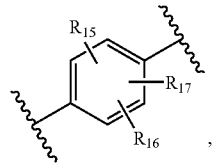
(IVc)

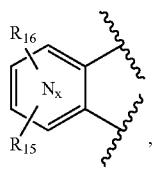
(Va)

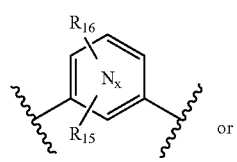
(Vb)

or

-continued (Vc)

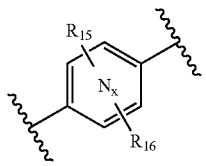

wherein $R_{15}$, $R_{16}$ and $R_{17}$ are independently or together hydrogen, alkyl, substituted alkyl, alkenyl, substituted alkenyl, alkynyl, substituted alkynyl, halogen, cyano, nitro, hydroxyl, acyloxy, alkoxy, substituted alkoxy, acyl, amino, mono-substituted amino, di-substituted amino, carboxy, carboalkoxy, alkylcarboxamide, substituted alkylcarboxamide, dialkylcarboxamide, substituted dialkylcarboxamide, alkylsulfonamide, arylsulfonamide, alkylurea, arylurea, alkylcarbamate, arylcarbamate, heteroaryl, haloalkoxy, alkylsulfonyl, alkylsulfinyl, thioalkyl or thiohaloalkyl.

Formulaes (Va), (Vb) and (Vc) represent different heteroaryl radicals for $Ar_2$ containing nitrogen, wherein one, two, or more ring nitrogens are present (i.e. x can be 1, 2, 3, 4, or 5, and N can be at any position, although in many embodiments the N atom is not directly bonded to the $Ar_1$ or methylene or methine residues of Formula 1. By way of example, when one ring nitrogen is present in Formula (Vb) the following structures are within the scope of the invention:

(VIa)

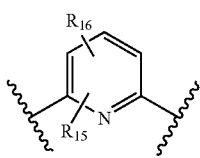

(VIb)

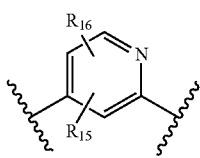

or (VIc)

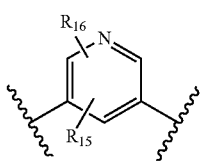

Similarly, when two ring nitrogens are present in Formula (Vb) the following structures are within the scope of the invention:

(VIIa)

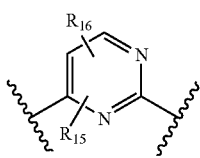

-continued (VIIb)

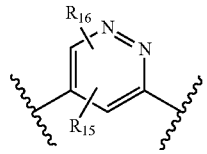

(VIIc)

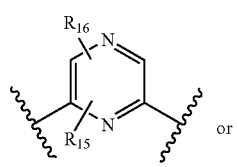

or (VIId)

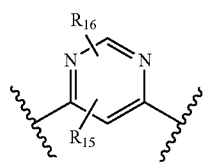

and $R_{15}$ and $R_{16}$ have the same definition as above.

The $Ar_2$ radicals can also comprise a variety of other known heteroaryl ring residues, which can have any stable ring geometry of attachment to the $Ar_1$ and methylene or methine residues of Formula 1, and can be either substituted or unsubstituted with one or more additional substituent groups or residues as taught hereinabove for $Ar_2$ radicals. Examples of such heteroaryl ring residues include but are not limited to the examples of Example 11.

It is understood that the Formulaes disclosed herein are general structures and where applicable can represent more than one bonding orientation with respect to other radicals present in Formula (I) and other embodiments disclosed herein, such as, for example, Formula (VIIa), can represent either Formula (VIIIa) or Formula (VIIIb):

(VIIIa)

(VIIIb)

wherein $Ar_1$, A, n, $R_1$, $R_2$, $R_{15}$, $R_{16}$, W and X have the same meaning as defined herein.

The N-substituted heterocyclic ring of the compounds of Formula (I) have the structure:

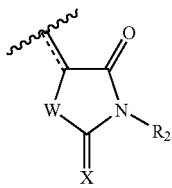

wherein W is —S—, —O— or —N—R₃, and X is O or S; wherein R₃ is hydrogen, or a substituted or unsubstituted radical comprising from one to 12 carbon atoms.

Some embodiments of the invention relate to Formula (I) wherein W is —S—, —O— or N—R₃, wherein R₃ is as defined herein, and X is O, so as to give N-substituted heterocycles of the following Formulae:

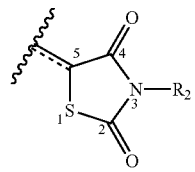 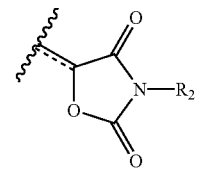

N-substituted-
Thiazolidine-2,4-dione

N-substituted-
Oxazolidine-2,4-dione

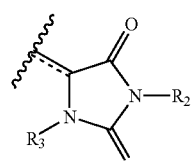

di-N-substituted-
Imidazolidine-2,4-dione

Some embodiments of the invention relate to Formula (I) where W is —S—, —O— or N—R₃, wherein R₃ is as defined herein, and X is S, so as to give N-substituted heterocycles of the following Formulae:

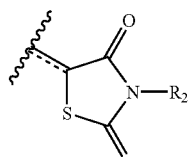 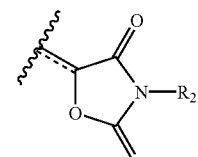

N-substituted-
2-Thioxo-thiazolidine-4-dione

N-substituted-
2-Thioxo-oxazolidin-4-dione

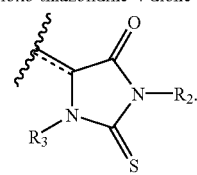

N-substituted-
2-Thioxo-imidazolidin-4-dione

Some embodiments of the invention relate to Formula (I) where W is —S— and X is S to give N-substituted heterocycles of the following Formula:

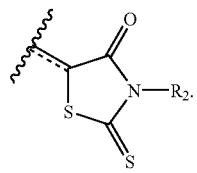

N-substituted-
2-Thioxo-thiazolidin-4-dione

Some embodiments of the invention relate to Formula (I) where W is —S— and X is O to give N-substituted heterocycles of the following Formula:

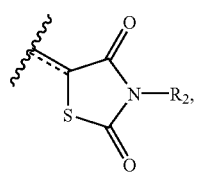

N-substituted-
Thiazolidine-2,4-dione

In certain embodiments, invention includes a genus of compounds of the Formula:

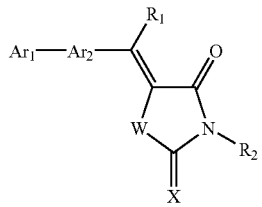

wherein

Ar₁ comprises an aryl radical fused to at least one additional ring radical to form a fused bicyclic ring radical, wherein the additional ring radical has at least two substituent radicals having from 1 to four carbon atoms;

Ar₂ is a substituted or unsubstituted benzene, naphthalene, or pyridine radical;

R₁ is hydrogen, a lower alkyl radical;

R₂ is a substituted or unsubstituted organic radical having 1 to 12 carbon atoms;

W is —S—, —O— or —N—R₃ wherein R₃ is hydrogen, or a substituted or unsubstituted radical comprising from one to 12 carbon atoms; and X is O or S;

or a pharmaceutically acceptable salt thereof.

In other embodiments, invention includes a genus of compounds of the Formula:

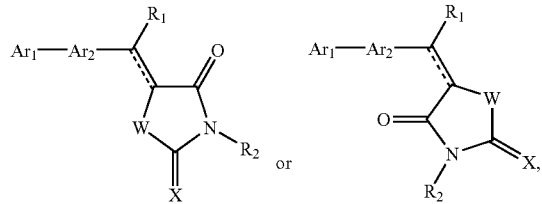

wherein,

"- - -" is absent or present;

Ar₁ has the formula

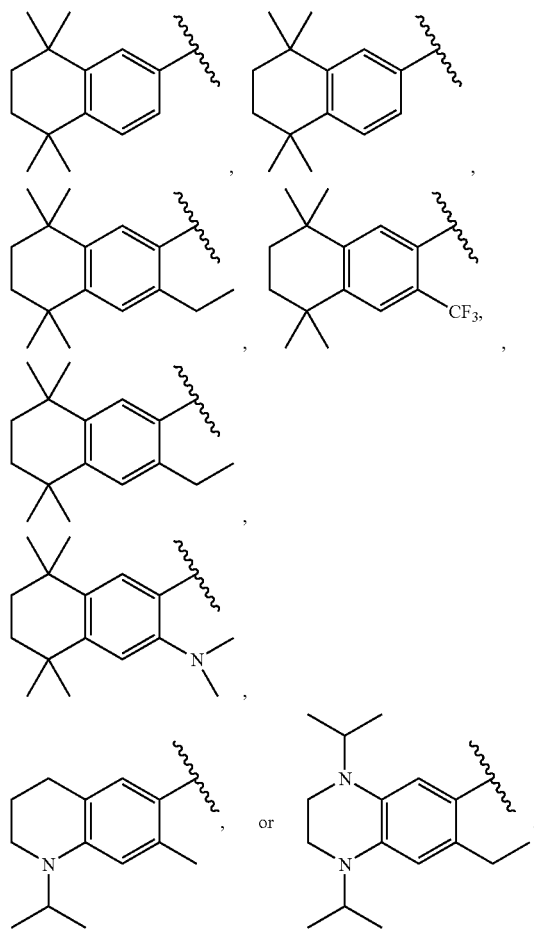

Ar₂ has the formula

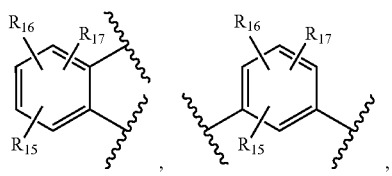

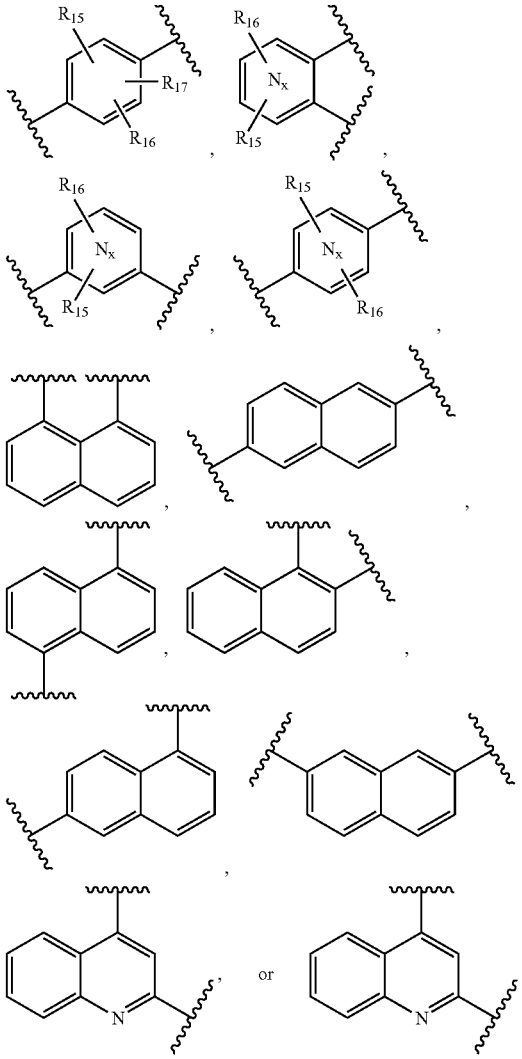

wherein x is one or two, and $R_{15}$, $R_{16}$ and $R_{17}$ are independently selected from hydrogen, halogen, cyano, nitro, hydroxyl, amino, or an organic radicals comprising one to four carbon atoms selected from an alkyl, substituted alkyl, haloalkyl, haloalkoxy, alkoxy, substituted alkoxy, mono-substituted amino, di-substituted amino having from one to four carbon atoms.

$R_1$ is hydrogen, or an alkyl or substituted alkyl group having one to four carbon atoms;

$R_2$ is a an alkyl or substituted alkyl group having one to four carbon atoms,

W is —S—; and

X is O or S;

or a pharmaceutically acceptable salt thereof.

Some of the compounds disclosed herein can form solvates with water or with common organic solvents. Such solvates are embraced within the scope of the invention.

The invention includes within its scope pharmaceutically acceptable salts of the compounds of the invention, particularly where a basic or acidic group is present in a compound according to the invention therein. For example, when an acid substituent, such as a carboxylic acid (i.e., —COOH), is present, then a basic salt, such as ammonium, amine (e.g., tris(hydroxymethyl)aminomethane, diethylamine, t-butylamine and the like), sodium, potassium, calcium, alkaline earth metals, and trivalent salts, such as aluminum and like salts, are contemplated and within the scope of the invention. When a basic group (such as amino or a basic heteroaryl radical, such as pyridyl) is present, then an acidic salt, such as hydrochloride, hydrobromide, acetate, maleate, phosphate, methanesulfonate, and the like is contemplated and within the scope of the invention. The only constraint with respect to the selection of the salt is that it should not unacceptably increase the toxicity.

The present invention provides, but is not limited to, the specific compounds set forth in the Examples as well as those set forth below, or pharmaceutically acceptable salts thereof. One example of such specific compounds is {5-[3-t-Butyl-4-methoxyphenyl)-6-ethoxy-benzylidene]-4-oxo-2-thioxo-thiazolidin-3-yl}-acetic acid, also referred to as Compound 67 herein:

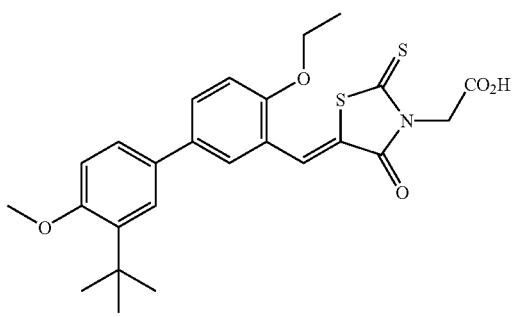

Making the Compounds

Figure 4:
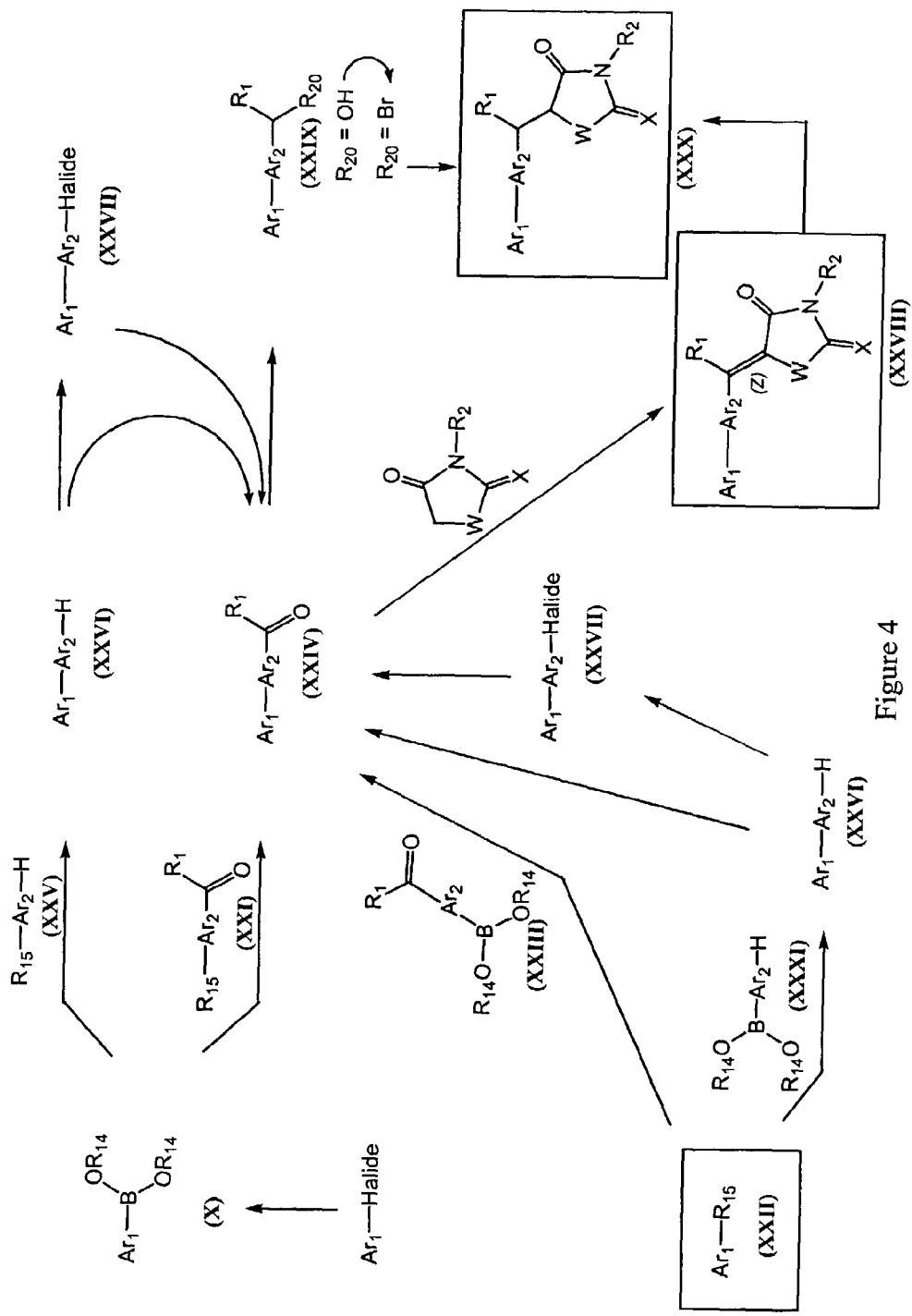
FIG. 4 shows representative examples of methods for the synthesis of compounds disclosed herein.

Various synthetic methods can be employed by those of skill in the art for the production of the compounds and intermediates disclosed herein. For example, the many known methods of organic chemistry can be employed to provide precursor carbonyl compounds as shown below,

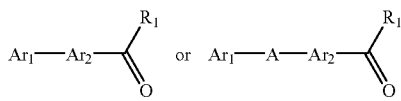

wherein $Ar_1$, $Ar_2$, A and/or $R_1$ can be as described in any of the embodiments herein. These precursor carbonyl compounds could be prepared, for example, by acylation of the corresponding aromatic compounds, or other alternative methods. The precursor carbonyl compounds could then be condensed with a heterocycle, or a heterocyclic derivative thereof, to provide the desired compounds of the invention, for example, a representative set of synthetic pathways are shown in FIG. 4 when n=0 (i.e no bridging A group is present). One method, for example, includes coupling a boronic acid of Formula (X), $R_{14}$=H, with a carbonyl-containing aryl halide of Formula (XXI), such as, $R_{15}$=Br, to give biaryl (XXIV) that is substituted with a carbonyl group, such as, for example, a formyl group (i.e., $R_1$=H). Alternatively, boronic acid (X) can be coupled with aryl bromide (XXV), $R_{15}$=Br, to give biaryl (XXVI) that is subsequently formylated using techniques known in the art, such as the Vilsmeier or the Vilsmeier-Haack reaction, the Gatterman reaction, the Duff reaction, the Reimer-Tiemann reaction or a like reaction. Coupling reactions such as that described for the formation of Biaryl (XXIV) and (XXVI) can also be conducted using boronic esters, such as where $R_{14}$ together with the boron form a pinacol borate ester (formation of pinacol esters: Ishiyama, T., et al., *J. Org. Chem.* 1995, 60, 7508–7510, Ishiyama, T., et al., *Tetrahedron Letters* 1997, 38, 3447–3450; coupling pinacol esters: Firooznia, F. et al., *Tetrahedron Letters* 1999, 40, 213–216, Manickam, G. et al., *Synthesis* 2000, 442–446; all four citations encorporated herein by reference). In addition, $R_{15}$ can also be I, Cl or triflate (derived from a phenol). Biaryl (XXVI) can also be acylated, for example by the Friedel-Crafts Acylation reaction or the like. In one embodiment, the biaryl (XXVI) is formylated. Alternatively, in a two step manner, biaryl (XXVI) is formylated by first performing a halogenation step to give biaryl (XXVII), such as a bromination, followed by a halogen-metal exchange reaction using an alkyl lithium and reaction with DMF or equivalent known in the art to give biaryl (XXIV) where $R_1$ is H. The carbonyl group of biaryl (XXIV) can subsequently be condensed with a heterocycle or heterocyclic derivative thereof to give biaryl (XXVIII). In one embodiment the heterocycle coupled is an N-substituted heterocycle of the Formula:

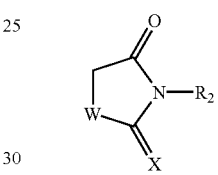

wherein: W, X, and $R_2$ have the same meaning as described herein.

In another embodiment the heterocycle coupled to (XXIV) is not initially N-substituted, and has the Formula:

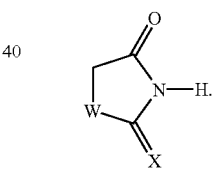

The "N" substituent group is then attached to the nitrogen atom of the heterocycle via known procedures, which include, for example, alkylation with an alkyl halide. In still another embodiment, is when W and X are S, and $R_2$ is —$CH_2CO_2H$, this heterocyclic is known in the art as, "rhodanine acetic" or "rhodanine-3-acetic acid."

In an alternative manner, the coupling can take place between aryl (XXII), such as, for example, where $R_{15}$=Br, and boronic acid (XXIII, $R_{14}$=H) to give the above mention biaryl (XXIV). Also aryl (XXII) can be coupled with boronic acid (XXXI) to give biaryl (XXVI). Employing the same strategy as described above biaryl (XXVI) can be either formylated or acylated to achieve biaryl (XXIV).

Aryl (X) can be readily produced by reaction of $Ar_1$-Halide, such as bromide, with an alkyl lithium to give the $Ar_1$-lithium that is subsequently allowed to react with a borate ester and hydrolyzed to give aryl (X) wherein $R_{14}$ is hydrogen. In another method, aryl (X) can be prepared by reacting $Ar_1$-Triflate with a pinacoldiboron in the presence of a palladium catalyst with an appropriate ligand, such as, dppf, to give the corresponding aryl (X) wherein the two $R_{14}$ groups together with the boron form a pinacol ester. In another embodiment, aryl (XXIII) can be readily obtained by first protecting the carbonyl group using methods known in the art, such as, for example, an acetal or ketal, and then reacting the halide, such as a bromide, with an alkyl lithium to give the $Ar_2$-lithium that is subsequently allowed to react with a borate ester and hydrolyzed to deprotect the carbonyl group and give aryl (XXIII) wherein $R_{14}$ is hydrogen. In another method, aryl (XXIII) can be prepared without protection of the carbonyl group by reacting $Ar_2$-Triflate with a pinacoldiboron in the presence of a palladium catalyst with an appropriate ligand, such as, dppf, to give the corresponding aryl (XXIII) wherein the two $R_{14}$ groups together with the boron form a pinacol ester.

Figure 6:
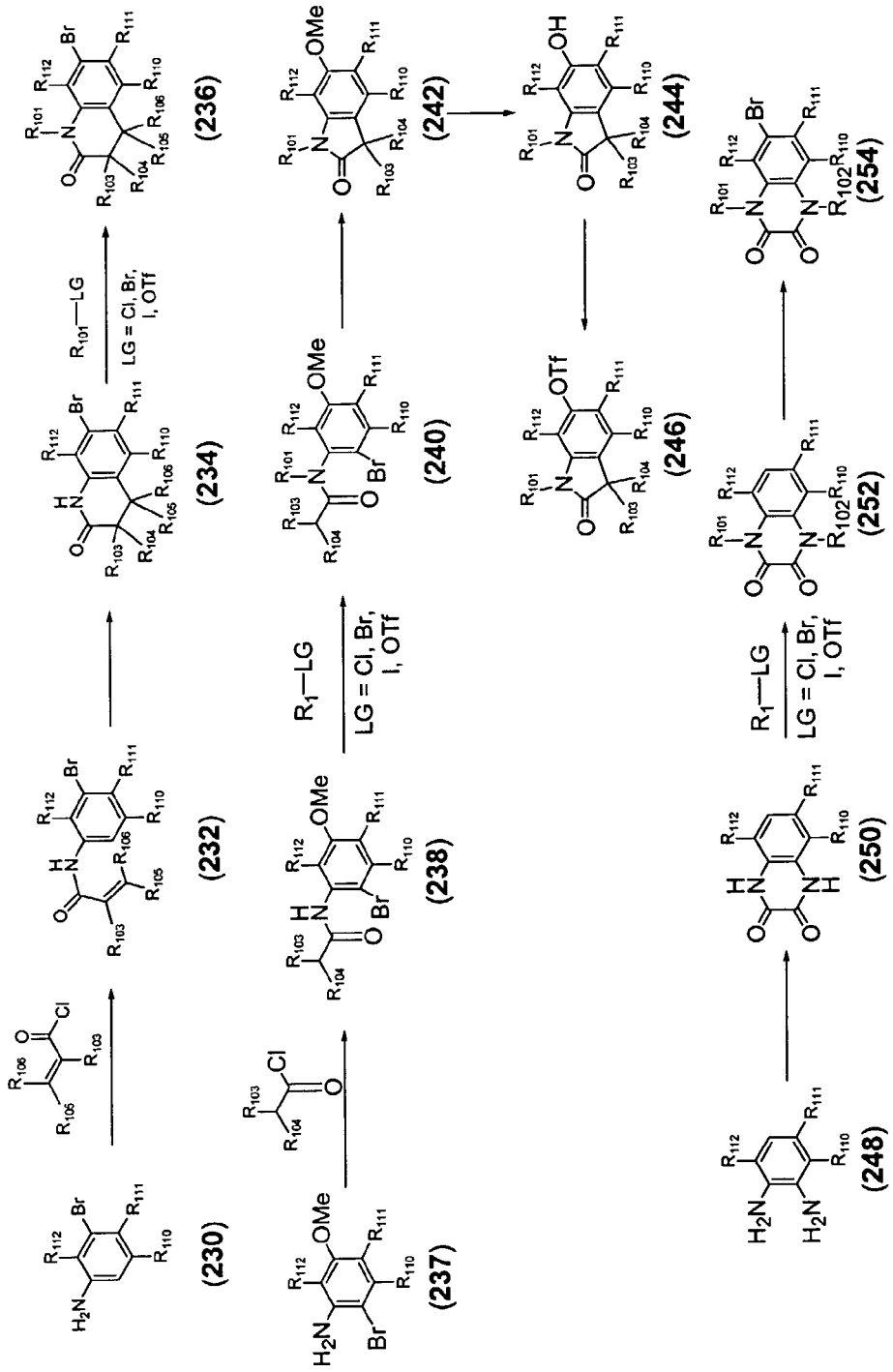
FIG. 6 shows methods for synthesizing synthetic precursors of certain amide compounds disclosed herein.

Various synthetic methods can be employed in the making the various precursors of the compounds disclosed herein. A reprentative set of synthetic pathways is shown in FIG. 6 for making precursors of the $Ar_1$ group that comprise an amide group having Formulas (205–208), that can be used in the coupling with $Ar_2$ and subsequently to the compounds of the invention. One method shown in FIG. 6, for example, includes the use of aniline (230) that can be coupled with an acid chloride to give amide (232). The groups $R_{103}R_{105}R_{106}$ can be introduced into compounds of the invention by the selection of the appropriate acid chloride. Amide (232) can also be prepared by methods known in the art utilizing a carboxylic acid and a coupling agent such as, for example, a carbodiimide. The amide (232) is converted to 2-oxo-1,2,3,4-tetrahydro-quinoline (234) through a Lewis Acid cyclization. One Lewis acid that can be utilized in the process is, for example, $AlCl_3$. Mineral acids can effect the same cyclization. At this stage $R_{101}$ can be introduced to give 2-oxo-1,2,3,4-tetrahydro-quinoline (236) by allowing $R_1$-LG, wherein LG is a leaving group, such as, for example, Cl, Br, I, OTf, and the like, to react with the nitrogen anion of 2-oxo-1,2,3,4-tetrahydro-quinoline (234). The anion of 2-oxo-1,2,3,4-tetrahydro-quinoline (234) can be generated using a base such as, for example, KOH/DMSO, NaH and the like.

Another method, for example, includes the use of aniline (237) that can be coupled with an acid chloride to give amide (238). The groups $R_{103}R_{104}$ can be introduced into compounds of the invention by the selection of the appropriate acid chloride. Amide (238) can also be prepared by methods known in the art utilizing a carboxylic acid and a coupling agent such as, for example, a carbodiimide. At this stage $R_{101}$ can be introduced to give amide (240) by allowing $R_{101}$-LG to react with the nitrogen anion of amide (238), wherein LG is a leaving group, such as, for example, Cl, Br, I, OTf, and the like. 2-oxo-2,3-dihydro-1H-indole (242) can be prepared from amide (240) through a Pd-assisted cyclization. Various ligands with Pd can be employed, such as, for example, tricyclohexyl-phosphine. The methoxy of amide (242) can be convert to phenol (244) using a variety of methods known in the art, such as, for example, $BBr_3$. The resulting phenol (244) can be converted into triflate (246), or the like, using triflic anhydride or similar reagent that is suitable for coupling with $Ar_6$.

Another method, for example, includes the use of phenylene diamine (248) that can be condensed with oxylyl chloride to give quinoxaline-2,3-dione (250). $R_{101}$ can be introduced by allowing $R_{101}$-LG to react with the nitrogen anion of quinoxaline-2,3-dione (250), wherein LG is a leaving group, such as, for example, Cl, Br, I, OTf, and the like. $R_{102}$ can be introduced by allowing $R_{102}$-LG to react with the nitrogen anion of quinoxaline-2,3-dione (250), wherein LG is a leaving group, such as, for example, Cl, Br, I, OTf, and the like. $R_{101}$ and $R_{102}$ can be the same or different. Quinoxaline-2,3-dione (252) can be brominated to give quinoxaline-2,3-dione (254) using methods known in the art, such as, for example, $Br_2$ or equivalent, in an appropriate solvent, such as acetic acid. Bromination might also be carried out prior to the introduction of $R_{101}$ and $R_{102}$.

Figure 7:
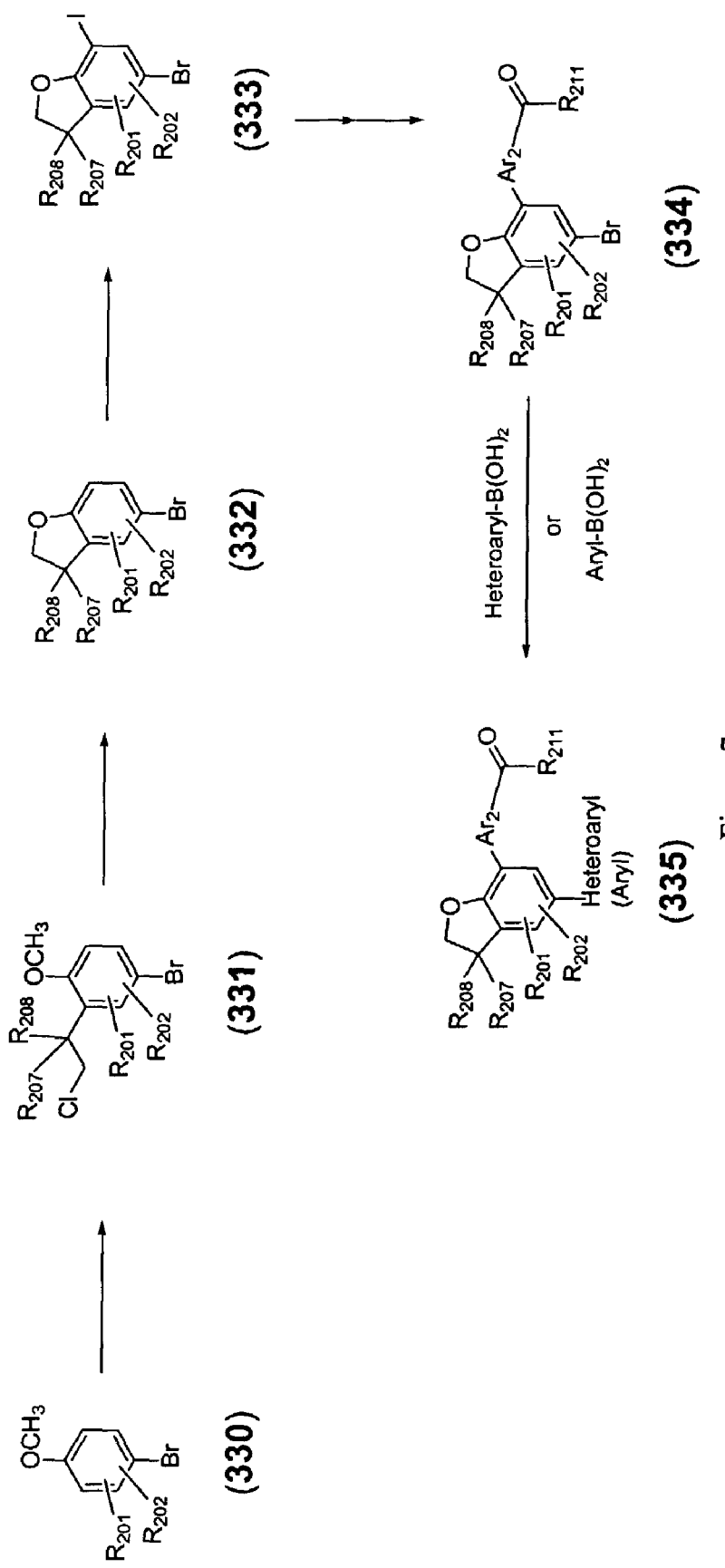
FIG. 7 shows methods for synthesizing synthetic precursors of certain ether compounds disclosed herein.

A reprentative set of synthetic pathways is shown in FIGS. 7–10 for the making of precursors for the $Ar_1$ group that can be used in the coupling with $Ar_2$ and subsequently to the compounds of the invention. One method, for example as shown in FIG. 7, includes the use of anisole (330) that can be alkylated with, for example, 3-chloro-2-methyl-propene, to give anisole (331). By selecting the desired chloropropene the groups $R_{207}R_{208}$ can be introduced into compounds of the invention. Anisole (231) is subsequently cyclized in the presence of pyridine hydrochloride and quinoline with heat to give the dihydro-benzofuran (332). The dihydro-benzofuran (332) can be iodinated to compound (333) and subsequently coupled using methods described below herein to give biaryl (334). Different groups can be introduced at this stage in the synthesis. For example, biaryl (334) can undergo another coupling reaction, such as a Suzuki coupling reaction and other methods described herein below, to give biaryl (335) wherein different heteroaryls or aryl groups can be introduced as shown in FIG. 7.

Figure 8:
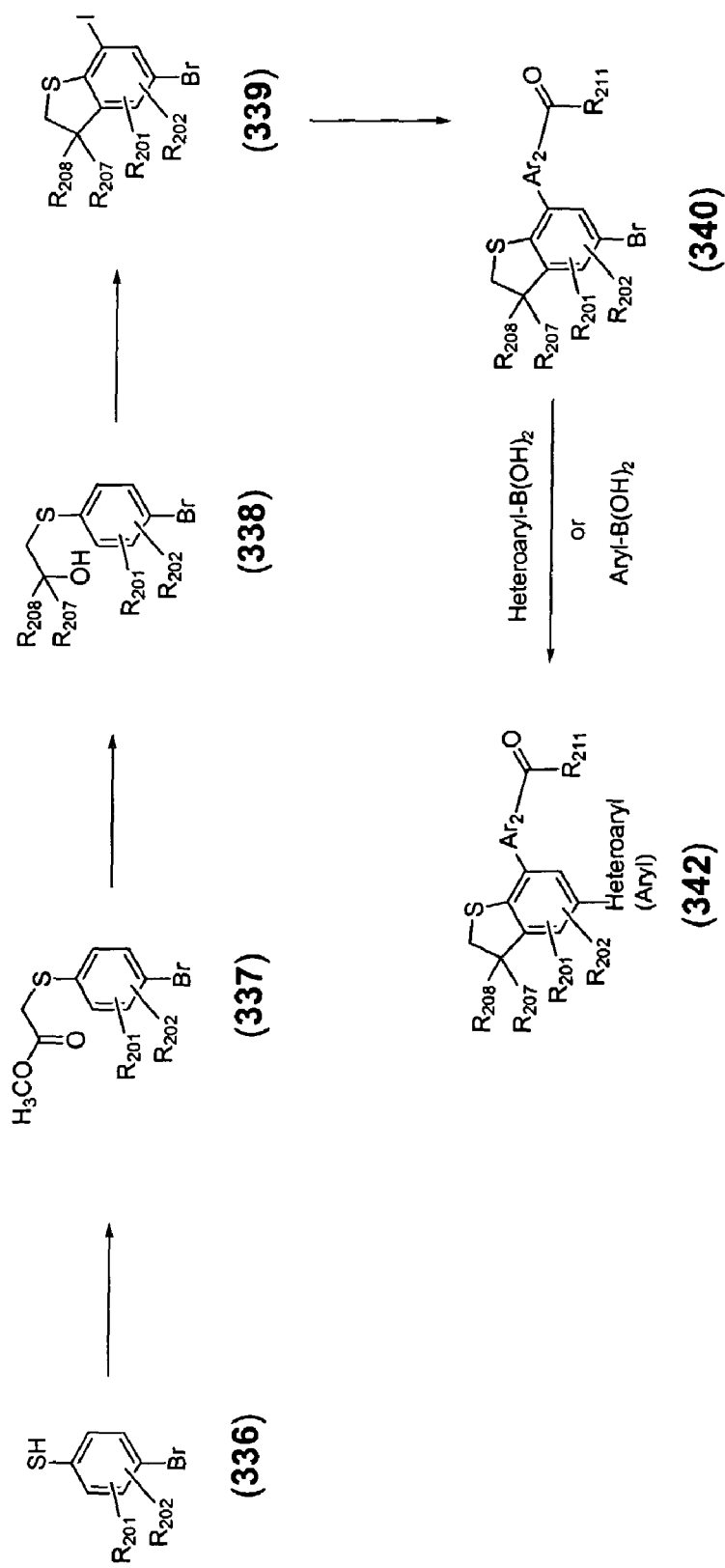
FIG. 8 shows methods for synthesizing synthetic precursors of certain thioether compounds disclosed herein.

Another method, for example shown in FIG. 8, includes the use of aryl thiol (336) that can be alkylated with an alpha-halo actate to give ester (337). The ester can be converted to a 3° alcohol (338) by methods known in the art, such as through a Grignard reagent. The groups $R_{207}R_{208}$ can be introduced into compounds of the invention by the selection of the appropriate Grignard. Alcohol (338) is cyclized using, for example, a Lewis acid, such as $AlCl_3$, to give dihydro-benzothiophene (339). In a similar manner as described above herein, dihydro-benzothiophene (339) is converted to biaryl (340) and is subsequently modified to biaryl (342). Coupling reactions to biaryls wherein a sulfur is present in the molecule can provide difficulties with certain catalyses. However, there are various procedures in the art that allow such couplings in the presence of a sulfur atom, such as, Cram, et al., *J. Org. Chem.* 55:4622–4634 (1990) and Savarin, et al., *Org. Letters* 3:2149–2152 (2001).

Figure 9:
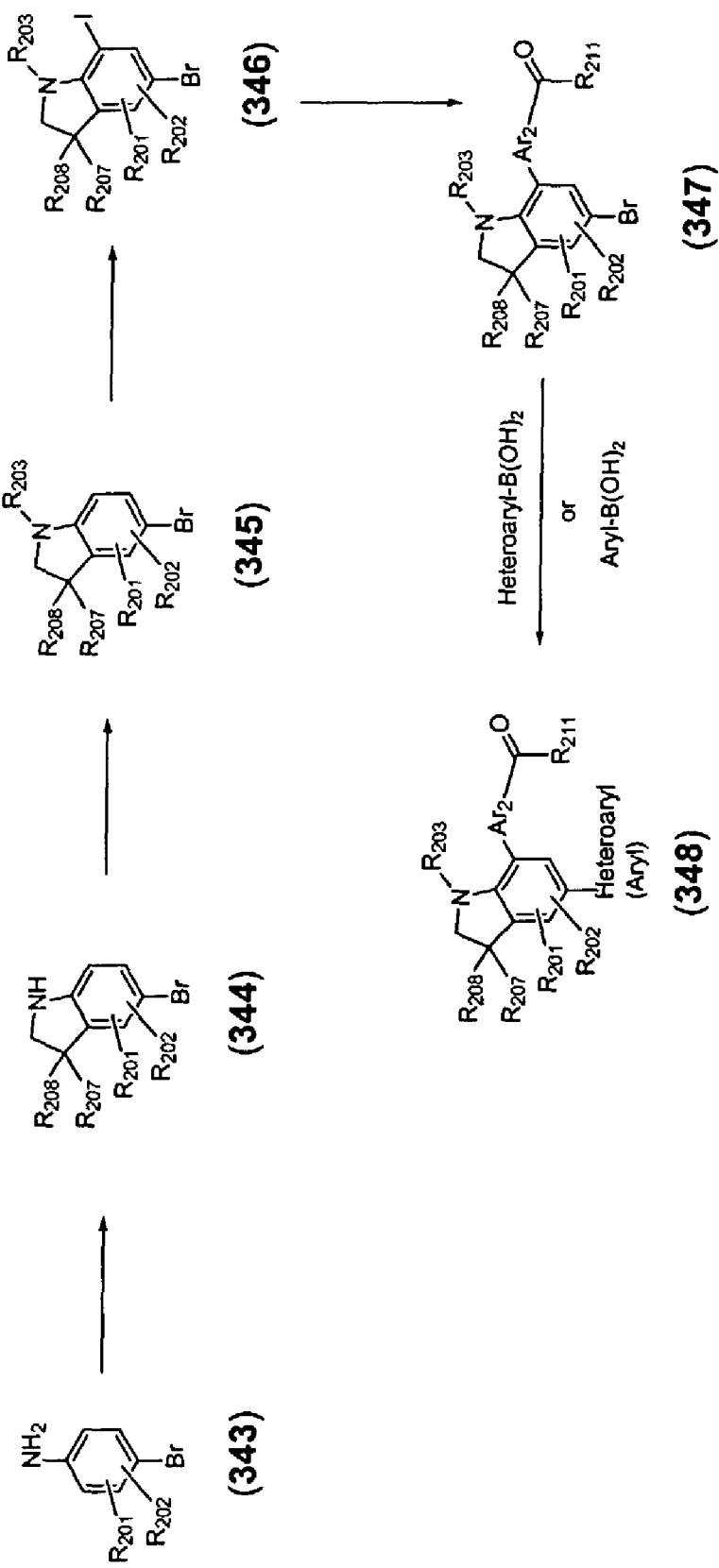
FIG. 9 shows methods for synthesizing synthetic precursors of certain amine compounds disclosed herein.

Another method, for example shown in FIG. 9, includes the use of aniline (343) that can be cyclized in a similar manner as described by Kraus, et al. *Tetrahedron Letters* 40:2039–2040 (1999) to give dihydro-indole (344). At this stage, $R_{203}$ can be introduced by allowing $R_{203}$-LG to react with the nitrogen anion of dihydro-indole (344), wherein LG is a leaving group, such as, for example, Cl, Br, I, OTf, and the like to give dihydro-indole (345). Dihydro-indole (345) can be iodinated to give dihydro-indole (346) and using methods described herein above dihydro-indole (346) is converted to biaryl (347) and subsequently into aryl or heteroaryl modified biaryl (348). It will be appreciated that biaryls (334), (340) and (347) can be converted into a boron derivative, such as a boron ester or boronic acid, and subsequently coupled with an aryl or heteroaryl halide to give the corresponding coupled biaryl (335), (342) and (348) respectively.

Figure 10:
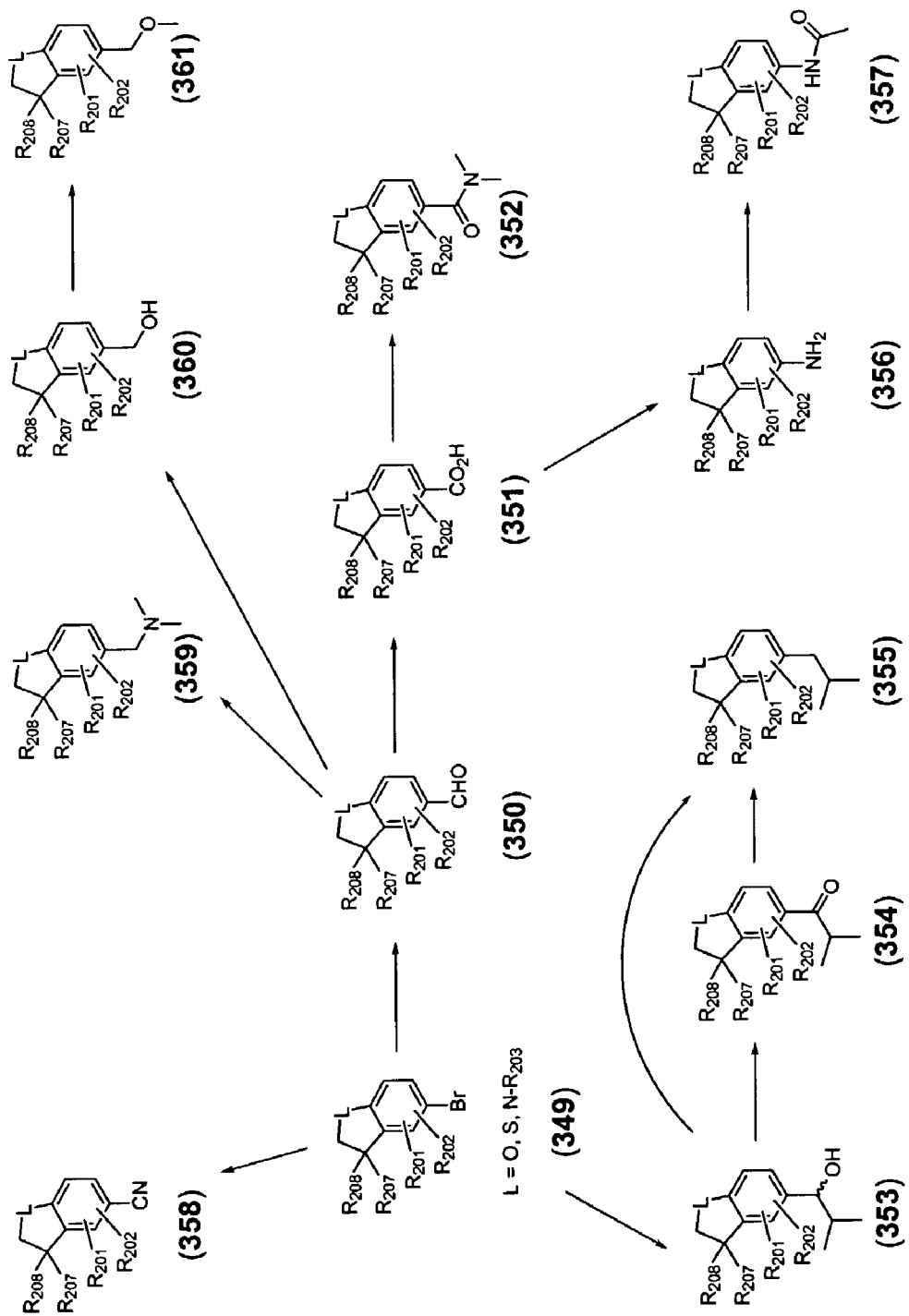
FIG. 10 shows methods for synthesizing synthetic precursors of certain substituted aromatic compounds disclosed herein.

Another method, for example shown in FIG. 10, uses aryl bromide (349) to prepare a variety of $Ar_1$ precursor groups. For example, aryl bromide (349) can be converted to aldehyde (350) through an aryl lithium intermediate and DMF or equivalent thereof. Aldehyde (350) can be oxidized using methods in the art, such as, $KMnO_4$ or similar oxidant, to give carboxylic acid (351). Carboxylic acid (351) can either be coupled with a variety of amines, such as, for example, dimethyl amine, to give amide (352) or allowed to undergo a Curtius Rearrangement to give aniline (356). Such rearrangements can be accomplished using, for example, diphenylphosphorylazide. Aniline (356) can be allowed to react with a variety of electrophils such as, for example, acetyl choride to give amide (357). Aldehyde (350) can also under reductive amination with amines in the presence of reducing reagents, such as, for example, sodium cyanoborohydride, to give amine (359). Aldehyde (350) can also be reduced to give benzyl alcohol (360) and subsequently converted to ether (361) using a base and an alkyl-LG, wherein LG is a leaving group such as those desribed above herein. Aryl bromide (349) can also be converted into an aryl lithium intermediate, in a manner described above, and allow to react with an aldehyde or ketone, for example isobutyraldehyde, to give alcohol (353). Alcohol (353) can either be oxidized to ketone (354) or deoxygenated using, for example, triethylsilane in TFA, to give arylalkyl (355). Aryl bromide (349) can also be converted into benzonitrile (358) using methods known in the art, such as CuCN in quinoline with heat. Benzonitriles can be converted into a variety of hetercycles using methods known in the art.

Some embodiments of the invention relate to compounds of Formula (XV):

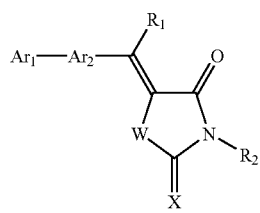
(XV)

and processes for their preparation, wherein $Ar_1$, $Ar_2$, $R_1$, $R_2$, W, and X can have any of the structures disclosed hereinabove:

comprising the steps of:
1) coupling an $Ar_1$ radical with an $Ar_2$ radical to give a biaryl carbonyl containing compound;
wherein:
the $Ar_1$ radical is a substituted or unsubstituted radical having the structure

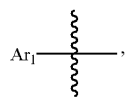

the $Ar_2$ radical has a carbonyl group and comprises a substituted or unsubstituted radical having the structure:

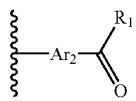

and wherein the biaryl carbonyl containing compound comprises a substituted or unsubstituted radical having the structure:

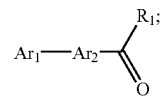

and
2) condensing the biaryl carbonyl containing compound with a heterocyle of the structure:

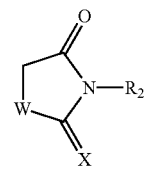

to give a compound of Formula (XV).

In another embodiment of the invention relates to a process wherein the $Ar_1$ radical is of the Formula:

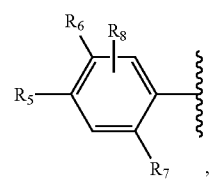

wherein $R_5$ and $R_6$ together with the aromatic ring form a cycloalkyl, substituted cycloalkyl, cycloalkenyl or substituted cycloalkenyl ring, optionally comprising 1, 2 or more heteroatoms that can include O, S, SO, $SO_2$ and N, wherein N is optionally further substituted with groups or radicals that include hydrogen, alkyl or substituted alkyl; and $R_7$ and $R_8$ can be independently or together one or more of hydrogen, alkyl, substituted alkyl, alkenyl, substituted alkenyl, alkynyl, substituted alkynyl, halogen, cyano, nitro, hydroxyl, acyloxy, alkoxy, substituted alkoxy, acyl, amino, mono-substituted amino, di-substituted amino, carboxy, carboalkoxy, alkylcarboxamide, substituted alkylcarboxamide, dialkylcarboxamide, substituted dialkylcarboxamide, alkylsulfonamide, arylsulfonamide, alkylurea, arylurea, alkylcarbamate, arylcarbamate, heteroaryl, haloalkoxy, alkylsulfonyl, alkylsulfinyl, thioalkyl or thiohaloalkyl.

In another embodiment of the invention relates to a process wherein the heterocycle is of the formula:

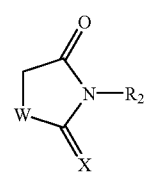

wherein W=S; X=O or S and $R_2$ is a substituted alkyl.

In another embodiment of the invention relates to a process further comprising a reduction step of a compound of Formula (XV) to give a compound of the invention having the structure:

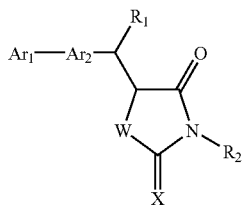

The various organic group transformations utilized herein can be performed by a number of procedures other than those described above. References for other synthetic procedures that can be utilized for the synthetic steps leading to the compounds disclosed herein can be found in, for example, March, J., *Advanced Organic Chemistry*, 5th Edition, Weiley-Interscience (2001); or Larock, R. C., *Comprehensive Organic Transformations, A Guide to Functional Group Preparations*, 2nd Edition, VCH Publishers, Inc. (1999), both incorporated herein by reference, for their disclosures of the known reaction and methods of organic chemistry that might be employed to make the compounds of the invention.

One embodiment of the invention relates to the processes for making compounds of Formula I, wherein n is 0, which comprises coupling two aromatic rings to give a biaryl wherein one of the aryl rings contains a carbonyl moiety, in another embodiment the carbonyl moiety is an aldehyde. The resulting biaryl product can be subsequently condensed with a heterocycle of the structure:

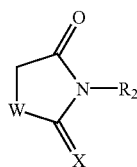

wherein W, X and $R_2$ have the same definitions described herein, to give a compound of Formula (I).

In another embodiment of the invention, wherein n is 0, relates to the process of making compounds of Formula (I) which comprises coupling two aromatic rings to give a biaryl, such as, for example $Ar_1$—$Ar_2$, wherein one of the aryl rings, such as $Ar_2$, contains an oxime moiety to give a compound of Formula (I). In this embodiment the condensation with the hydroxylamine derivative takes place prior to the coupling of two aromatic rings.

Coupling of two aryl rings can be conducted using an aryl boronic acid or esters with an aryl halide (such as, iodo, bromo, or chloro), triflate or diazonium tetrafluoroborate; as described respectively in Suzuki, *Pure & Applied Chem.*, 66:213–222 (1994), Miyaura and Suzuki, *Chem. Rev.* 95:2457–2483 (1995), Watanabe, Miyaura and Suzuki, *Synlett.* 207–210 (1992), Littke and Fu, *Angew. Chem. Int. Ed.*, 37:3387–3388 (1998), Indolese, *Tetrahedron Letters*, 38:3513–3516 (1997), Firooznia, et. al., *Tetrahedron Letters* 40:213–216 (1999), and Darses, et. al., *Bull. Soc. Chim. Fr.* 133:1095–1102 (1996); all incorporated herein by reference. According to this coupling reaction, precursors such as (X) and (XXI) can be used or in another embodiment of the invention (XI) and (XXI) can be used:

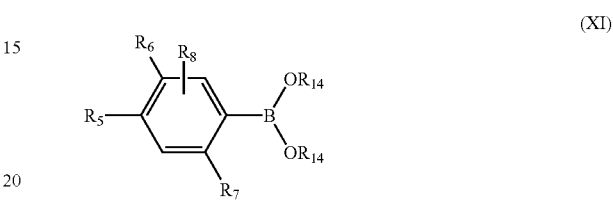

wherein $R_{14}$ is either alkyl or hydrogen and $R_{15}$ is a halide (such as, iodo, bromo, or chloro), triflate or diazonium tetrafluoroborate. Alternately, it is understood that the coupling groups can be reversed, such as, for example, the use of (XXII) and (XXIII), or, in another embodiment, (XII) and (XXIII) to achieve the same coupling product:

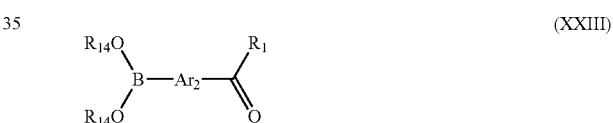

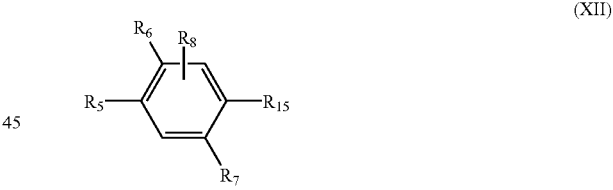

wherein $R_{14}$ and $R_{15}$ have the same meaning as described above. The preparation of the above mentioned precursors can be prepared by methods readily available to those skilled in the art. For example, the boronic ester can be prepared from an aryl halide by conversion into the corresponding aryl lithium, followed by treatment with a trialkyl borate. Preferably, the boronic ester is hydrolyzed to the boronic acid.

The coupling of the two aromatic rings can be accomplished in a similar manner using compound (XIIIa) and compound (XX) or (XI) to give a compound of Formula (I) wherein n=0. Alternatively, compound (XIIIb) and compound (XXII) or (XII) can be coupled to give a compound of Formula (I) wherein n=0. In this process, the condensation takes place prior to the coupling of the two aromatic rings.

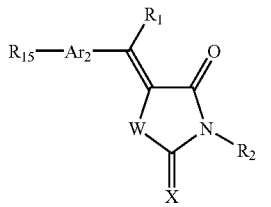

(XIIIa)

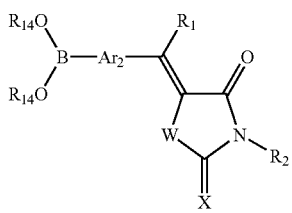

(XIIIb)

The coupling reaction can also be conducted between an arylzinc halide and an aryl halide or triflate. Alternately, the coupling reaction can also be executed using an aryl trialkyltin derivative and an aryl halide or triflate. These coupling methods are reviewed by Stanforth, *Tetrahedron* 54:263–303 (1998) and incorporated herein by reference. In general, the utilization of a specific coupling procedure is selected with respect to available precursors, chemoselectivity, regioselectivity and steric considerations.

Condensation of the biaryl carbonyl containing derivatives (e.g., FIG. 4, compound (XXIV)) with a suitable active methylene compound, such as, 2,4-thiazolidinedione, can be accomplished by the use of methods known in the art. For example, the biaryl carbonyl product from the coupling reaction can be condensed with an active methylene compound to give a benzylidene compound of Formula (I) (i.e., "- - -" is a bond) as described by Tietze and Beifuss, *Comprehensive Organic Synthesis* (Pergamon Press), 2:341–394, (1991), incorporated herein by reference. It is understood by those of skill in the art that intermediates having hydroxyl groups bound thereto can be formed during condensation of a biaryl carbonyl containing derivative and an active methylene compound, as shown below.

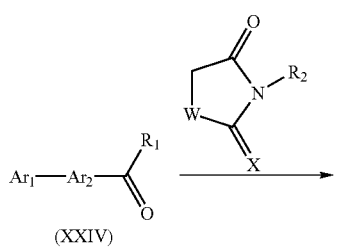

(XXIV)

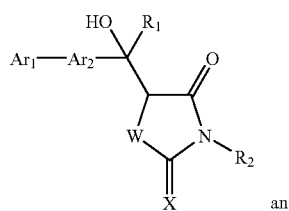

and

-continued

The hydroxyl groups of such intermediates are often eliminated (as water) during the condensation reaction, to form the desired benzylidene compound. Nevertheless, the conditions of the reaction can be modified for the isolation or further use of hydroxyl containing intermediates, and such embodiments are within the scope of the invention. Although the reaction shown above depicts the formation of the condensation intermediate for the reaction between compound (XXIV) and an active methylene compound or heterocycle, it is understood that a similar intermediate is within the scope of the invention for compounds (XLV) and (XLII). Effective catalysts for the condensation can be selected from ammonia, primary, secondary and tertiary amines, either as the free base or the amine salt with an organic acid, such as acetic acid. Examples of catalysts include pyrrolidine, piperidine, pyridine, diethylamine and the acetate salts thereof. Inorganic catalysts can also be used for the condensation. Inorganic catalysts include, but are not limited to, titanium tetrachloride and a tertiary base, such as pyridine; and magnesium oxide or zinc oxide in an inert solvent system. This type of condensation can be strongly solvent-dependent and it is understood that routine experimentation may be necessary to identify the optimal solvent with a particular catalyst, solvents include, but are not limited to, ethanol, tetrahydrofuran, dioxane or toluene; or mixtures thereof.

The resulting benzylidene (e.g., FIG. 4, compound (XXVIII)) can be reduced, such as those procedures known to those skilled in the art, for example, magnesium in an appropriate solvent, hydrogen in the presence of a catalysis, a hydride, such as, for example lithium borohydride, and the like reactions, to a compound of Formula (I) wherein - - - is absent (e.g., FIG. 4, compound (XXX)).

Using the Compositions

Antidiabetic Compounds

Compounds disclosed herein can function, for example, as anti-obesity agents, antidiabetic molecules, modulators of lipid metabolism, and/or carbohydrate metabolism. Compounds having anti-diabetic activity can be identified, for example by various methods and/or assays, such as for example by measuring their ability to induce or inhibit adipocyte differentiation in 3T3 L1 cells. For example, as described in the examples herein, biological activity for these functions can be identified by measuring the compound's ability, when applied at a concentration of 10 uM, to inhibit the adipocyte differentiation and/or lipid accumulation induced by rosiglitazone. In some embodiments, the compounds of the invention inhibit the adipocyte differentiation and/or lipid accumulation induced by rosiglitazone by at least about 25%, or at least about 50%, when the rosiglitazone is applied at a concentration of 0.1 uM.

Alternatively, the candidates can be identified by measuring their ability to inhibit or activate the nuclear receptors RXR, PPARα, PPARγ, PPARδ, LXR and/or FXR. Their in vivo activity can be demonstrated in animal models for type 2 diabetes, such as in the Zuker fatty rat or the KKA$^y$ mouse. In these models a compound is considered active if they are able to exhibit the ability to reduce blood sugar levels for glucose or increase glucose tolerance compared to a placebo, or to treat a disease condition to a level of activity of known active compound or controls. Compounds disclosed herein can be useful, for example, to modulate metabolism (such as, for example, lipid metabolism and carbohydrate metabolism) and can be used to treat type 2 diabetes or reduce or prevent increase of obesity. For example, the compounds of the invention can be equally or more potent than the known PPARγ agonist rosiglitazone for reducing blood sugar levels. In some embodiments, when the compounds of the invention are applied at a concentration of about 10 uM, glucose concentration can be decreased by at least about 5%, or at least about 10%. In some embodiments, the compounds of the invention can, when applied at a concentration of about 10 uM decrease the triglyceride levels of a mammal by at least about 5%, or at least about 10%.

Alternatively, the compounds can be used for preventing or reducing weight gain in animals, as can be shown by demonstrating a prevention or reduction of weight gain diabetic db/db mice or ob/ob mice or any of the other in vivo model described above or known to be useful for such test, by at least about 5%, or at least about 10%.

Modulation of lipid metabolism could also include a decrease of lipid content intracellularly or extracellularly. For example compounds of the invention can reduce adipocyte differention or lipid accumulation induced by rosiglitazone (see example 14, and FIG. 11). Modulation of lipid metabolism could also include the increase of one type of lipid containing particle such as high density lipoprotein (HDL) and or simultaneous decrease in low density lipoprotein (LDL). One suitable animal model to measure such activity in vivo is young Sprague Dawley rats fed a high fat or high cholesterol diet. Modulation of metabolism can occur directly for example, through binding of the compounds disclosed herein with its cognate nuclear receptor, which directly affects an increase or decrease in lipid content by up-regulation or down-regulation of a gene involved in lipid metabolism. Modulation, for example, could be an increase in lipid metabolism, such that lipid metabolism is greater than that of a control. Modulation also includes, for example, an increase in lipid metabolism, such that the lipid metabolism approaches that of a control. Likewise, modulation of lipid metabolism could be a decrease in lipid metabolism, such that the lipid metabolism is less than or decreased when compared to a control, for example an animal treated with placebo. Carbohydrate metabolism can also be up-regulated or down-regulated to either approach the level of carbohydrate metabolism in a control or to deviate from the level of carbohydrate metabolism in a control. Changes in carbohydrate metabolism can directly or indirectly also result in changes of lipid metabolism and, similarly, changes in lipid metabolism can lead to changes in carbohydrate metabolism. An example is type 2 diabetes where an increase in free fatty acids in the patients leads to decreased cellular uptake and metabolism of blood sugars, such as for example glucose. Preferably, administration of the compounds of the invention is effective to decrease blood sugar levels by at least about 5%, or at least about 10%.

It is understood that a variety of lipid molecules can be modulated. The compounds disclosed herein can modulate a single type of lipid molecule, such as cholesterol, or the compounds disclosed herein can modulate multiple types of lipid molecules, such as for example triglycerides. The compounds disclosed herein can also modulate a single or variety of carbohydrate molecules. The compounds disclosed herein can modulate metabolism disorders, such as dyslipidemia. Metabolism can be modulated by administration of the compounds disclosed herein by, for example, decreasing the serum cholesterol and/or the serum triglyceride levels, relative to a control having serum cholesterol and/or triglyceride levels indicative of a mammal having dyslipidemia or hypercholesteremia. It is recognized that any decrease in serum cholesterol and/or triglyceride levels can benefit the mammal having hypercholesteremia. In some embodiments when the compounds of the invention are administered to a patient in a concentration of about 10 uM, the serum cholesterol and/or triglyceride levels can decrease by at least about 5%, or at least about 10%.

These compounds can be characterized by their low molecular weights and physiological stability, and therefore, represent a class that can be implemented to prevent, alleviate, and/or otherwise, treat disorders of lipid and carbohydrate metabolism, such as obesity, dislipidemia, type 2 diabetes and other diseases related to type 2 diabetes. It is understood that treatment or prevention of type 2 diabetes can involve modulation of lipid or carbohydrate metabolism, such as the modulation of serum glucose or serum triglyceride levels.

Anticancer Compounds

Certain compounds disclosed herein can function, for example, as anticancer molecules. This can be measured by determining their effect on the growth of human cancer cell lines in vitro employing common cell culture assays and target validation. One activity is the inhibition of AKT/PKB activity. The protein AKT/PKB is the cellular homologue of the transforming viral oncogene v-AKT and bears significant homology to PKA and PKC. There are three mammalian AKT isoforms α, β, and γ, all contain an N-terminal PH domain, a central kinase domain with an activation-loop and a conserved regulatory serine phosphorylation site near the C terminus (Bellacosa et al., *Oncogene* 1993, 8, 745–754; Testa & Bellacosa, PNAS 2001, 98, 10983–10985). At least 13 AKT substrates have been identified so far in mammalian cells, and they fall into two main classes:

1) regulators of apoptosis
2) cell growth, including protein synthesis, glycogen metabolism, and cell-cycle regulation.

Deregulation of AKT activity is oncogenic, which accounted for its ability to induce multiple simultaneous effects on both cell survival and cell cycle/cell growth. AKT is overexpressed in pancreatic and ovarian carcinomas. AKT also mediate the transforming effect of chicken tumor virus (Chang et al., Science 1997, 276, 1848–1850). The anti-apoptotic effect of AKT is mediated by its ability to phosphorylate substrates involved in cell death which include Forkhead transcription factors, the pro-apoptotic Bcl-2 family member Bad, the cyclic AMP response element binding protein (CREB) and p21 (Blume-Jensen and Hunter, 2001, Zhou et al., Nature Cell Biol. 2001, 3, 245–252). In addition, numerous human malignancies, such as, for example, breast cancer, glioblastoma and germ cell tumors, are associated with inactivating mutations in the tumor-suppressor gene PTEN, leading to deregulated hyperactivity of AKT (Di Cristofano et al., Nature Genet. 2001, 27, 222–224).

The compounds disclosed herein can be used to prevent, alleviate, and/or otherwise, treat proliferative disorders, such as cancer. Compounds disclosed herein can be evaluated in representative animal models, such as, athymic nude mice inoculated with human tumor cell lines. The compounds described herein can be used effectively to prevent, alleviate and/or otherwise treat cancer or precancerous diseases and/or other disease states of uncontrolled proliferation in mammals, including humans.

The biological activity of the compounds of the invention can also be measured utilizing a panel of different human tumor cell lines. It is well known in the art that one or more of the known tumor cell lines can be used to test the antitumor activity of the compounds disclosed here, these tumor cell lines include but are not limited to:

Leukemia: CCRF-CEM, HL-60 (TB), K-562, MOLT-4, RPMI-8226, and SR.
Lung Cancer: A549/ATCC, EKVX, HOP-62, HOP-92, NCI-H226, NCI-H23, NCI-H322M, NCI-H460, and NCI-H522.
Colon Cancer: COLO 205, HCC-2998, HCT-116, HCT-15, HT-29, KM-12, and SW-620.
CNS Cancer: SF-268, SF-295, SF-539, SNB-19, SNB-75, and U-251.
Melanoma: LOX-IMVI, MALME-3M, M-14, SK-MEL-2, SK-MEL-28, SK-MEL-5, UACC-257, and UACC-62.
Ovarian Cancer: IGR-OVI, OVCAR-3, OVCAR-4, OVCAR-5, OVCAR-8, and SK-OV-3.
Renal Cancer: 786-0, A-498, ACHN, CAKI-1, RXF-393, RXF-631, SN12C, TK-10, and U0-31.
Prostate Cancer: PC-3 and DU-145.
Breast Cancer: MCF 7, MCF7/ADR-RES, MDA-MB-231/ATCC, HS578T, MDA-MB-435, MDA-N, BT-549, and T-47D.
Pancretic Cancer: Bx-PC 3.

This anti-cancer activity screening assay provides data regarding the general anti-cancer activity of an individual compound. In particular, as described in the examples herein, active anticancer compounds can be identified by applying the compounds at a concentration of 10 uM to one or more human tumor cell line cultures, such as for example leukemia, lung cancer, colon cancer, CNS cancer, melanoma, ovarian cancer, renal cancer, prostate cancer, breast cancer, or pancreatic cancer, so as to inhibit cell growth of the tumor cells. In some embodiments, when the compounds of the invention are applied to a culture of one of the above cancer cell lines at a concentration of a concentration of about 10 uM, the growth of the cancer cells may be inhibited, or the cancers cells killed to the extent of about 50% or more.

In particular, this type of assay is useful in identifying compounds which have enhanced cytotoxic activity against slow growing tumors as compared to faster growing tumor cells such as leukemia tumor cell lines. The identification of such compounds is beneficial, since previously identified antitumor agents have low cytotoxic activity against slower growing tumors.

Figure 13:
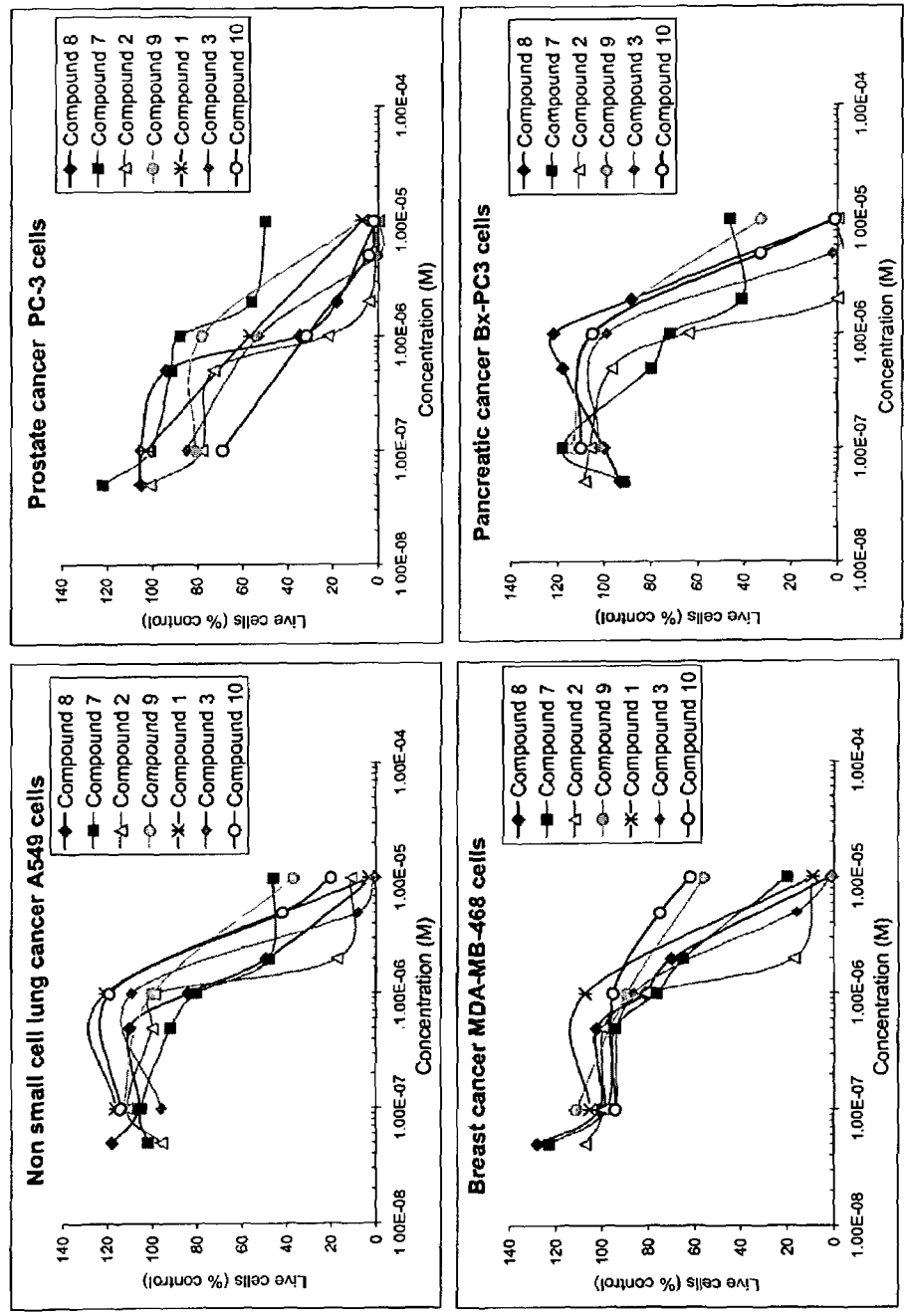
FIG. 13 shows results of tests for the activity of the compounds of the invention with respect to human cell cultures for breast cancer (MDA-MB-468), prostate cancer (PC-3), pancreatic cancer (Bx-PC3), and non-small cell lung cancer (A549) cells.

The anti-cancer activity of the compounds of the invention herein have been tested in in vitro assays using a microculture assay with 3-(4,5-dimethylthiazol-2-yl)-2,5-diphenyltetrazolium bromide ("MTT") a test well known to those skilled in the art. This assay has an advantage over in vivo assay in that results are obtained within a week as opposed to several months. The assay can be carried out in 96-well microtiter plates. The MTT assay is based on the production of a dark blue formazan product by dehydrogenase in the mitochondria of live tumor cells after exposure to drug for 6 days [M. C. Alley, D. A. Scudiero, A. Monks, M. L. Hursey, M. J. Czerwinski, D. L. Fine, B. J. Abbout, J. G. Mayo, R. H. Shoemaker and M. R. Boyd, Cancer Res., 48, 589, 1988]. Thus, only live cells are stained and can be measured at 595 nm. Anti-cancer activity can be reported as percent of the tumor cell growth in the presence of compound at a defined dose compared to control/untreated tumor cells. Examples of results obtained are shown in FIG. 13.

The compounds of the present invention have been found to be potent compounds in a number of biological assays, both in vitro and in vivo, that correlate to, or are representative of, human diseases.

The compounds disclosed herein can be either used singularly or plurally, and with pharmaceutical compositions thereof for the treatment of mammalian diseases, particularly those diseases related to humans. Compounds disclosed herein and compositions thereof can be administered by various methods including, for example, orally, intravenously, enterally, parenterally, topically, nasally, vaginally, opthalinically, sublingually or by inhalation.

An embodiment of the invention relates to the use of the compounds disclosed herein. The compounds disclosed herein can be either used singularly or plurally, and pharmaceutical compositions thereof for the treatment of mammalian diseases, particularly those related to humans. Compounds disclosed herein and compositions thereof can be administered by various methods including, for example, orally, enterally, parentally, topically, nasally, vaginally, ophthalinically, sublingually or by inhalation for the treatment of diseases related to lipid metabolism, such as dyslipidemia and hypercholesteremia, carbohydrate metabolism, polycystic ovary syndrome, syndrome X, type 2 diabetes, including disorders related to type 2 diabetes such as, diabetic retinopathy, neuropathy, macrovascular disease or differentiation of adipocytes. Routes of administration and dosages known in the art can be found in *Comprehensive Medicinal Chemistry,* Volume 5, Hansch, C. Pergamon Press, 1990; incorporated herein by reference.

Another embodiment of the invention relates to the use of the compounds disclosed herein. The compounds disclosed herein can be either used singularly or plurally, and pharmaceutical compositions thereof for the treatment of mammalian diseases, particularly those related to humans. Compounds disclosed herein and compositions thereof can be administered by various methods including, for example, orally, enterally, parentally, topically, nasally, vaginally, ophthalinically, sublingually or by inhalation for the treatment of diseases related to proliferative diseases, such as, cancer, including, but not limited to, ovarian cancer and pancreatic cancer. Routes of administration and dosages known in the art can be found in *Comprehensive Medicinal Chemistry,* Volume 5, Hansch, C. Pergamon Press, 1990; incorporated herein by reference.

Although the compounds described herein can be administered as pure chemicals, it is preferable to present the active ingredient as a pharmaceutical composition. Thus another embodiment of the disclosed compounds is the use of a pharmaceutical composition comprising one or more compounds and/or a pharmaceutically acceptable salt thereof, together with one or more pharmaceutically acceptable carriers thereof and, optionally, other therapeutic and/or prophylactic ingredients. The carrier(s) must be 'acceptable' in the sense of being compatible with the other ingredients of the composition and not overly deleterious to the recipient thereof. The compositions will include, an effective amount of the selected compound or compounds to perform a desired biological and/or medicinal function, in combination with a pharmaceutically acceptable carrier and, in addition, can include other medicinal agents, pharmaceutical agents, carriers, adjuvants, diluents, etc.

Pharmaceutical compositions typically include those suitable for oral, enteral, parental (including intramuscular, subcutaneous and intravenous), topical, nasal, vaginal, ophthalinical, sublingually or by inhalation administration. The compositions can, where appropriate, be conveniently presented in discrete unit dosage forms and can be prepared by any of the methods well known in the art of pharmacy. Such methods include the step of bringing into association the active compound with liquid carriers, solid matrices, semi-solid carriers, finely divided solid carriers or combination thereof, and then, if necessary, shaping the product into the desired delivery system.

Pharmaceutical compositions suitable for oral administration can be presented as discrete unit dosage forms such as hard or soft gelatin capsules, cachets or tablets each containing a predetermined amount of the active ingredient; as a powder or as granules; as a solution, a suspension or as an emulsion. The active ingredient can also be presented as a bolus, electuary or paste. Tablets and capsules for oral administration can contain conventional excipients such as binding agents, fillers, lubricants, disintegrants, or wetting agents. The tablets can be coated according to methods well known in the art, e.g., with enteric coatings.

Oral liquid preparations can be in the form of, for example, aqueous or oily suspensions, solutions, emulsions, syrups or elixirs, or can be presented as a dry product for constitution with water or other suitable vehicle before use. Such liquid preparations can contain conventional additives such as suspending agents, emulsifying agents, non-aqueous vehicles (which can include edible oils), or one or more preservative.

The compounds can also be formulated for parenteral administration (e.g., by injection, for example, bolus injection or continuous infusion) and can be presented in unit dose form in ampules, pre-filled syringes, small bolus infusion containers or in multi-does containers with an added preservative. The compositions can take such forms as suspensions, solutions, or emulsions in oily or aqueous vehicles, and can contain formulatory agents such as suspending, stabilizing and/or dispersing agents. Alternatively, the active ingredient can be in powder form, obtained by aseptic isolation of sterile solid or by lyophilization from solution, for constitution with a suitable vehicle, e.g., sterile, pyrogen-free water, before use.

For topical administration to the epidermis, the compounds can be formulated as ointments, creams or lotions, or as the active ingredient of a transdermal patch. Suitable transdermal delivery systems are disclosed, for example, in Fisher et al. (U.S. Pat. No. 4,788,063, incorporated herein by reference) or Bawa et al. (U.S. Pat. Nos. 4,931,279, 4,668, 506 and 4,713,224; all incorporated herein by reference). Ointments and creams can, for example, be formulated with an aqueous or oily base with the addition of suitable thickening and/or gelling agents. Lotions can be formulated with an aqueous or oily base and will in general also contain one or more emulsifying agents, stabilizing agents, dispersing agents, suspending agents, thickening agents, or coloring agents. The active ingredient can also be delivered via iontophoresis, e.g., as disclosed in U.S. Pat. Nos. 4,140,122, 4383,529, or 4,051,842; incorporated herein by reference.

Compositions suitable for topical administration in the mouth include unit dosage forms such as lozenges comprising active ingredient in a flavored base, usually sucrose and acacia or tragacanth; pastilles comprising the active ingredient in an inert base such as gelatin and glycerin or sucrose and acacia; mucoadherent gels, and mouthwashes comprising the active ingredient in a suitable liquid carrier.

When desired, the above-described compositions can be adapted to provide sustained release of the active ingredient employed, e.g., by combination thereof with certain hydrophilic polymer matrices, e.g., comprising natural gels, synthetic polymer gels or mixtures thereof.

The pharmaceutical compositions according to the invention can also contain other adjuvants such as flavorings, coloring, antimicrobial agents, or preservatives.

It will be further appreciated that the amount of the compound, or an active salt or derivative thereof, required for effective use in treatment will vary not only with the particular compound and/or salt selected but also with the route of administration, the nature of the condition being treated and the age and condition of the patient and will be ultimately at the discretion of the attendant physician or clinician. An effective amount of a compound provided herein is a substantially nontoxic but sufficient amount of the compound to provide the desired modulation of metabolism or gene expression.

In general, one of skill in the art understands how to extrapolate in vivo data obtained in a model organism, such as mouse, rat and the like, to another mammal, such as a human. These extrapolations are not simply based on the weights of the two organisms, but rather incorporate differences in metabolism, differences in pharmacological delivery, and administrative routes. Based on these types of considerations, a suitable dose can, in alternative embodiments, typically be in the range of from about 0.5 to about 100 mg/kg/day, from about 1 to about 75 mg/kg of body weight per day, from about 3 to about 50 mg per kilogram body weight of the recipient per day, or in the range of 6 to 90 mg/kg/day, or typically in the range of 15 to 60 mg/kg/day.

The compound is conveniently administered in unit dosage form; for example, in alternative embodiments, containing typically 0.5 to 1000 mg, 5 to 750 mg, most conveniently, or 10 to 500 mg of active ingredient per unit dosage form.

One skilled in the art will recognize that dosage and dosage forms outside these typical ranges can be tested and, where appropriate, be used in the methods of this invention.

In separate embodiments, the active ingredient can be administered to achieve peak plasma concentrations of the active compound of from typically about 0.5 to about 75 µM, about 1 to 50 µM, or about 2 to about 30 µM. This can be achieved, for example, by the intravenous injection of a 0.05 to 5% solution of the active ingredient, optionally in saline, or orally administered as a bolus containing about 0.5–500 mg of the active ingredient. Desirable blood levels can be maintained by continuous infusion to provide about 0.01–5.0 mg/kg/hr or by intermittent infusions containing about 0.4–15 mg/kg of the active ingredients.

The desired dose can conveniently be presented in a single dose or as divided doses administered at appropriate intervals, for example, as two, three, four or more sub-doses per day. The sub-dose itself can be further divided, e.g., into a number of discrete loosely spaced administrations; such as multiple inhalations from an insufflator or by application of a plurality of drops into the eye.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as can be applied to the essential features hereinbefore set forth, and as follows in the scope of the appended claims.

The following examples are given to illustrate the invention and are not intended to be limiting or exclusive in any manner:

EXAMPLES

Example 1

{5-[4-Methoxy-3-(3,5,5,8,8-pentamethyl-5,6,7,8-tetrahydro-naphthalen-2-yl)-benzylidene]-4-oxo-2-thioxo-thiazolidin-3-yl}-acetic acid, also referred to Compound 1 herein

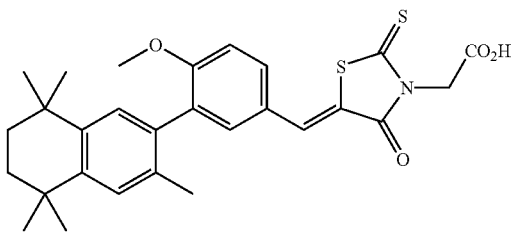

To a mixture of 4-methoxy-3-(3,5,5,8,8-pentamethyl-5,6,7,8-tetrahydronaphthylen-2-yl) benzaldehyde (1.0 g, 3.0 mmol) and rhodanine acetic acid (0.570 g, 3.0 mmol) in toluene (10 mL) was added piperidine (0.030 mL) and acetic acid (0.030 mL). The resulting mixture was heated to reflux overnight. The solution was cooled to room temperature giving a solid. The solid was collected and recrystallized from $CH_2Cl_2$ and hexane (twice) and from ethanol to afford after drying 0.50 g (33% yield) of {5-[4-Methoxy-3-(3,5,5,8,8-pentamethyl-5,6,7,8-tetrahydro-naphthalen-2-yl)-benzylidene]-4-oxo-2-thioxo-thiazolidin-3-yl}-acetic acid; purity: 99.5% (254 nm) and 99.2% (340 nm); mp 242–244° C. $^1$H NMR (300 MHz; DMSO-$d_6$): 1.21 (s, 6 H); 1.26 (s, 6 H); 1.63 (s, 4 H); 2.00 (s, 3 H); 3.81 (s, 3 H); 4.72 (s, 2 H); 7.04 (s, 1 H); 7.17 (s, 1 H); 7.27 (d, J=8.7 Hz, 1 H); 7.40 (d, J=2.1 Hz, 1 H); 7.68 (dd, $J_1$=2.1 Hz, $J_2$=8.7 Hz, 1 H); 7.90 (s, 1 H); $^{13}$C data was obtained on a different lot: $^{13}$C NMR (125 MHz, DMSO-$d_6$): 19.3, 31.6, 33.5, 33.6, 34.7, 45.1, 55.7, 112.3, 118.7, 125.3, 127.4, 127.8, 131.5, 132.0, 133.0, 134.0, 134.2, 134.4, 141.6, 143.6, 158.9, 166.4, 167.3, 193.0

The intermediate 4-methoxy-3-(3,5,5,8,8-pentamethyl-5,6,7,8-tetrahydronaphthalen-2-yl)benzaldehyde was prepared as follows:

a. (3,5,5,8,8-Pentamethyl-5,6,7,8-tetrahydronaphthalen-2-yl) boronic acid.

The (3,5,5,8,8-pentamethyl-5,6,7,8-tetrahydronaphthalen-2-yl) boronic acid, was prepared in an analogous manner as reported by Dawson et al. (*J. Med. Chem.* 1995, 38, 3368–3383).

b. 3-(3,5,5,8,8-Pentamethyl-5,6,7,8-tetrahydronaphthalen-2-yl)-4-methoxy-benzaldehyde.

A mixture of 3-bromo-4-methoxybenzaldehyde (19.0 g, 88.4 mmol), (3,5,5,8,8-pentamethyl-5,6,7,8-tetrahydronaphthalen-2-yl) boronic acid (23.8 g, 97.2 mmol) and potassium carbonate (48.8 g, 353.6 mmol) in 1,2-dimethoxyethane (500 mL) and water (40 mL) was degassed with argon for 60 minutes. Tetrakis(triphenylphosphine) palladium(0) (5.0 g, 4.3 mmol) was added and the mixture heated at reflux under argon for 16 hours. The solution was cooled to room temperature, diluted with ethyl acetate (200 mL) and washed successively with water (100 mL) and brine (100 mL), dried over anhydrous magnesium sulfate, filtered and evaporated. The residue was chromatographed on silica gel (eluent: ethyl acetate/hexane, 1:9) to give 26.8 g of 3-(3,5,5,8,8-pentamethyl-5,6,7,8-tetrahydronaphthalen-2-yl)-4-methoxy-benzaldehyde (90%). $^1$H NMR (500 MHz; CDCl$_3$): δ 1.26 (s, 6 H); 1.32 (s, 6 H); 1.70 (s, 4 H); 2.08 (s, 3 H); 3.89 (s, 3 H); 7.06 (d, J=8.5 Hz, 1 H); 7.09 (s, 1 H); 7.16 (s, 1 H); 7.71 (d, J=2.0 Hz, 1 H); 7.88 (dd, $J_1$=2.0 Hz, $J_2$=8.5 Hz 1 H), 9.91 (s, 1 H).

Example 2

{5-[4-Trifluoromethoxy-3-(3,5,5,8,8-pentamethyl-5,6,7,8-tetrahydronaphthalen-2-yl)-benzylidene]-4-oxo-2-thioxo-thiazolidin-3-yl}-acetic acid, also referred to Compound 2 herein

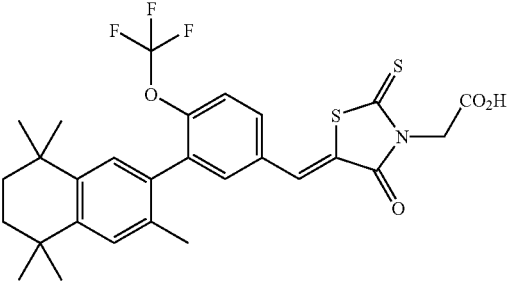

{5-[4-Trifluoromethoxy-3-(3,5,5,8,8-pentamethyl-5,6,7,8-tetrahydronaphthalen-2-yl)-benzylidene]-4-oxo-2-thioxo-thiazolidin-3-yl}-acetic acid was prepared in a similar manner as described in Example 1 using 4-trifluoromethoxy-3-(3,5,5,8,8-pentamethyl-5,6,7,8-tetrahydro-naphthalen-2-yl) benzaldehyde (95% yield), purity: 98.2% (254 nm) and 98.6% (340 nm), mp 193–194° C., $^1$H NMR (300 MHz; DMSO-$d_6$) 1.22 (s, 6 H); 1.29 (s, 6 H); 1.66 (s, 4 H); 2.07 (s, 3 H); 4.75 (s, 2 H); 7.11 (s, 1 H); 7.28 (s, 1 H); 7.66 (d, J=6.9 Hz, 1 H); 7.71 (d, J=2.1 Hz, 1 H); 7.79 (dd, $J_1$=8.7 Hz, $J_2$=2.4 Hz, 1 H); 7.98 (s, 1 H).

The intermediate 3-trifluoromethoxy-4-(3,5,5,8,8-pentamethyl-5,6,7,8-tetrahydronaphthalen-2-yl) benzaldehyde was prepared as follows:

a. 3-Bromo-4-trifluoromethoxybenzaldehyde.

To a solution of 4-trifluoromethoxybenzaldehyde (215.0 g, 1.13 mol) in a mixture of TFA (300 mL), $CH_2Cl_2$ (300 mL) and $H_2SO_4$ (150 mL) was added at room temperature N-bromosuccinimide (402.0 g, 2.26 mol) in equal portions over seven hours. The reaction mixture was stirred for four days at room temperature, poured into ice-water and extracted with $CH_2Cl_2$. The organic layer was washed with water and subsequently treated with saturated NaHCO$_3$ (1.5

L) for two hours. The layers were separated and the organic layer further washed with water and brine, dried over MgSO$_4$, filtered and evaporated. The residue was triturated with hexane and filtered. After evaporation of the solvent, the residue was distilled to give 3-bromo-4-trifluoromethoxybenzaldehyde (190.2 g, 81° C., 1.0 mm/Hg, 62%).

b. 3-Trifluoromethoxy-4-(3,5,5,8,8-pentamethyl-5,6,7,8-tetrahydronaphthalen-2-yl) benzaldehyde.

To a solution of 3-bromo-4-trifluoromethoxybenzaldehyde (10.0 g, 37.2 mmol), (3,5,5,8,8-pentamethyl-5,6,7,8-tetrahydronaphthalen-2-yl) boronic acid (11.0 g, 44.68 mmol, 1.2 eq) in a mixture of toluene (100 mL), ethanol (20 mL) and water (15 mL) was added potassium carbonate (10.28 g, 74.4 mmol, 2 eq). The mixture was degased with argon for 40 minutes. Tetrakis(triphenylphosphine)palladium(0) (0.86 g, 0.74 mmol, 0.02 eq) was added and the mixture heated at reflux under argon for 22 hours. The mixture was cooled to room temperature, diluted with ethyl acetate and washed successively with water and brine, dried over MgSO$_4$, filtered and evaporated. The residue was chromatographed on silica gel (eluent: ethyl acetate/hexane 5:95) to give 3-trifluoromethoxy-4-(3,5,5,8,8-pentamethyl-5,6,7,8-tetrahydronaphthalen-2-yl) benzaldehyde (11.1 g, 76%), $^1$H NMR (300 MHz; CDCl$_3$) 1.25 (s, 6 H); 1.32 (s, 6 H); 1.70 (s, 4 H); 2.08 (s, 3 H); 7.06 (s, 1 H); 7.18 (s, 1 H); 7.48 (dd, J$_1$=8.4 Hz, J$_2$=1.5 Hz, 1 H); 7.84 (d, J=2.0 Hz, 1 H); 7.88 (dd, J$_1$=2.0 Hz, J$_2$=8.5 Hz, 1 H), 9.91 (s, 1 H).

Example 3

{5-[6-Methoxy-5-(3,5,5,8,8-pentamethyl-5,6,7,8-tetrahydro-naphthalen-2-yl)-pyridin-3-yl methylene]-4-oxo-2-thioxo-thiazolidin-3-yl}-acetic acid, also referred to Compound 3 herein

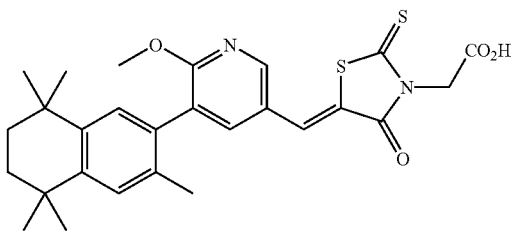

{5-[6-Methoxy-5-(3,5,5,8,8-pentamethyl-5,6,7,8-tetrahydro-naphthalen-2-yl)-pyridin-3-yl methylene]-4-oxo-2-thioxo-thiazolidin-3-yl}-acetic acid was prepared in a similar manner as described in Example 1 using 2-methoxy-3-(3,5,5,8,8-pentamethyl-5,6,7,8-tetrahydro-naphthalen-2-yl)pyridine-5-carboxaldehyde, mp 253–255° C., $^1$H NMR (300 MHz; DMSO-d$_6$) 1.24 (s, 6 H); 1.28 (s, 6 H); 1.66 (s, 4 H); 2.06 (s, 3 H); 3.94 (s, 3 H); 4.75 (s, 2 H); 7.14 (s, 1 H); 7.23 (s, 1 H); 7.74 (s, 1 H); 7.97 (s, 1 H); 8.59 (s, 1 H).

The intermediate 2-methoxy-3-(3,5,5,8,8-pentamethyl-5,6,7,8-tetrahydronaphthalen-2-yl)pyridine-5-carboxaldehyde was prepared as follows:

a. 5-Bromo-2-methoxy-pyridine

To a suspension of 2-methoxypyridine (10.00 g, 0.09 mol) and sodium acetate (8.27 g, 0.10 mmol) in 30 mL of glacial acetic acid was added a solution of bromine in 20 mL glacial acetic acid while maintaining the reaction temperature below 50° C. After 3 hours, 100 mL of H$_2$O was added and the resulting solution neutralized with cold 2.5 M NaOH. The suspension was extracted with ether (2×200 mL), the combined organics were dried over MgSO$_4$, filtered and evaporated. The crude material was purified on silica gel (eluent: hexane to hexane:ethyl acetate 97:3) and distilled (34–36.5° C./0.05 mm Hg) to give 8.84 g (51.3%) of 5-bromo-2-methoxypyridine as a clear colorless liquid.

b. 2-methoxy-pyridine-5-carboxaldehyde.

To a solution of 5-bromo-2-methoxy-pyridine (8.50 g, 45.2 mmol) in 100 mL dry ether under argon at −64° C. was added 1.6 M n-BuLi in hexanes. The resulting mixture was stirred at −64° C. for 40 minutes and allowed to warm to −35° C. To the resulting suspension was added 7.0 mL of dry DMF over 10 minutes. After 15 minutes, the mixture was allowed to warm to 0° C. and 75 mL of 5% NH$_4$Cl was added. The resulting mixture was separated and the aqueous layer extracted with EtOAc (3×75 mL). The organics were combined, dried (MgSO$_4$), filtered and evaporated under vacuum to give 2-methoxy-pyridine-5-carboxaldehyde as a tannish solid (recrystallized from hexane), 3.76 g (60.6%); m.p. 48.5–50° C.

c. 2-methoxy-3-bromo-pyridine-5-carboxyaldehyde

To a suspension of 2-methoxypyridine-5-carboxyaldehyde (3.50 g, 25.5 mmol) and sodium acetate (2.30 g, 28.1 mmol) in 15 mL of glacial acetic acid was added a solution of bromine (1.45 mL, 28.1 mmol) in 20 mL glacial acetic acid and the resulting mixture heated to 100° C. for 18 hours under argon. The mixture was cooled, diluted with water (50 mL) and neutralized with 2.0 M NaOH. The resulting mixture was extracted with ether (4×200 mL), the combined organics dried (MgSO$_4$), filtered and evaporated. The crude material was purified on silica gel [gradient, hexane:ethyl acetate (99:1) to hexane:ethyl acetate (92:8)] to give 2-methoxy-3-bromo-pyridine-5-carboxyaldehyde as a white solid, 0.97 g (17.6%). $^1$H NMR (500 MHz, CDCl$_3$): δ 4.11 (s, 3 H), 8.29 (d, J=2.0 Hz, 1 H), 8.56 (d, J=2.0 Hz, 1 H), 9.92 (s, 1 H).

d. 2-Methoxy-3-(3,5,5,8,8-pentamethyl-5,6,7,8-tetrahydronaphthalen-2-yl)pyridine-5-carboxaldehyde.

A mixture of 2-methoxy-3-bromo-pyridine-5-carboxyaldehyde (319 mg, 1.48 mmol), (3,5,5,8,8-pentamethyl-5,6,7,8-tetrahydronaphthalen-2-yl) boronic acid (545 mg, 2.22 mmol), potassium carbonate (817 mg, 5.91 mmol) and water (2 mL) in anhydrous 1,2-dimethoxyethane (30 mL) was degassed with argon for 15 minutes prior to the addition of tetrakis(triphenylphosphine)palladium (0) (342 mg, 0.30 mmol). The reaction mixture was heated under reflux for 15 hours, allowed to cool to room temperature and extracted with ethyl acetate (2×100 mL). The organic extracts were successively washed with water (100 mL), a saturated aqueous solution of NH$_4$Cl (100 mL), brine (100 mL), dried over MgSO$_4$ and filtered. Removal of the solvent under reduced pressure gave an oil which was purified by column chromatography, Biotage 12M cartridge, eluting with 5% ethyl acetate/95% hexane, to give 2-methoxy-3-(3,5,5,8,8-pentamethyl-5,6,7,8-tetrahydronaphthalen-2-yl)pyridine-5-carboxaldehyde (100% yield). $^1$H NMR (500 MHz, CDCl$_3$): δ 1.24 (s, 6 H), 1.27 (s, 6 H), 1.70 (s, 4 H), 2.09 (s, 3 H), 4.09 (s, 3 H), 7.07 (s, 1 H), 7.17 (s, 1 H), 7.94 (d, J=2.0 Hz, 1 H), 8.64 (d, J=2.0 Hz, 1 H), 10.01 (s, 1 H).

Example 4

3-Ethyl-{5-[4-Trifluoromethoxy-3-(3,5,5,8,8-pentamethyl-5,6,7,8-tetrahydro-naphthalen-2-yl)-benzylidene]-2-thioxo-thiazolidin-4-one, also referred to Compound 4 herein

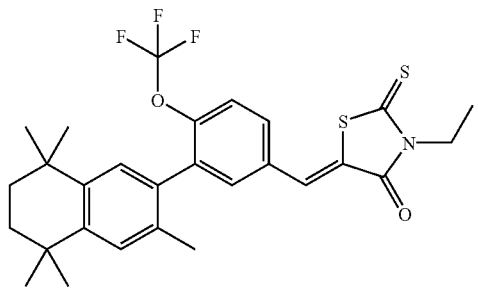

3-Ethyl-{5-[4-trifluoromethoxy-3-(3,5,5,8,8-pentamethyl-5,6,7,8-tetrahydro-naphthalen-2-yl)-benzylidene]-4-oxo-2-thioxo-thiazolidin-3-yl}-acetic acid was prepared in a similar manner as described in Example 1 using 4-trifluoromethoxy-3-(3,5,5,8,8-pentamethyl-5,6,7,8-tetrahydro-naphthalen-2-yl)benzaldehyde and 3-ethyl rhodanine, mp 129–130° C., $^1$H NMR (300 MHz; DMSO) 1.19 (m, 3 H); 1.22 (s, 6 H); 1.28 (s, 6 H); 1.66 (s, 4 H); 2.06 (s, 3 H); 4.07 (q, J=7.2 Hz, 2 H); 7.10 (s, 1 H); 7.28 (s, 1 H); 7.66 (m, 2 H); 7.75 (dd, $J_1$=2.4 Hz, $J_2$=8.5 Hz, 1 H); 7.90 (s, 1 H).

Example 5

3-Methyl-{5-[4-trifluoromethoxy-3-(3,5,5,8,8-pentamethyl-5,6,7,8-tetrahydro-naphthalen-2-yl)-benzylidene]-2-thioxo-thiazolidin-4-one, also referred to Compound 5 herein

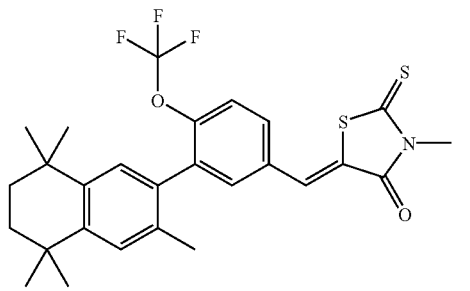

3-Methyl-{5-[4-trifluoromethoxy-3-(3,5,5,8,8-pentamethyl-5,6,7,8-tetrahydro-naphthalen-2-yl)-benzylidene]-4-oxo-2-thioxo-thiazolidin-3-yl}-acetic acid was prepared in a similar manner as described in Example 1 using 4-trifluoromethoxy-3-(3,5,5,8,8-pentamethyl-5,6,7,8-tetrahydro-naphthalen-2-yl)benzaldehyde and 3-methyl rhodanine, mp 168–169° C., $^1$H NMR (300 MHz; DMSO-$d_6$) 1.19 (s, 6 H); 1.26 (s, 6 H); 1.64 (s, 4 H); 2.04 (s, 3 H); 3.38 (s, 3 H); 7.08 (s, 1 H); 7.25 (s, 1 H); 7.64 (m, 2 H); 7.73 (dd, $J_1$=2.1 Hz, $J_2$=8.5 Hz, 1 H); 7.88 (s, 1 H).

Example 6

5-[4-Methoxy-3-(3,5,5,8,8-pentamethyl-5,6,7,8-tetrahydro-naphthalen-2-yl)-benzylidene]-3-(2-pyridin-2-yl-ethyl)-thiazolidine-2,4-dione; also referred to herein as Compound 6.

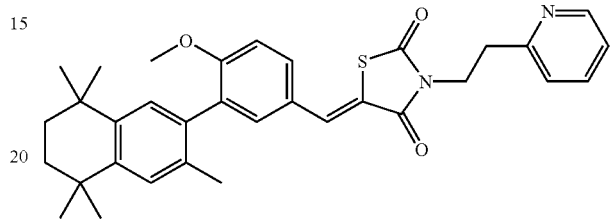

5-[4-Methoxy-3-(3,5,5,8,8-pentamethyl-5,6,7,8-tetrahydro-naphthalen-2-yl)-benzylidene]-3-(2-pyridin-2-yl-ethyl)-thiazolidine-2,4-dione was prepared in a similar manner as described in Example 1 using 4-methoxy-3-(3,5,5,8,8-pentamethyl-5,6,7,8-tetrahydro-naphthalen-2-yl) benzaldehyde and 3-(2-pyridin-2-yl-ethyl)-thiazolidine-2,4-dione, mp 170–171° C., $^1$H NMR (300 MHz; DMSO-$d_6$) 1.23 (s, 6 H); 1.28 (s, 6 H); 1.65 (s, 4 H); 2.02 (s, 3 H); 3.04 (t, J=7.1 Hz, 2 H); 3.81 (s, 3 H); 3.99 (t, J=7.1 Hz, 2 H); 7.04 (s, 1 H); 7.18–7.29 (m, 4 H); 7.36 (d, J=2.1 Hz, 1 H); 7.64 (dd, $J_1$=9 Hz, $J_2$=3.6 Hz, 1 H); 7.70 (t, J=3.7 Hz, 1 H); 7.91 (s, 1 H); 8.46 (d, J=4.0 Hz, 1 H).

The intermediate 4-methoxy-3-(3,5,5,8,8-pentamethyl-5,6,7,8-tetrahydro-naphthalen-2-yl) benzaldehyde was prepared according to the procedure described in Example 1 and 3-(2-pyridin-2-yl-ethyl)-thiazolidine-2,4-dione was prepared as shown below:

a. 3-(2-Pyridin-2-yl-ethyl)-thiazolidine-2,4-dione.

To a mixture of triphenylphosphine (7.61 g, 29.0 mmol), thiazolidinedinone (3.40 g, 29.0 mmol), 2-(2-pyridyl)-ethanol (3.57 g, 29.0 mmol) in DMF (100 mL) at 0° C. under argon was added DIAD (5.86 g, 29.0 mmol, 5.71 mL) dropwise over 10 minutes. The mixture was allowed to warm to room temperature over night. The resulting mixture was poured into water and extracted with ethyl acetate (2×). The combined organics were washed with water, brine and dried (MgSO$_4$). The mixture was filtered, evaporated and the resulting material was purified on silica gel (eluent: hexane: ethyl acetate 3:2 to 1:1) to give pure product along with some impure material. This impure material was dissolved in EtOAc, washed with 1 N HCl, the aqueous layer was neutralized and subsequently extracted with EtOAc (3×). The organics were washed with brine, dried (MgSO$_4$), filtered and evaporated to provide pure product. The product was combined to afford 3.14 g (49%) of 3-(2-pyridin-2-yl-ethyl)-thiazolidine-2,4-dione as an off-white solid; $^1$H NMR (300 MHz; DMSO-$d_6$): δ 2.92 (t, J=6.9 Hz, 2 H), 3.81 (t, J=6.9 Hz, 2 H), 4.14 (s, 2 H), 7.15–7.20 (m, 1 H), 7.24 (d, J=8.0 Hz, 1 H), 7.68 (dt, $J_1$=8.0 Hz, $J_2$=2.0 Hz, 1 H), 8.45 (ddd, $J_1$=5.0 Hz, $J_2$=2.0 Hz, $J_3$=1.0 Hz, 1 H).

Example 7

{5-[6-(3-Dimethylamino-5,5,8,8-tetramethyl-5,6,7,8-tetrahydro-naphthalen-2-yl)-naphthalen-2-yl methylene]-4-oxo-2-thioxo-thiazolidin-3-yl}-acetic acid, also referred to Compound 7 herein

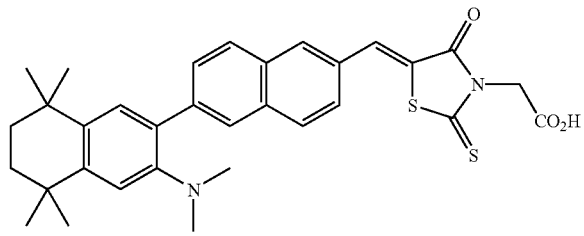

{5-[6-(3-Dimethylamino-5,5,8,8-tetramethyl-5,6,7,8-tetrahydro-naphthalen-2-yl)-naphthalen-2-yl methylene]-4-oxo-2-thioxo-thiazolidin-3-yl}-acetic acid was prepared in a similar manner as described in Example 1 using 6-(3-dimethylamino-5,5,8,8-tetramethyl-5,6,7,8-tetrahydro-naphthalen-2-carboxaldehyde and rhodanine acetic acid, mp 194–196° C., $^1$H NMR (300 MHz; DMSO-$d_6$) 1.25 (s, 6 H), 1.30 (s, 6 H), 1.66 (s, 4 H), 2.47 (s, 6 H), 4.76 (s, 2 H); 6.99 (s, 1 H), 7.21 (s, 1 H), 7.74 (dd, $J_1$=1.5 Hz, $J_2$=8.4 Hz, 1 H), 7.87 (dd, $J_1$=1.5 Hz, $J_2$=8.4 Hz, 1 H), 8.05 (brs, 2 H), 8.07 (d, J=8.1 Hz, 1 H), 8.10 (d, J=8.1 Hz, 1 H), 8.28 (s, 1 H).

The intermediate 6-(3-dimethylamino-5,5,8,8-tetramethyl-5,6,7,8-tetrahydro-naphthalen-2-carboxaldehyde was prepared as follows:

a. 6-Hydroxy-naphthalene-2-carboxylic acid ethyl ester.

A solution of 6-hydroxy-2-naphthoic acid (75.9 g, 0.40 mol) in ethanol (1.0 L) and sulfuric acid (5.0 mL) was heated to reflux under an atmosphere of nitrogen. After 16 hours, the volume was removed to approximately half via simple distillation and the resulting solution was diluted with water. The resulting cloudy mixture was extracted with EtOAc (4x) and the combined organics were successively washed with NaHCO$_3$ (0.25 M, twice), water, brine and dried (MgSO$_4$). The mixture was filtered and evaporated to give 6-hydroxy-naphthalene-2-carboxylic acid ethyl ester, 85.4 g (98%).

$^1$H NMR (300 MHz; CDCl$_3$) 1.44 (t, J=7.5 Hz, 3 H), 4.45 (q, J=7.5 Hz, 2 H), 6.48 (brs, 1 H), 7.10–7.25 (m, 2 H), 7.66 (d, J=8.4 Hz, 1 H), 7.84 (dd, $J_1$=9.0 Hz, $J_2$=1.0 Hz, 1 H), 8.00 (dd, $J_1$=9.0 Hz, $J_2$=1.5 Hz, 1 H), 8.53 (d, J=1.0 Hz, 1 H).

b. 6-Trifluoromethanesulfonyloxy-naphthalene-2-carboxylic acid ethyl ester.

To a mixture of 6-hydroxy-naphthalene-2-carboxylic acid ethyl ester (85.00 g, 0.39 mol) in CH$_2$Cl$_2$ (600 mL) and pyridine (93.3 g, 1.18 mol, 95 mL) near 0° C. under an atmosphere of argon was added triflic anhydride (144.2, 0.51 mol, 86 mL) dropwise. The dark solution was allowed to warm to room temperature over night. The mixture was poured onto ice and the resulting layers were separated. The aqueous layer was washed with CH$_2$Cl$_2$ and the combined organics were washed water, 0.5 N HCl (2x), water and brine. The mixture was dried (MgSO$_4$), filtered and evaporated to give 6-trifluoromethanesulfonyloxy-naphthalene-2-carboxylic acid ethyl ester as a yellowish solid, 136.97 g (100%). $^1$H NMR (300 MHz; CDCl$_3$) 1.46 (t, J=7.0 Hz, 3 H), 4.46 (q, J=7.0 Hz, 2 H), 7.43 (dd, $J_1$=9.0 Hz, $J_2$=2.5 Hz, 1 H), 7.79 (d, J=2.5 Hz, 1 H), 7.91 (d, J=9.0 Hz, 1 H), 8.04 (d, J=9.0 Hz, 1 H), 8.17 (dd, $J_1$=9.0 Hz, $J_2$=2.0 Hz, 1 H), 8.64 (brs, 1 H).

c. 6-Trifluoromethanesulfonyloxy-naphthalen-2-yl-methanol.

To a slurry of 6-trifluoromethanesulfonyloxy-naphthalene-2-carboxylic acid ethyl ester (136.50 g, 0.392 mol) in toluene (1.0 L) at −70° C. was added a solution of DIBAL (1.5 M, 5.75 mL, 0.862 mol) dropwise while maintaining an internal temperature below −55° C. The resulting mixture was allowed to stir for 1 hour and subsequently quenched with acid to pH 5–6 while warming to room temperature. The mixture was extracted with ether (2x). The organics were combined, washed with water (3x), brine and dried (MgSO$_4$). After filtering, the solvents were evaporated and the crude material was purified on silica (eluent: hexane: CH$_2$Cl$_2$, 1:1 to 100% CH$_2$Cl$_2$) to afford 86.0 g (72%) of 6-trifluoromethanesulfonyloxy-naphthalen-2-yl-methanol as an off-white solid. $^1$H NMR (300 MHz; CDCl$_3$) 2.31 (brs, 1 H), 4.83 (s, 2 H), 7.34 (dd, $J_1$=9.0 Hz, $J_2$=2.0 Hz, 1 H), 7.51 (dd, $J_1$=8.4 Hz, $J_2$=2.0 Hz, 1 H), 7.71 (d, J=2.0 Hz, 1 H), 7.75–7.90 (m, 3 H).

d. 6-Trifluoromethanesulfonyloxy-naphthalene-2-carboxaldehyde.

To a mechanical stirred solution of 6-trifluoromethanesulfonyloxy-naphthalen-2-yl-methanol (70.0 g, 0.228 mol) in CH$_2$Cl$_2$ (600 mL) under an atmosphere of argon was added PCC (54.20 g, 0.25 mol, crushed prior to addition) over a few minutes. After 2 hours the resulting black suspension was poured onto a silica gel column and purified using CH$_2$Cl$_2$ to give a yellow oil that slowly crystallized upon standing to afford 65.1 g (94%) of 6-trifluoromethanesulfonyloxy-naphthalene-2-carboxaldehyde. $^1$H NMR (300 MHz; CDCl$_3$) 7.50 (dd, $J_1$=9.0 Hz, $J_2$=2.0 Hz, 1 H), 7.83 (d, J=2.0 Hz, 1 H), 7.99 (d, J=8.4 Hz, 1 H), 7.07 (dd, $J_1$=9.0 Hz, $J_2$=2.0 Hz, 1 H), 8.12 (d, J=9.0 Hz, 1 H), 8.40 (brs, 1 H), 10.19 (s, 1 H), $^{13}$C NMR (75 MHz, CDCl$_3$) 118.7 (q, J=318 Hz), 119.5, 120.9, 124.5, 129.1, 131.6, 132.2, 133.6, 134.9, 136.4, 148.9, 191.4.

e. 6-(3-Dimethylamino-5,5,8,8-tetramethyl-5,6,7,8-tetrahydro-naphthalen-2-carboxaldehyde.

A mixture of 6-trifluoromethanesulfonyloxy-naphthalene-2-carboxaldehyde (3.0 g, 9.86 mmol), 3-dimethylamino-5,5,8,8-tetramethyl-5,6,7,8-tetrahydronaphthalen-2-yl) boronic acid (2.5 g, 9.08 mmol) and potassium carbonate (2.5 g, 18.1 mmol) in a mixture of toluene (30 mL), EtOH (8 mL) and water (5 mL) was degassed with argon for 60 minutes. Tetrakis(triphenylphosphine) palladium(0) (0.230 g, 0.19 mmol) was added and the mixture heated at reflux under argon overnight. The solution was cooled to room temperature, diluted with ethyl acetate and washed successively with water and brine, dried over anhydrous magnesium sulfate, filtered and evaporated. The residue was chromatographed on silica gel to give 2.5 g of 6-(3-dimethylamino-5,5,8,8-tetramethyl-5,6,7,8-tetrahydro-naphthalen-2-carboxaldehyde (71%). $^1$H NMR (300 MHz; CDCl$_3$): δ 1.31 (s, 6 H), 1.37 (s, 6 H), 1.73 (s, 4 H), 2.55 (s, 6 H), 7.00 (s, 1 H), 7.25 (s, 1 H), 7.90–8.00 (m, 4 H), 8.03 (brs, 1 H), 8.35 (d, J=1.0 Hz, 1 H), 10.17 (s, 1 H).

Example 8

{5-[5-Phenyl-3-methoxy-2-(3-methoxy-5,5,8,8-tetramethyl-5,6,7,8-tetrahydro-naphthalen-2-yl)-benzylidene]-4-oxo-2-thioxo-thiazolidin-3-yl}-acetic acid.

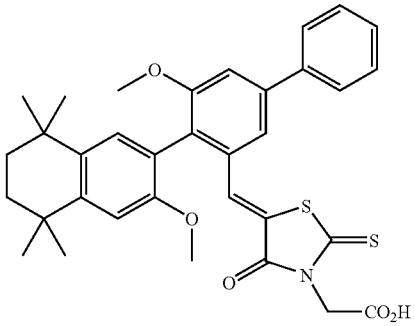

{5-[5-Phenyl-3-methoxy-2-(3-methoxy-5,5,8,8-tetramethyl-5,6,7,8-tetrahydro-naphthalen-2-yl)-benzylidene]-4-oxo-2-thioxo-thiazolidin-3-yl}-acetic acid was prepared in a similar manner as described in Example 1 using 5-phenyl-3-methoxy-2-(3-methoxy-5,5,8,8-pentamethyl-5,6,7,8-tetrahydro-naphthalen-2-yl)benzaldehyde, mp 320+° C., $^1$H NMR (300 MHz; DMSO-$d_6$) (EtOH co-crystallized with title compound) 1.04 (t, EtOH), 1.16 (s, 3 H), 1.18 (s, 3 H), 1.31 (s, 6 H), 1.65 (s, 4 H), 3.43 (q, EtOH), 3.64 (s, 3 H), 3.82 (s, 3 H), 4.39 (AB quartet, J=14.4 Hz, 2 H), 6.97 (d, J=11.4 Hz, 2 H), 7.33 (d, J=3.6 Hz, 2 H), 7.41–7.46 (m, 2 H), 7.54 (t, J=7.3 Hz, 2 H), 7.78 (d, J=7.2 Hz, 2 H). $^{13}$C NMR (75 MHz; in ppm, DMSO-d6): (includes signals for the presence of EtOH) 18.6, 31.5, 31.6, 31.6, 31.9, 33.3, 34.4, 34.7, 34.8, 55.4, 56.0, 108.7, 112.1, 117.8, 120.5, 123.7, 126.8, 128.0, 128.8, 129.1, 130.0, 131.7, 133.4, 135.9, 139.3, 141.1, 145.5, 154.6, 158.0, 166.1, 193.1.

Example 9

{5-[3-Methoxy-2-(3,5,5,8,8-pentamethyl-5,6,7,8-tetrahydro-naphthalen-2-yl)-benzylidene]4-oxo-2-thioxo-thiazolidin-3-yl}-acetic acid.

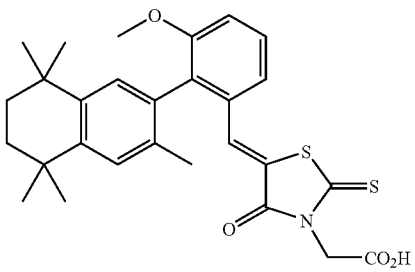

{5-[3-Methoxy-2-(3,5,5,8,8-pentamethyl-5,6,7,8-tetrahydro-naphthalen-2-yl)-benzylidene]-4-oxo-2-thioxo-thiazolidin-3-yl}-acetic acid was prepared in a similar manner as described in Example 1 using 3-methoxy-2-(3,5,5,8,8-pentamethyl-5,6,7,8-tetrahydro-naphthalen-2-yl)benzaldehyde, mp 149° C., $^1$H NMR (300 MHz; DMSO-$d_6$) 1.12 (s, 3 H), 1.17 (s, 3 H), 1.29 (s, 6 H), 1.64 (s, 4 H), 1.92 (s, 3 H), 3.75 (s, 3 H), 4.55 (s, 2 H), 6.88 (s, 1 H), 7.22 (d, 3 H), 7.28 (d, J=8.4 Hz, 1 H), 7.56 (t, J=8.3 Hz, 1 H). $^{13}$C NMR (75 MHz, DMSO-$d_6$): 19.9, 32.3, 34.16, 34.4, 35.3, 56.4, 114.4, 120.7, 123.9, 128.18, 128.30, 129.65, 129.79, 130.1, 132.4, 132.8, 133, 133.5, 134.2, 142.1, 144.4, 157.7, 166.7, 167.9, 194.2.

Example 10

{5-[4-Dimethylamino-3-(3-dimethylamino-5,5,8,8-tetramethyl-5,6,7,8-tetrahydro-naphthalen-2-yl)-benzylidene]-4-oxo-2-thioxo-thiazolidin-3-yl}-acetic acid. (also refered as Compound 10 herein)

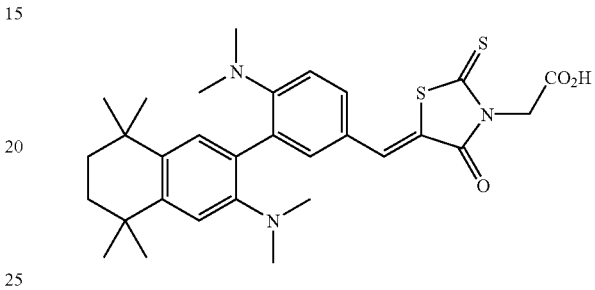

{5-[4-Dimethylamino-3-(3-dimethylamino-5,5,8,8-tetramethyl-5,6,7,8-tetrahydro-naphthalen-2-yl)-benzylidene]-4-oxo-2-thioxo-thiazolidin-3-yl}-acetic acid was prepared in a similar manner as described in Example 1 using 4-dimethylamino-3-(3-dimethylamino-5,5,8,8-tetramethyl-5,6,7,8-tetrahydro-naphthalen-2-yl)benzaldehyde (69% yield), mp 155° C. (dec).

The intermediate 4-dimethylamino-3-(3-dimethylamino-5,5,8,8-tetramethyl-5,6,7,8-tetrahydro-naphthalen-2-yl)benzaldehyde was prepared as follows:

a. 2-Nitro-5,5,8,8-tetramethyl-5,6,7,8-tetrahydro-naphthalene.

A mixture of 45 mL concentrated nitric acid (0.690 mol, 1.43 eq.) and 74 mL concentrated sulfuric acid (1.39 mol, 2.86 eq.) was placed in a round bottom flask equipped with a mechanical stirrer and cooled to −10° C. (ice/salt bath 3:1). 1,1,2,2-tetramethyl-1,2,3,4-tetrahydro-naphthalen (91 g, 0.483 mol) was added in portions. After the addition was complete, the resulting reaction mixture was stirred for 1.5 hrs. The mixture was partitioned between water and dichloromethane and the aqueous phase was extracted with dichloromethane. The combined organic phases were washed with 1N NaOH, water, 10% citric acid, brine, dried over sodium sulfate, filtered and evaporated to give an oil which crystallized upon standing overnight. The crystals were collected by filtration, washed with cold methanol and dried to afford 80.23 g 2-Nitro-5,5,8,8-tetramethyl-5,6,7,8-tetrahydronaphthalene (63%). $^1$H-NMR (300 MHz, CDCl$_3$): 1.31 (s, 6 H), 1.33 (s, 6 H), 1.73 (s, 4 H), 7.44 (d, J=9.0 Hz, 1 H), 7.94 (dd, J=2.7, 9.0 Hz, 1 H), 8.17 (d, J=2.4 Hz, 1 H).

b. 2-Dimethylamino-5,5,8,8-tetramethyl-5,6,7,8-tetrahydro-naphthalene.

To a solution of 2-nitro-5,5,8,8-tetramethyl-5,6,7,8-tetrahydro-naphthalene (79.0 g, 0.339 mol) in dichloromethane as added 1 g of 10% palladium on carbon and the mixture was hydrogenated at 40–50 psi of hydrogen for 20 hrs. The catalyst was removed by filtration and the organic and the aqueous layers were separated. The aqueous layer was made alkaline by addition of 1N NaOH and extracted with dichloromethane. The combined organic phases were dried over sodium sulfate, filtered and evaporated to give 2-amino-5, 5,8,8-tetramethyl-5,6,7,8-tetrahydro-naphthalene as a red-orange solid which was used in the next step without further purification.

To a solution of 2-amino-5,5,8,8-tetramethyl-5,6,7,8-tetrahydronaphthalene (70.10 g, 0.345 mol) and formaldehyde (280 mL, 10 eq) in 2 L of acetonitrile cooled to 0° C. was added sodium cyanoborohydride (65 g, 3 eq.) in portions while maintaining the temperature between 10–20° C. Glacial acetic acid was added to adjust the pH to 7. The reaction was stirred for 2 hrs at room temperature and the resulting mixture was partitioned between 1N NaOH and EtOAc, the organic phase was washed with water and brine, dried over sodium sulfate, filtered and evaporated. Chromatography on silica gel (hexanes/EtOAc 95:5) gave 54.90 g (70%, 2 steps) of 2-dimethylamino-5,5,8,8-tetramethyl-5,6,7,8-tetrahydronaphthalene. $^1$H-NMR (300 MHz, CDCl$_3$): 1.25 (s, 6 H), 1.29 (s, 6 H), 1.66 (s, 4 H), 2.91 (s, 6 H), 6.62 (dd, J=3.0 Hz, J=8.7 Hz, 1 H), 6.67 (d, J=2.7 Hz, 1 H), 7.19 (d, J=8.7 Hz, 1 H).

c. 2-Bromo-3-dimethylamino-5,5,8,8-tetramethyl-5,6,7,8-tetrahydronaphthalene.

To a solution of 2-dimethylamino-5,5,8,8-tetramethyl-5,6,7,8-tetrahydronaphthalene (55.0 g, 0.238 mol) in 350 mL of glacial acetic acid was added drop wise over 20 minutes a solution of 12.3 mL of bromine (1 eq.) in 15 ml of glacial acetic acid. After stirring for 2 hrs, the resulting mixture was evaporated. The residue was dissolved in EtOAc and washed with water, saturated sodium bicarbonate solution, brine, dried over sodium sulfate, filtered and evaporated. The residue was purified by column chromatography (silica gel, hexanes/EtOAc, 95:5) to afforded 66.63 g (90%) of product 2-Bromo-3-dimethylamino-5,5,8,8-tetramethyl-5,6,7,8-tetrahydro-naphthalene. $^1$H-NMR (300 MHz, CDCl$_3$): 1.25 (s, 6 H), 1.27 (s, 6 H), 1.65 (s, 4 H), 2.78 (s, 6 H), 6.99 (s, 1 H), 7.43 (s, 1 H).

d. (3-Dimethylamino-5,5,8,8-tetramethyl-5,6,7,8-tetrahydro-naphthalen-2-yl) boronic acid.

To a solution of 2-Bromo-3-dimethylamino-5,5,8,8-tetramethyl-5,6,7,8-tetrahydronaphthalene (67.08 g, 0.216 mol) in 300 mL of anhydrous THF at −78° C. was added dropwise at −78° C. a 1.6 molar solution of n-butyl lithium (1.6 M, 203 mL, 1.5 eq.) over a period of 30 minutes. The reaction was stirred for 10 min. at −78° C. and 150 ml of tri(iso-propyl) borate (3 eq.) was added dropwise over 0.5 hr. The mixture was allowed to warm to room temperature overnight. The resulting thick mixture was diluted with THF, cooled to 0° C. and 1N hydrochloric acid was added. The reaction was stirred for 0.5 hr at room temperature. The resulting layers were separated and the aqueous phase was washed with EtOAc. The aqueous layer was neutralized to pH 7 to give a precipitate that was extracted with dichloromethane. The aqueous phase was saturated with sodium chloride and extraction was continued. The combined organic layers were dried over sodium sulfate, filtered and evaporated to yield an oil which slowly crystallized on standing. The solid was collected by filtration, washed with hexane and dried to afford 23.00 g of (3-dimethylamino-5,5,8,8-tetramethyl-5,6,7,8-tetrahydronaphthalen-2-yl) boronic acid (39%). $^1$H-NMR (300 MHz, DMSO-d$_6$): 1.20 (s, 6 H), 1.23 (s, 6 H), 1.60 (s, 4 H), 2.62 (s, 6 H), 7.25 (s, 1 H), 7.64 (s, 1 H), 9.14 (s, 2 H).

e. 3-bromo-4-(dimethylamino) benzaldehyde

To a solution of 4-(dimethylamino)-benzaldehyde (10.0 g, 67.03 mmol) in dichloromethane (250 mL) was added pyridinium tribromide (21.4 g, 67.03 mmol). The reaction mixture was stirred at room temperature overnight. The solution was washed successively with water and brine, dried over anhydrous magnesium sulfate, filtered and evaporated. Chromatography on silica gel (15% EtOAc in hexane) afforded 14.06 g of 3-bromo-4-(dimethylamino)-benzaldehyde (92%).

f. 3-(3-Dimethylamino-5,5,8,8-tetramethyl-5,6,7,8-tetrahydronaphthalen-2-yl)-4-dimethylaminobenzaldehyde.

To a degassed mixture of (3-dimethylamino-5,5,8,8-tetramethyl-5,6,7,8-tetrahydronaphthalen-2-yl) boronic acid (260 mg, 0.945 mmol), 3-bromo-4-(dimethylamino) benzaldehyde (216 mg, 1 eq.) and potassium carbonate (520 mg, 4 eq.) in 30 mL dimethyl ethyleneglycol and 2.3 ml of water was added 55 mg (0.05 eq.) of tetrakis(triphenylphosphine)palladium(0) and the reaction was heated to reflux for 24 hrs. The mixture was partitioned between water and EtOAc, the organic phase was washed with water, brine, dried over sodium sulfate, filtered and evaporated. The residue was purified by column chromatography (silica gel, hexanes/EtOAc 95:5) to afford 187 mg of product 3-(3-dimethylamino-5,5,8,8-tetramethyl-5,6,7,8-tetrahydronaphthalen-2-yl)-4-dimethylaminobenzaldehyde (52%). $^1$H-NMR (300 MHz, CDCl$_3$): 1.23 (s, 6 H), 1.31 (s, 6 H), 1.68 (s, 4 H), 2.53 (s, 6 H), 2.71 (s, 6 H), 6.91 (s, 1 H), 6.93 (d, J=8.5 Hz, 1 H), 7.18 (s, 1 H), 7.71 (dd, J=2.0, J=9.1 Hz, 1 H), 7.84 (d, J=2.0 Hz, 1 H).

Example 11

Rhodanine-3-acetic acid Library Procedure

The compounds recited in the examples above were synthesized in a traditional manner and not as a mixture of compounds. The building blocks used in the synthesis of a library of compounds were prepared using procedures similar to those described above, or, similar libraries of related substituted heterocyclic compounds can be produced by these or other alternative chemical reaction steps known by one skilled in the art. In the current example, the boronic acids and benzaldehyde bromides/iodides/chlorides or triflates are shown below along with their respective codes that were employed during the synthesis of a combinatorial library of the compounds of the invention:

Boronic Acids:

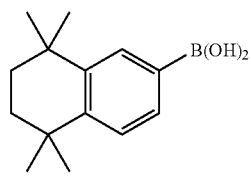

A1

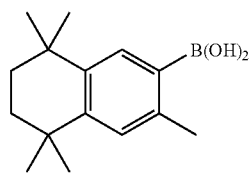

A2

-continued
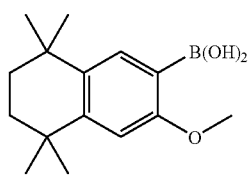
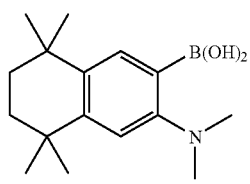
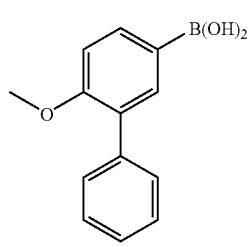
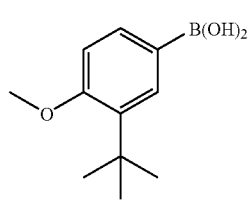
Benzaldehydes:
Bromides/Iodides/Chlorides:
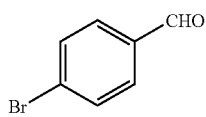
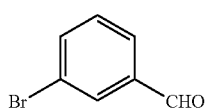
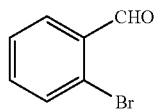
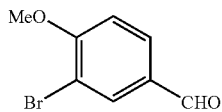
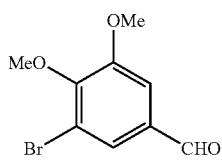
-continued
A3
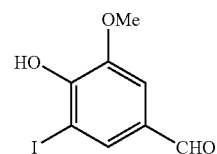
A4
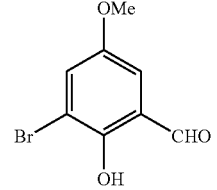
A7
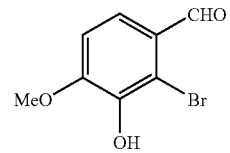
A10
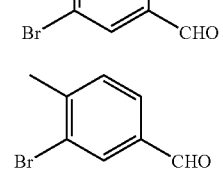
B1
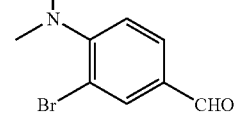
B2
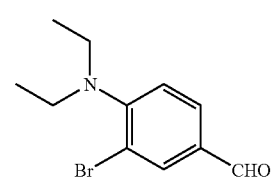
B3
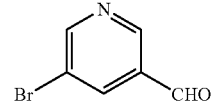
B4
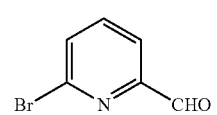
B5
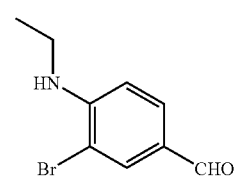
B6
B7
B8
B23
B24
B25
B26
B27
B28
B29

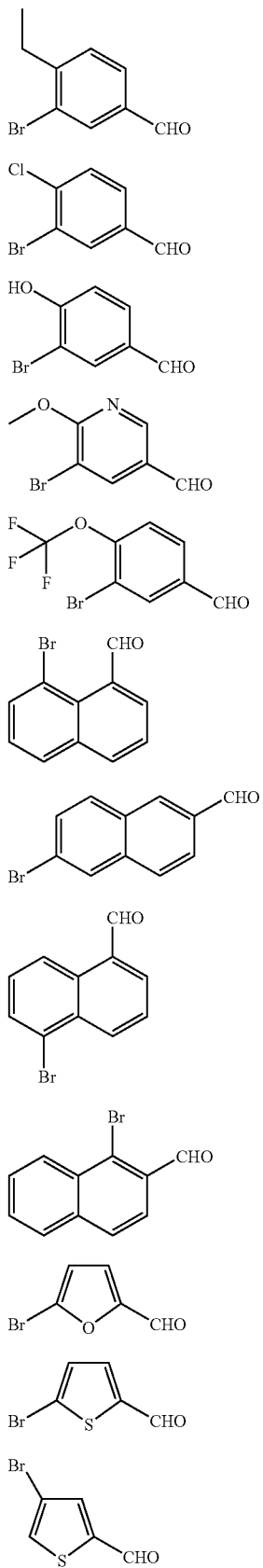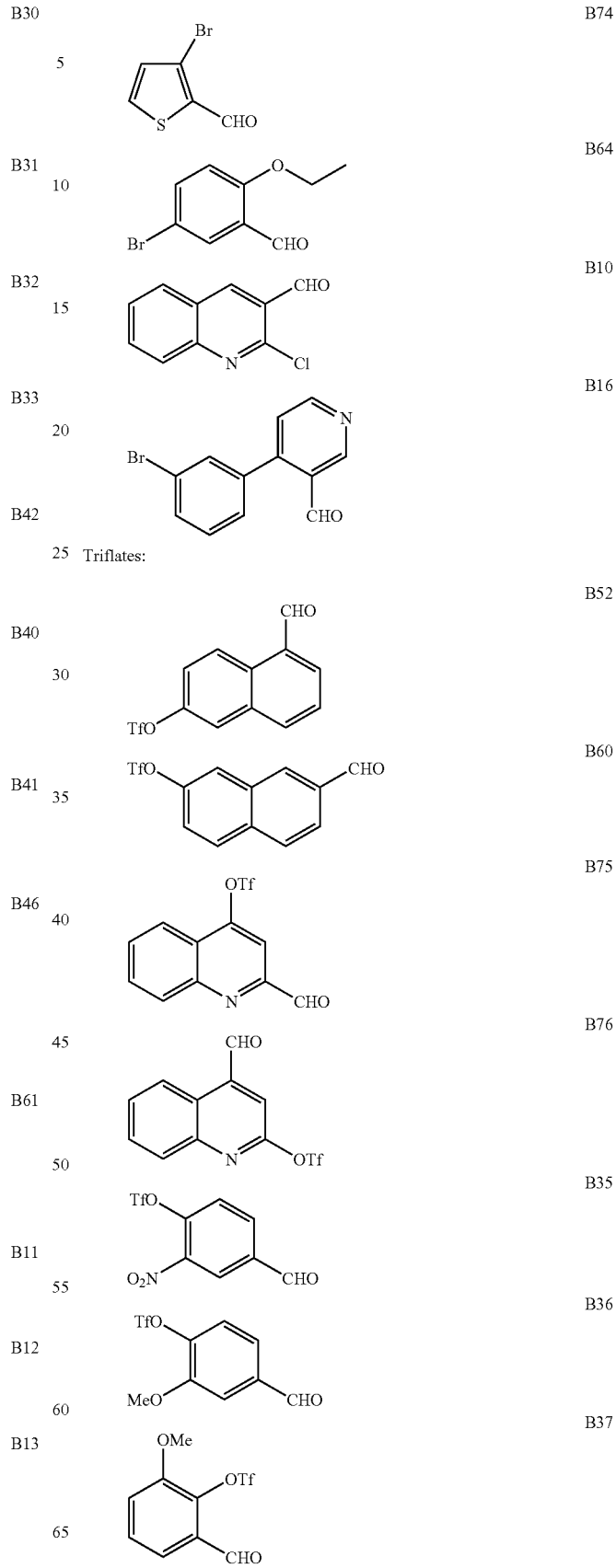
Triflates:

-continued

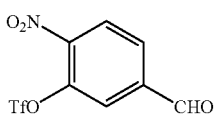
B39

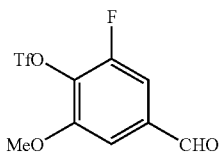
B43

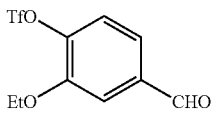
B44

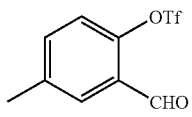

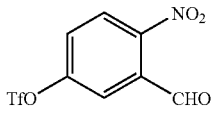
B47

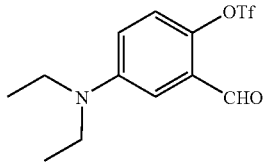
B50

N-Substituted heterocycle:

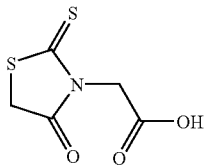
C1

1) Suzuki Coupling Step

A solution of 0.225 mmol of a boronic acid, (0.150 mmol) of aldehyde, and 62.2 mg (0.450 mmol) of $K_2CO_3$ in 1.0 mL of toluene and 0.5 mL of ethanol-water (1.2:1) was degassed with argon in a glove bag for three times and was then treated with a solution of 11.8 mg (0.010 mmol) of Tetrakis (triphenylphosphine)-palladium (0) in 0.5 mL of toluene at RT. The reaction was then heated at 85° C., with vigorous shaking or stirring, for a period of 16 hr under argon atmosphere. The reaction was cooled down to RT, dried over anhydrous $Na_2SO_4$, and purified by a short silica gel column (1 cm diameter and 3 cm length). The column was eluted with 2 mL of toluene and 3 mL of 60% EtOAc in hexane sequentially. The combined eluents were concentrated under reduced pressure to give relative pure desired product which was used in the next step directly.

2) Knoevenagel Condensation Step

The coupling product from the Suzuski step was dissolved in 1.5 mL of toluene and approximately 0.5 mL was added to a reaction was vial. The reaction vial was treated with 8.6 mg (0.045 mmol) of rhodanine-3-acetic acid (C1), and 0.005 mmol of piperidinium acetate or 0.15 mmol of ammonium acetate. The resulting reaction mixture was heated at 80° C. for 3 hr and cooled to room temperature to form a suspension. The solids that precipitated upon cooling were typically desired products with very high purity. The oily products with relative low purity could be further purified by chromatography.

3) Quality Control of the Library

Mass Spectra Analysis Conditions Used in QC:
Flow Injection Analysis (FIA) mass spectrometry
Period: 1 minute
Ionization: pneumatically ($N_2$) assisted electrospray
Polarity: negative
Mobile phase: methanol, HPLC grade
Flow rate: 300 μL/min
Injection volume: 10 μl
HPLC Analysis Conditions Used in QC:
HPLC system: Shimazu VP series
Column: C-18
Mobile phase: $H_2O/CH_3CN$/Formic acid ($CH_3CN$ gradient from from 15% to 100%)
Detector: ELSD
Run time: 3.5 to 4.5 min.

Examples of quality control data used in the acquisition of the compounds are shown below:

Examples of QC Data

| Product | Compound # | Mass | Confirmed Mass, [M-H] | HPLC Purity |
|---|---|---|---|---|
| A1B6C1 | 11 | 511.15 | Yes | 82% |
| A1B11C1 | 12 | 455.12 | Yes | 100% |
| A1B16C1 | 13 | 542.17 | Yes | 77% |
| A1B27C1 | 14 | 466.14 | Yes | 77% |
| A1B28C1 | 15 | 466.14 | Yes | 100% |
| A1B32C1 | 16 | 481.14 | Yes | 100% |
| A1B50C1 | 17 | 536.22 | Yes | 70% |
| A1B65C1 | 18 | 483.13 | Yes | 85% |
| A1B72C1 | 19 | 522.20 | Yes | 86% |
| A1B75C1 | 20 | 516.15 | Yes | 100% |
| A2B6C1 | 21 | 525.16 | Yes | 81% |
| A2B11C1 | 22 | 469.14 | Yes | 98% |
| A2B31C1 | 23 | 513.12 | Yes | 71% |
| A2B33C1 | 24 (also 3) | 510.16 | Yes | 72% |
| A2B35C1 | 25 | 524.14 | Yes | 100% |
| A2B52C1 | 26 | 529.17 | Yes | 73% |
| A2B63C1 | 27 | 525.16 | Yes | 81% |
| A2B65C1 | 28 | 497.15 | Yes | 69% |
| A2B67C1 | 29 | 518.17 | Yes | 73% |
| A2B75C1 | 30 | 530.17 | Yes | 100% |
| A3B5C1 | 31 | 555.17 | Yes | 91% |
| A3B6C1 | 32 | 541.16 | Yes | 91% |
| A3B11C1 | 33 | 485.13 | Yes | 100% |
| A3B23C1 | 34 | 539.18 | Yes | 68% |
| A3B25C1 | 35 | 538.20 | Yes | 94% |
| A3B27C1 | 36 | 496.15 | Yes | 100% |
| A3B61C1 | 37 | 545.17 | Yes | 94% |
| A3B71C1 | 38 | 552.21 | Yes | 69% |
| A3B72C1 | 39 | 552.21 | Yes | 96% |
| A3B75C1 | 40 | 546.16 | Yes | 96% |
| A4B4C1 | 41 | 538.20 | Yes | 83% |
| A4B11C1 | 42 | 498.16 | Yes | 97% |
| A4B27C1 | 43 | 509.18 | Yes | 86% |
| A4B28C1 | 44 | 509.18 | Yes | 98% |
| A4B29C1 | 45 | 551.23 | Yes | 99% |
| A4B33C1 | 46 | 539.19 | Yes | 72% |
| A4B64C1 | 47 | 552.21 | Yes | 76% |
| A4B66C1 | 48 | 568.21 | Yes | 74% |
| A4B75C1 | 49 | 559.20 | Yes | 75% |
| A4B76C1 | 50 | 559.20 | Yes | 66% |
| A7B4C1 | 51 | 491.09 | Yes | 71% |
| A7B5C1 | 52 | 521.10 | Yes | 72% |
| A7B6C1 | 53 | 507.08 | Yes | 96% |

-continued

Examples of QC Data

| Product | Compound # | Mass | Confirmed Mass, [M-H] | HPLC Purity |
|---|---|---|---|---|
| A7B11C1 | 54 | 451.05 | Yes | 93% |
| A7B23C1 | 55 | 505.10 | Yes | 77% |
| A7B25C1 | 56 | 504.12 | Yes | 91% |
| A7B27C1 | 57 | 462.07 | Yes | 92% |
| A7B28C1 | 58 | 462.07 | Yes | 97% |
| A7B31C1 | 59 | 495.04 | Yes | 91% |
| A7B39C1 | 60 | 506.06 | Yes | 92% |
| A10B25C1 | 61 | 484.15 | Yes | 80% |
| A10B31C1 | 62 | 475.07 | Yes | 79% |
| A10B35C1 | 63 | 486.09 | Yes | 100% |
| A10B39C1 | 64 | 486.09 | Yes | 81% |
| A10B57C1 | 65 | 455.12 | Yes | 94% |
| A10B61C1 | 66 | 491.12 | Yes | 83% |
| A10B64C1 | 67 | 485.13 | Yes | 100% |
| A10B65C1 | 68 | 459.10 | Yes | 95% |
| A10B66C1 | 69 | 501.13 | Yes | 100% |
| A10B75C1 | 70 | 492.12 | Yes | 100% |

Screening:

A compound prepared in the manner described herein can be screened for lipid metabolism, such as, for example, in Sprague Dawley Rats on a high cholesterol atherogenic diet as set forth in Example 12 or in an in vitro assay, such as, for example to measure the ability of a compound to inhibit adipocyte differentiation induced by the PPARγ agonist rosiglitazone (BRL49653) as setforth in Example 14 or to inhibit nuclear receptor regulating lipid or carbohydrate uptake, synthesis or metabolism as set forth in Example 13, or a compound can be screened using all of the above. A compound can also be screened for anticancer, such as, for example, the inhibition of AKT activity as setforth in Example 16, or the inhibition of cell proliferation in cancer cell lines treated in the presence of the compound as set forth in Example 15.

Example 12

Oral Administration of Compound 7 in the Treatment of Hypercholesterolemia in Sprague Dawley Rats Maintained on a High Cholesterol Atherogenic Diet Methods Animals and Housing Six week-old male Sprague Dawley rats (HSD, Harlan) were housed in a fixed 12–12-hr artificial light-dark cycle, and maintained on a high cholesterol, atherogenic diet ad libitum (# C13002, Research Diets, New Jersey).

Animals were maintained on this diet throughout the course of the study.

Dosage Groups and Treatment

Following six days of maintenance on the high cholesterol diet, the animals were bled from the tail vein (100–200 μL of whole blood) and serum levels of total cholesterol were measured in duplicate (Infinity Cholesterol Kit; Sigma, St. Louis, Mo.). Based on these initial measures, animals were sorted into groups with approximately the same average serum cholesterol levels. Once sorted, the animals were housed three per cage and maintained on the high cholesterol diet ad libitum.

Experiment I: (Compound 7)
Treatment groups (n=6/group):
1) High cholesterol fed control (sesame oil)
2) Compound 7 (20 mg/kg; once daily)

Compound 7 was mixed in sesame oil, and administered to animals in a volume of 3 mL/kg/dose. Compound 7 was administered by oral gavage daily for five consecutive days.

Serum Measurements

Figure 2:
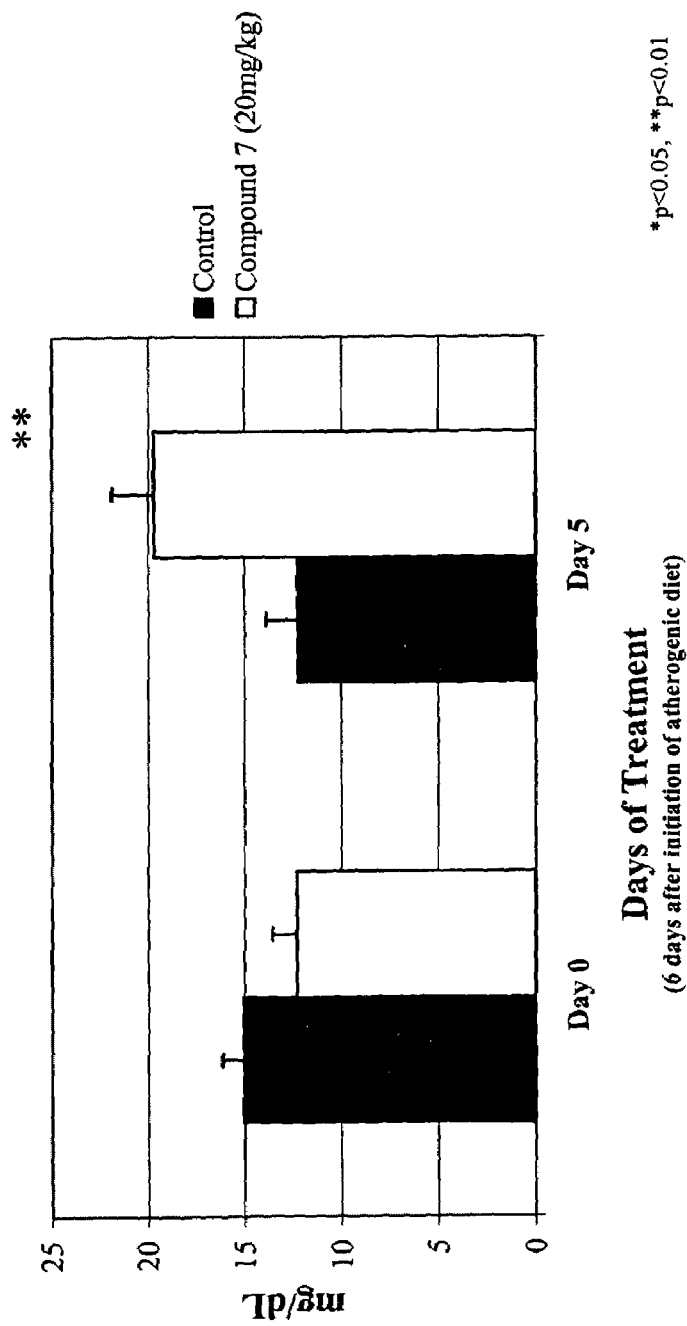
FIG. 2 shows the HDL cholesterol levels in HSD Rats maintained on an atherogenic diet after treatment with Compound 7.
Figure 3:
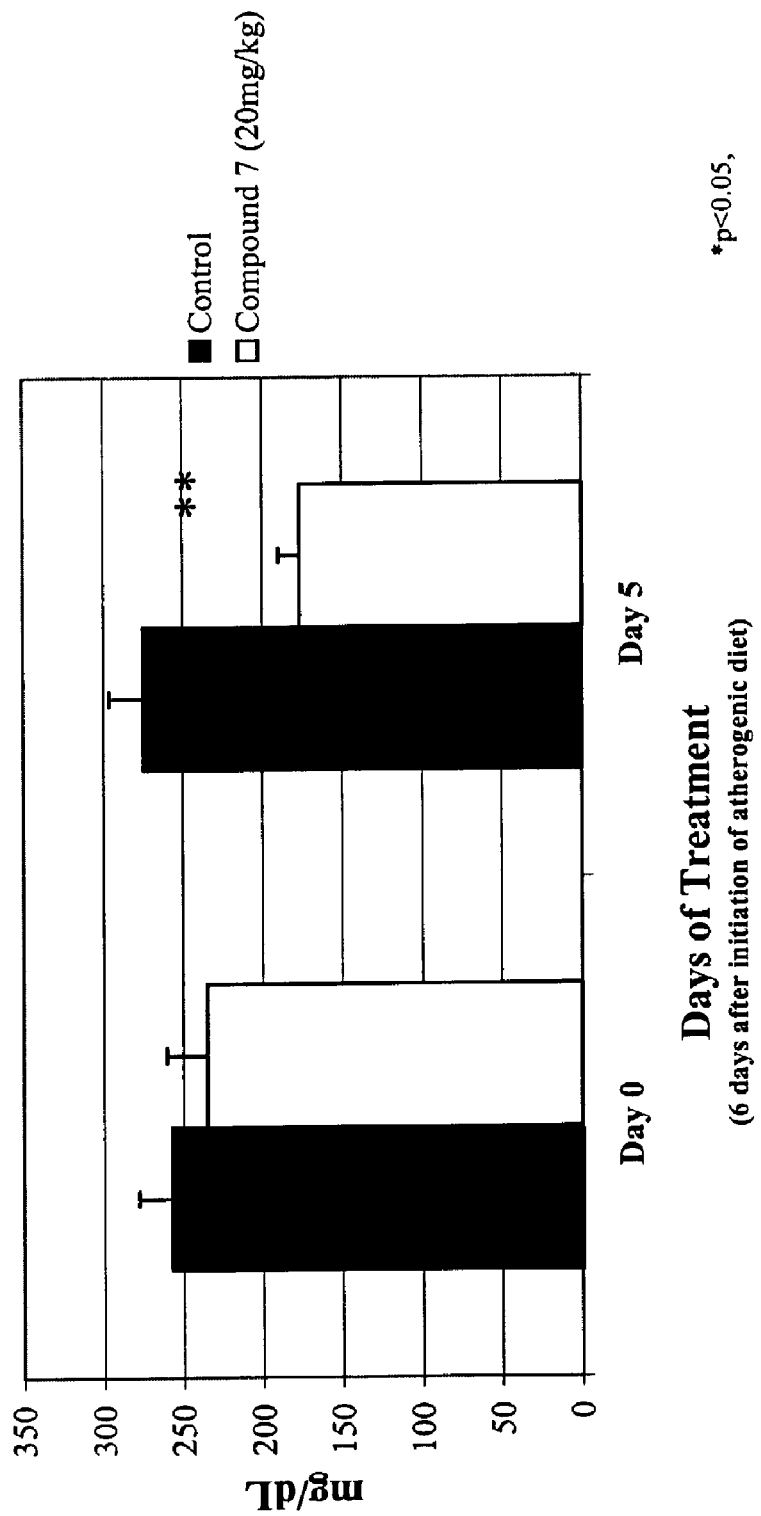
FIG. 3 shows the LDL cholesterol levels in HSD Rats maintained on an atherogenic diet after treatment with Compound 7.

To monitor the effect of Compound 7, animals were bled from the tail vein five days after commencement of oral treatment. Serum cholesterols were measured in duplicate. The blood is kept at room temperature to allow coagulation, after which the serum is separated and assayed for total cholesterol (see FIG. 1), high density lipoprotein cholesterol (see FIG. 2) and low density lipoprotein cholesterol levels (see FIG. 3). Compound 7 significantly reduced total serum cholesterol compared to control animals maintained on the same atherogenic diet (ANOVA, Fisher's Least significant difference test, $p \leq 0.01$). Similarly, Compound 7 reduced LDL cholesterol levels compared to controls (ANOVA, Fisher's Least significant difference test, $p \leq 0.01$). Finally, Compound 7 increased HDL cholesterol levels compared to controls (ANOVA, Fisher's Least significant difference test, $p < 0.01$).

Example 13

In Vitro Transactivation Screening

In vitro screens such as the transactivation assay can be used to measure the ability of a compound to inhibit a nuclear receptor regulating lipid or carbohydrate uptake, synthesis or metabolism. In the assay described herein compounds can be identified that can inhibit activation of the following nuclear receptors: LXR, PPARα, PPARγ and FXR. This activity can be useful to treat lipid disorders such as hypercholesteremia and obesity.

Cell line: Kidney Green Monkey CV-1 cells.

Growing culturing medium: Dulbecco's modified Eagle's medium (DMEM) supplememnted with 10% fetal calf serum (FCS).

Procedure: CV-1 cells were plated in 48 well-plate culture plates, at a density of 10,000 cells/well, 24 h prior to transfection. One to three hours before transfection, cells were fed with fresh medium. A modified calcium phosphate precipitation procedure was used for transient transfection (Pfahl, M. et al., 1990, Methods in Enzymology 189: 256).

Typically, 40 ng reporter plasmid and 20 ng of each receptor expression vector were mixed, together with 10 ng of β-galactosidase control plasmid (pCH110, Pharmacia, Piscataway, N.J.) and Bluescript plasmid to obtain a total of 400 ng DNA per well. To this mixture 1 μl of 2.5M $CaCl_2$ and 10 μl of BBS buffer, pH 6.95, were added afterward. The reaction mixtures were then incubated at room temperature for 20 minutes, which allowed for a fine precipitate to be formed. Twenty microliters of each reaction mixture were dispatched per well, followed by incubation at 37° C. and 3% $CO_2$ for approximately 20 hours. The medium was then exchanged with DMEM containing 10% charcoal-treated FCS, with or without ligands. To test for potential antagonism, various concentrations of the putative antagonist were added together with 1 μM of a specific receptor agonist, such as T0901317 (Repa J. J. et al, 2000 Science 289:1524) for Gal-LXR, and rosiglitazone (BRL49653) for Gal-PPARγ. Incubation was continued for 24 hours at 37° C. and regular 6% $CO_2$. After that time, cells were washed with Dulbecco's phosphate buffer saline (PBS), and lysed with 50 μL/well of Lysis buffer from Dual-Light System (Applied Biosystems, Bedford, Mass.). Cellular extracts obtained were assayed for Luciferase and β-galactosidase activities following the instructions from the Dual-Light System kit.

Plasmids:

Reporter: TK-(MH100)$_4$-LUC (UAS-Luc)

Receptors: Gal4 chimeras were used, which contained the ligand binding domain of the various receptors fused to the C-terminal end of the yeast Gal4 DNA binding domain.

BBS buffer: 50 mM N,N-bis(2-hydroxyethyl)-2-aminoethanesulfonic acid, 250 mM NaCl, 1.5 mM Na$_2$HPO$_4$, pH 6.95.

Figure 12:
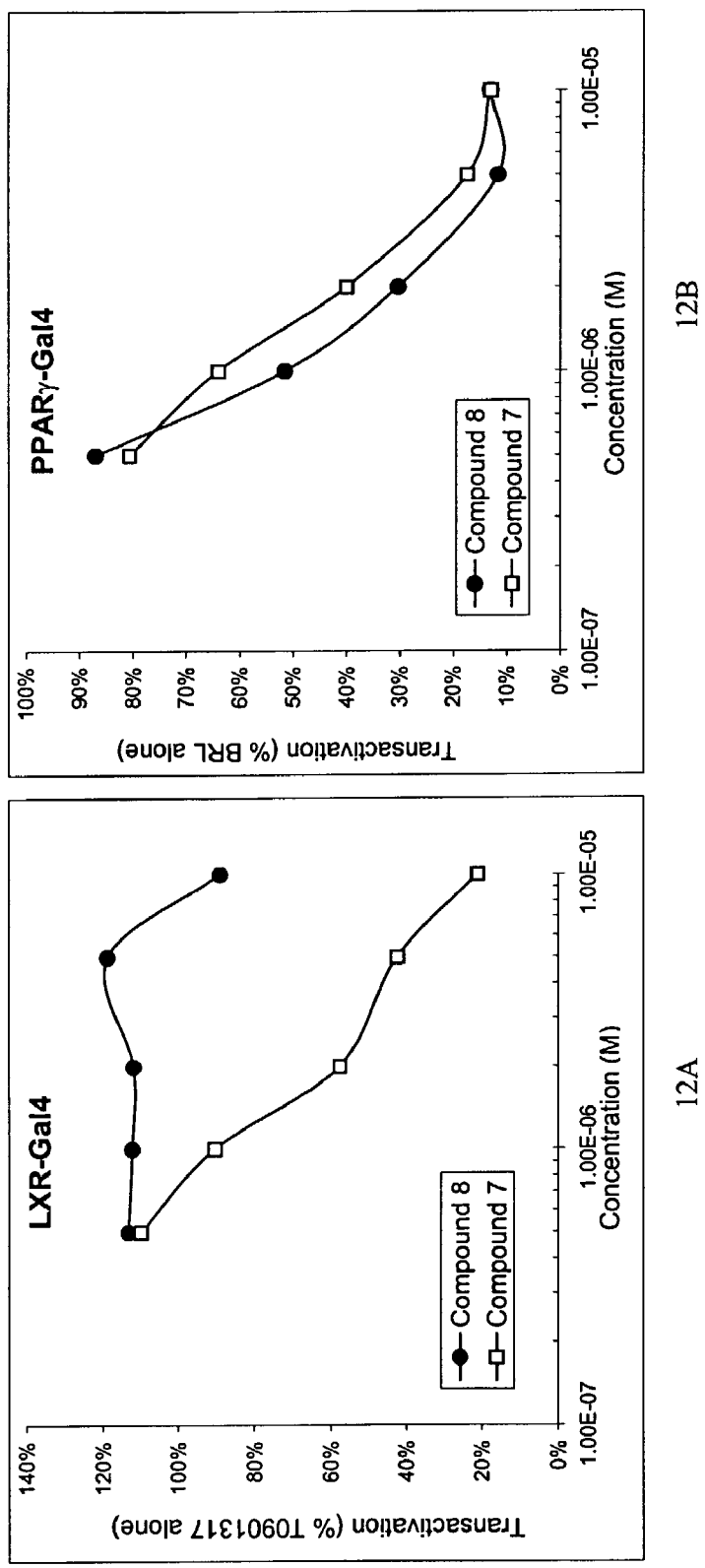
FIG. 12 shows antagonism of T0901317-dependent activation of LXR and BRL49653-dependent activation of PPARγ by the compounds of the invention.

Results plotted in FIG. 12 show the inhibitory activity of compounds 8 and 7 on T0901317-induced LXR activation and BRL49653-induced PPARγ activation. As demonstrated in FIG. 12 Compound 8 has the ability to only antagonize the activation activity of BRL49653 for PPARγ, while Compound 7 has the potential to antagonize both LXR as well as PPARγ activation. Compound 8 and Compound 7 antagonized these receptors in a dose-dependent fashion reaching inhibition values of ~80–90% at 10 μM.

Example 14

Figure 11:
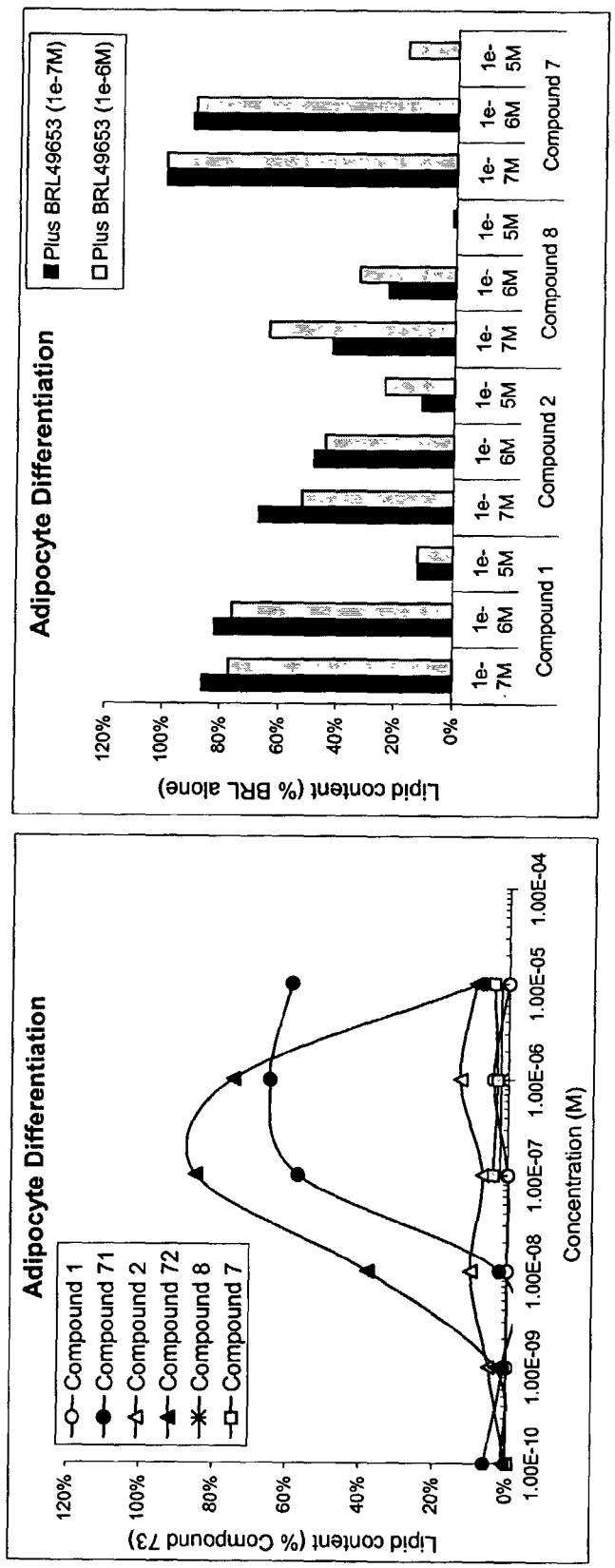
FIG. 11 shows the profile of adipocyte differentiation displayed when 3T3-L1 cells were treated with the compounds of the invention by themselves or in the presence of rosiglitazone (BRL49653).

In Vitro Screening 3T3-L1 Differentiation (see FIG. 11)

The mouse preadipocyte cell line 3T3-L1 has been extensively used to study adipocyte differentiation. Upon stimulation with differentiating agents, preadipocytes typically undergo one cell cycle expansion and then they are growth arrested and dramatically change their shape to become more rounded cells, loaded with lipids, in a fashion closely reflecting adipogenesis in vivo. In this well-known process of differentiation, peroxisome proliferator activated receptor gamma (PPARγ) and retinoid X receptor (RXR) play a key role. PPARγ binds as an obligatory heterodimer with RXR to specific responsive sequences in the promoter region of target genes. In the particular case of PPARγ/RXR heterodimers, both receptors can be activated via their specific ligands. As a consequence of such activation, adipocyte-specific genes are turned on (C/EBP, aP2, LPL, adipsin, etc) and adipocyte differentiation results. Because lipid accumulation is the endpoint of adipocyte differentiation, the quantification of lipids which have accumulated in cells upon treatment with the compound(s) of interest, will indicate the ability of that compound to trigger adipocyte differentiation. More importantly, the potency of that compound can be estimated as well based on the total amount of lipids accumulated. The amount of lipid measured at the end of the assay for each tested compound is here compared to that of Compound 73 at 0.1 μM, which is considered 100% (see FIG. 11A).

In the particular case of measuring the potential antagonistic activity of some compounds, the putative antagonist is combined together with an agonist (such as the PPARγ agonist BRL49653). Thus, the amount of lipids accumulated in response to BRL49653 (considered as 100% in this case), is decreased by the compound with antagonistic activity (see FIG. 11B).

The compounds can function, for example, as antidiabetic molecules and modulators of lipid metabolism and will have the ability to increase lipid content (by inducing differentiation of 3T3-L1 cells), and/or can function as antiobesity/carbohydrate and/or lipid metabolism modulators. Other compounds such as those compounds which inhibit certain nuclear receptor activates, described herein, can be identified by measuring their ability to inhibit 3T3 L1 adipocyte differentiation induced in the presence of, for example, the PPARγ agonist rosiglitazone (BRL49653). Such antagonists can serve and function as antiobesity and lipid lowering drugs.

Materials and Methods: Mouse embryo fibroblast 3T3-L1 cell line, from American Type Culture Collection (ATCC), was used as a model of adipocyte differentiation.

Culture Conditions:

Growing medium (GM): DME Dulbecco's modified Eagle's medium containing 4500 mg/L glucose; 4 mM L-glutamine; 10 U/ml Pen-G; 10 mcg/ml and 10% Calf Serum (CS).

Differentiation medium (DM): DME Dulbecco's modified Eagle's medium containing 4500 mg/L glucose; 4 mM L-glutamine; 10 U/ml Pen-G; 10 mcg/ml and 10% Fetal Calf Serum (FCS). Cells are always kept at 10% CO$_2$.

Procedure

Cells were seeded at 3,000 cells/well in 96 well-tissue culture plates in growing medium.

Two days after reaching confluence, cells were treated with the different compounds of interest in DM (Day 0). Drugs were replaced every 2–3 days in DM. Differentiation was assessed after 7 days of treatment, by measuring the lipid content in the cells, using the Triglyceride (INFINITY) reagent (Quantitative assay).

Controls: All cells, including control cells (vehicle), are treated with the same volume of dimethyl sulfoxide (DMSO) never exceeding 0.1% final solvent concentration. As a positive control for differentiation, cells were treated with 10 μg insulin per ml and 2.5 μM dexamethasone (Ins/Dex).

FIG. 11 shows the lipid content profile of 3T3-L1 cells treated with Compounds 1 and 2, which are N-alkylated heterocycles of the invention, in comparison with compounds 71 and 72, which are similar but not N-alkylated and outside the scope of the invention, at concentrations ranging from 1e-10M to 1e-5M.

Compound 73

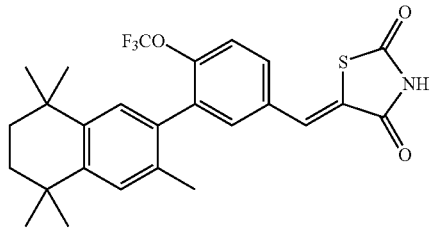

Compound 1

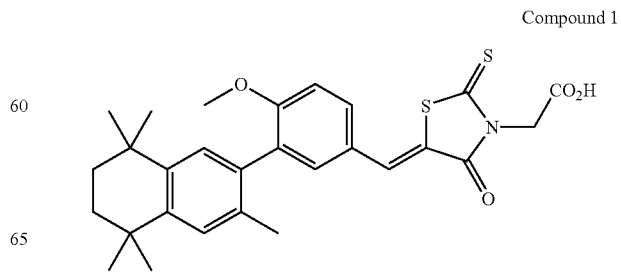

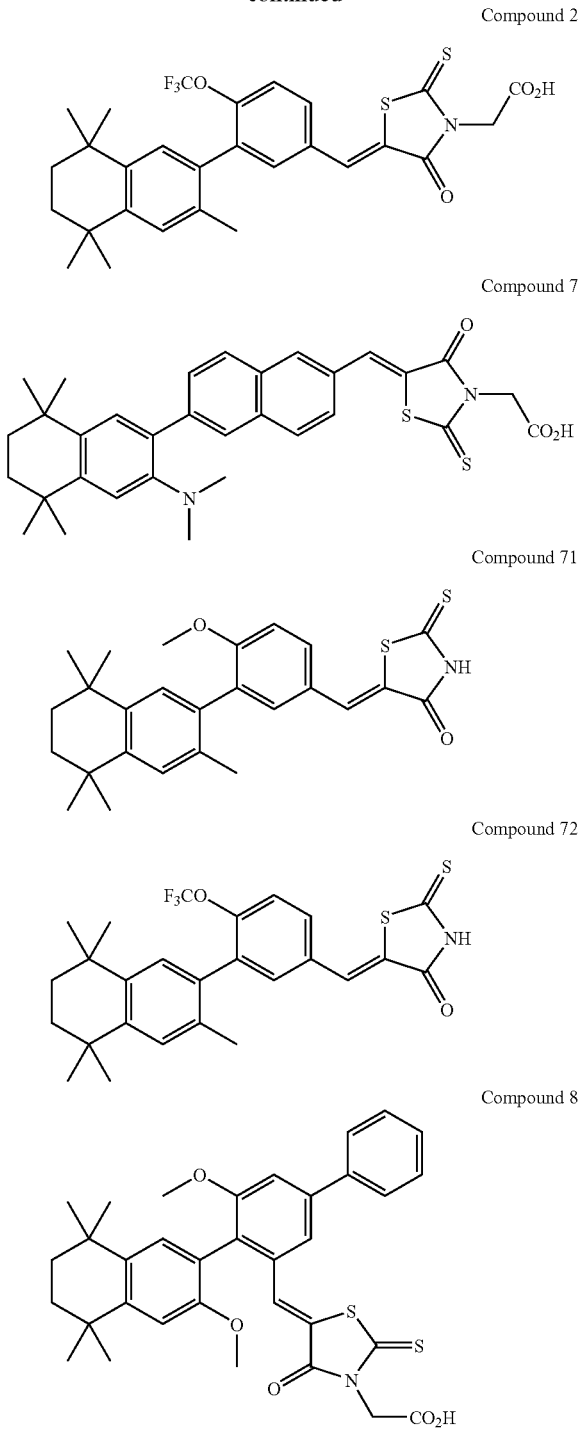

-continued

Compound 2

Compound 7

Compound 71

Compound 72

Compound 8

Surprisingly, while compounds 71 and 72 induced lipid accumulation in these cells, the analogous N-alkylated compounds 1 and 2 lacked that ability, as shown in FIG. 11A. Moreover, when compounds 1 and 2 were tested in combination with the known PPARγ agonist rosiglitazone (BRL49653), as shown in FIG. 11B, they unexpectedly and potently inhibited the adipocyte differentiation induced by rosiglitazone in a dose-dependent manner. The same phenomenon was observed with other N-alkylated compounds such as Compounds 7 and 8, which also lacked the ability to differentiate 3T3-L1 cells by themselves, but in combination with rosiglitazone, strongly inhibited the lipid accumulation triggered by the PPARγ agonist rosiglitazone. These results illustrate the changes in the structure of these compounds caused by N-alkylation of the heterocycles results in new useful and unexpected biological activities.

Example 15

In Vitro Screening of Compounds for Anti-Cancer Activity (see FIG 13)

Materials and Methods:
The compounds of the invention were screened as anti-cancer drug candidates for the following human cancer cell lines:
One lung cancer cell line (A549)
One breast cancer cell line (MDA-MB-468)
One prostate cancer cell line (PC-3)
One pancreatic cancer cell line (Bx-PC3)
All cell lines were purchased from American Type Culture Collection (ATCC).

Culture Conditions:
A549 cells and MDA-MB-468 were grown in DME Dulbecco's modified Eagle's medium containing 4500 mg/L glucose; 4 mM L-glutamine; 10 U/ml Pen-G; 10 mcg/ml and 10% fetal calf serum (FCS).
PC-3 and Bx-PC3 cells were grown in RPMI medium 1640 containing 2 mM L-glutamine; 10 U/ml Pen-G; 10 mcg/ml Streptomycin and 10% FCS. Cells were kept at 6% $CO_2$ and 37° C.
Cell density: A549 and Bx-PC3 cells were seeded at 1,500 cell/well; PC-3 cells were seeded at 4,000 cell/well and MDA-MB-468 cells were seeded at 2,500 cells/well. Cells were seeded in 96-well format tissue culture plates the day before starting treatment, in the media indicated above.
Treatment: Before commencing drug treatment, cells were replenished with media containing 0.5% FCS. The compounds of the invention having numbers 1, 2, 3, and 7–10 were tested at various concentrations (see FIG. 13), with DMSO as a vehicle control, which never exceeded 0.1% final concentration. Treatment was repeated every other day, for a total of 6 days. As an end point, the amount of surviving cells (Live cells) was measured using a standard calorimetric assay (MTT based), and calculated as percentage of cells treated with vehicle (DMSO) alone (% control).
MTT assay: The assay is based on the cleavage of the yellow tetrazolium salt MTT to purple formazan crystals by dehydrogenase activity in active mitochondria. Therefore, this conversion only occurs in living cells with intact/functional mitochondria. The formazan crystals formed are solubilized and the resulting colored solution is quantified using a scanning multiwell spectrophotometer.
Procedure: 10 μl of 5 mg/ml MTT dye are added to each well. Cells are incubated for additional 4 hours at 6% $CO_2$ and 37° C. Reaction is then stopped by adding 100 μl/well of the solubilization solution, consisting of 10% Sodium Dodecyl Sulfate (SDS) and 10 mM HCl.
Compounds were initially tested at three concentrations 0.1, 1 and 10 uM (sometimes even only one concentration was used 0.5 uM), and for defining the potency of the compound(s) under study, a second test is then run, where several concentrations (titration) were used. Typically, a compound is considered to have potent anticancer activity when is able to inhibit cell growth by 50% or more at a concentration of 10 uM or lower. Importantly, the same compound tested in different cancer cell lines, could display different potency and/or selectivity, such as Compound 7 which at 10 µM kills ~80% of MDA-MB-468 breast cancer cells, while it only kills about 50% or less of the other cancer cell lines studied (see FIG. 12). Another example was Compound 9, which had a very potent anticancer effect on PC-3 prostate cancer cells but its effect was less pronounced on the other cell lines.

Example 16

In Vitro Assay for AKT1/PKBa Kinase Activity Inhibition

The assay was performed using a similar approach as described by Standaert, Mary L., et al. J. Biol. Chem. 1999, 274, 25308–25316; and Aman, M. J. et al, J. Biol. Chem. 1998, 273, 33922–33928. The assay was performed using purified recombinant His-tagged AKT1/PKBα enzyme purchased from Upstate catalog # 14-276 following the manufacturer instruction. The assay is to measure phosphotransferase activity in purified His-tagged AKT1/PKBα. The purified enzyme is used to transfer the γ phosphate of [γ-32P]-ATP to a specific substrate, AKT/GSK peptide [RPRAATA] (upstate Catalog # 12-340). The phosphorylated substrate is then separated from the residual [γ-32P] ATP by using P81 phosphocellulose paper accompanied with extensive washing followed by quantitation using scintillation counter. The assay is linear for incubation times for up to 30 minutes and incorporation of up to 20% of total ATP. This enzyme assay is rapid, convenient and specific for AKT/PKB.

For testing the effect of Compound 2 on the AKT kinase activity, 0.3 µg AKT was pre-incubated with 1 µl of different Compound 2 stock concentration to give the final indicated concentration in total volume of 20 µl reaction buffer. As control 0.3 µg AKT was incubated with 1 µl Vehicle or alone in total volume of 20 µl reaction buffer. After a 10 minute incubation at 30° C., the kinase reaction was carried out according to the instruction of the manufacturer.

Figure 5:
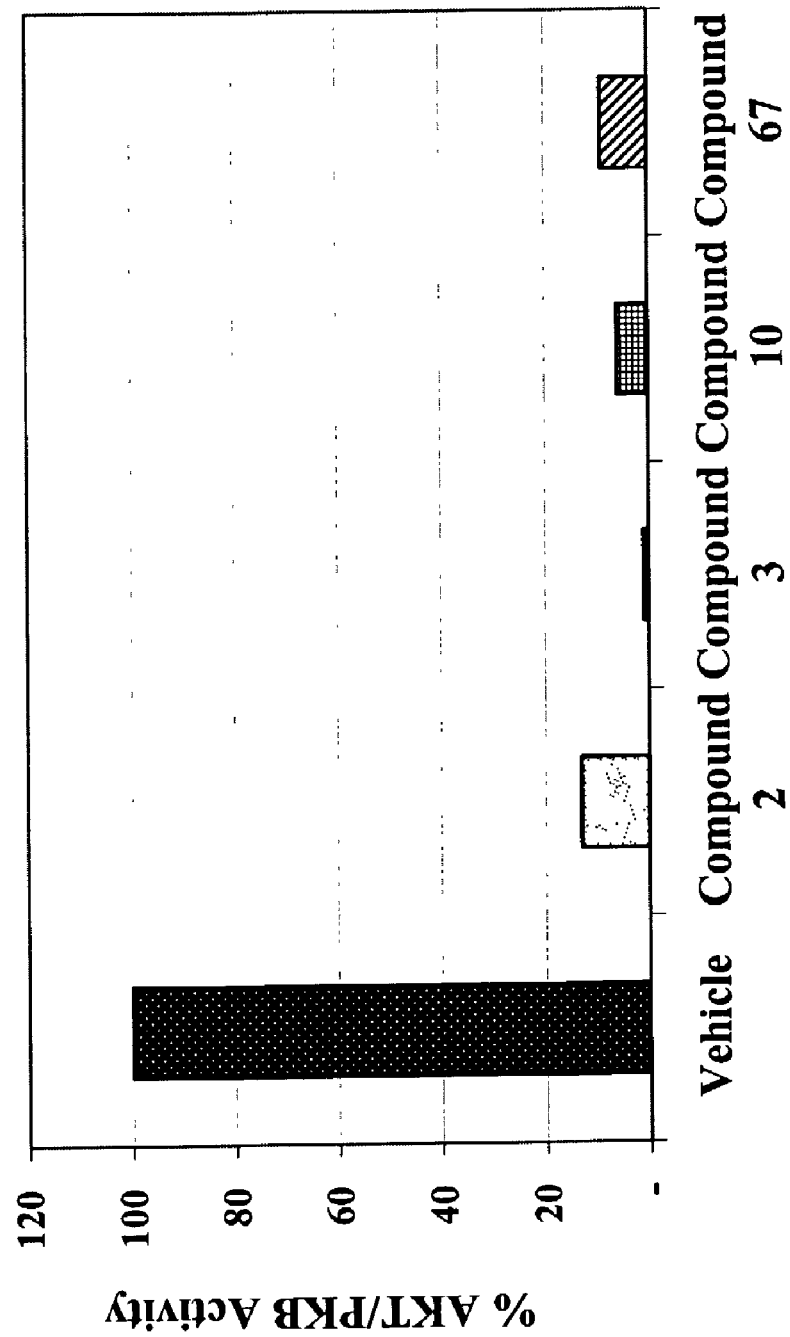
FIG. 5 shows the inhibition of AKT/PKB Kinase activity after treatment with Compounds of the invention.

As shown in FIG. 5, pre-incubation of AKT with Vehicle did not affect kinase activity, as its phosphotransferase activity is equal when the enzyme was assayed alone. Pre-incubation of AKT with test compounds, Compounds 2, 3, 10 and 67, at 5 µM showed inhibition of AKT activity (FIG. 5) compared to Control or Vehicle.

Example 17

Lactam Compounds of the Invention, such as 3-methyl-5-[3-(1,4,4,6-tetramethyl-2-oxo-1,2,3,4-tetrahydro-quinolin-7-yl)-4-trifluoromethoxy-benzylidene]-thiazolidine-2,4-dione, Illustrated below wherein $R_2$ is a Methyl Group, an be Prepared as Illustrated below.

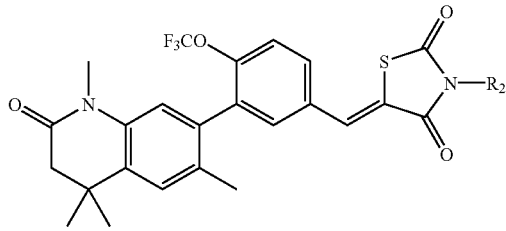

A mixture of toluene (80 mL), piperidine (380 µL), acetic acid (380 µL), 3-(1,4,4,6-Tetramethyl-2-oxo-1,2,3,4-tetrahydro-quinolin-7-yl)-4-trifluoromethoxy-benzaldehyde (7.5 g, 19.16 mmol) and a 3-alkyl—thiazolidine-2,4-dione such as 3-Methyl-thiazolidine-2,4-dione (19.16 mmol) is heated at reflux overnight. The reaction mixture is cooled to room temperature, diluted with ethyl acetate and is washed with water and brine, dried over $MgSO_4$. The residue is recrystallized to afford 3-methyl-5-[3-(1,4,4,6-tetramethyl-2-oxo-1,2,3,4-tetrahydro-quinolin-7-yl)-4-trifluoromethoxy-benzylidene]-thiazolidine-2,4-dione.

The intermediate 3-(1,4,4,6-tetramethyl-2-oxo-1,2,3,4-tetrahydro-quinolin-7-yl)-4-trifluoromethoxy-benzaldehyde was prepared as follows:

a. 3-(1,4,4,6-Tetramethyl-2-oxo-1,2,3,4-tetrahydro-quinolin-7-yl)-4-trifluoromethoxy-benzaldehyde.

A mixture of 3-formyl-6-trifluoromethoxy-1-phenyl boronic acid (3.14 g, 13.42 mmol), 7-bromo-1,4,4,6-tetramethyl-3,4-dihydro-1H-quinoline-2-one (3.15 g, 11.19 mmol) and potassium carbonate (3.1 g, 22.38 mmol) in toluene (35 mL), ethanol (11.8 mL) and water (7.3 mL) was degassed with argon for 15 minutes.

Tetrakis(triphenylphosphine)palladium(0) (0.259 g, 0.02 mmol) was added and the mixture heated at reflux under argon overnight. The solution was cooled to room temperature, diluted with ethyl acetate and washed successively with water and brine, dried over anhydrous magnesium sulfate, filtered and evaporated. The residue was purified on silica gel (20 to 30% ethyl acetate in hexane) to give 2.34 g of 3-(1,4,4,6-tetramethyl-2-oxo-1,2,3,4-tetrahydro-quinolin-7-yl)-4-trifluoromethoxy-benzaldehyde (54%). $^1$H NMR (300 MHz; $CDCl_3$): 1.35 (s, 6 H), 2.11 (s, 3 H), 2.55 (s, 2 H), 3.35 (s, 3 H), 6.79 (s, 1 H), 7.20 (s, 1 H), 7.54 (dd, J=3 and 8.4 Hz, 1 H), 7.85 (d, J=2.7 Hz, 1 H), 7.90 (dd, J=2.1 and 8.7 Hz, 1 H), 10.04 (s, 1 H).

b. 3-formyl-6-trifluoromethoxy-1-phenyl boronic acid.

To a mixture of 2-(3-bromo-4-trifluoromethoxy-1-phenyl)-1,3-dioxolane (7.20 g, 22.9 mmol) in THF (70 mL) cooled to −78° C. under an atmosphere of argon was added n-BuLi (13.8 mL, 2.5 M, 34.4 mmol) dropwise. The resulting suspension was stirred for 5 minutes and triisopropylborate (15.9 mL, 68.7 mmol) was added dropwise via syringe. The mixture was stirred at −50° C. for 2 hours then warmed up to room temperature and stirred overnight at room temperature. 1.0 N HCl (50 mL) was slowly added to the reaction mixture. After 3 hours the mixture was diluted with ethyl acetate and the layers separated, the aqueous layer was extracted once with ethyl acetate and the two organic layers combined. The resulting organic layer was washed with water, brine and dried ($Mg_2SO_4$). The mixture was filtered, evaporated and the residue stirred in hexane. The resulting white suspension was filtered and the white solid dried under high vacuum to afford 3.00 g of 3-formyl-6-trifluoromethoxy-1-phenyl boronic acid (56%). $^1$H NMR (300 MHz; $CDCL_3$): δ 7.42 (d, J=7.0 Hz, 1 H), 8.07 (dd, $J_1$=2.1 Hz, $J_2$=8.7 Hz, 1 H), 8.47 (d, J=1.8 Hz, 1 H), 10.05 (s, 1 H).

c. 2-(3-bromo-4-trifluoromethoxy-1-phenyl)-1,3-dioxolane.

To a solution of 3-bromo-4-trifluoromethoxybenzaldehyde (20 g, 74.0 mmol) in toluene (200 mL) was added ethylene glycol (82.6 mL, 1.48 mol) and p-toluenesulfonic acid monohydrate (0.84 g, 4.44 mmol). The reaction mixture was heated at reflux overnight and the water was removed using a Dean Stark apparatus. The solution was cooled to room temperature, poured into aqueous potassium carbonate (10%) and extracted with ethyl acetate. The organic layer was washed with water, brine and dried ($Mg_2SO_4$). The residue was purified on silica gel (eluent: 10% ethyl acetate in hexane) to give 15.4 g of 2-(3-bromo-4-trifluoromethoxy)-1,3-dioxolane (66%). ¹H NMR (500 MHz; CDCl₃): δ 4.05 (m, 2 H), 4.11 (m, 2 H), 5.79 (s, 1 H), 7.32 (d, 1 H), 7.43 (d, 1 H), 7.77 (d, J=1.1 Hz, 1 H).

d. 7-bromo-1,4,4,6-tetramethyl-3,4-dihydro-1H-quinoline-2-one.

A mixture of powdered KOH (14.06 g, 0.250 mol) in DMSO (150 mL) was stirred at 0° C. for 10 min. 7-Bromo-4,4,6-trimethyl-3,4-dihydro-1H-quinoline-2-one (33.59 g, 0.125 mol) was added cautiously, followed immediately by the addition of methyl iodide (39 mL, 0.625 mol). The reaction mixture was kept at 0° C. for 30 min then slowly warmed up to room temperature and stirred overnight at room temperature. The reaction mixture was poured into water and extracted with dichloromethane washed with water and brine, dried (Mg₂SO₄), filtered and evaporated to give 35.74 g of 7-bromo-1,4,4,6-tetramethyl-3,4-dihydro-1H-quinoline-2-one (99%) and used without further purification in the Suzuki coupling (step a). ¹H NMR (300 MHz; CDCl₃): 1.27 (s, 6 H), 2.37 (s, 3 H), 2.48 (s, 2 H), 3.35 (s, 3 H), 7.12 (s, 1 H), 7.16 (s, 1 H).

e. 7-bromo-4,4,6-trimethyl-3,4-dihydro-1H-quinoline-2-one.

To a solution of 3-methyl-but-2-enoic acid (3-bromo-4-methyl-phenyl)-amide (70.0 g, 261 mmol) at 90° C. was added portion wise, under argon, with vigorous stirring aluminum chloride (52.3 g, 391 mmol) over 1.5 hr. The reaction mixture was stirred for 2 hours at 110–120° C. The reaction mixture was cooled to room temperature and ice-water was carefully added. The solution was extracted with dichloromethane and the organic washed with 2N HCl, water, saturated aqueous NaHCO₃, water and brine, dried (Mg₂SO₄), filtered and evaporated. The residue was crystallized from dichloromethane/hexane to give 46 g of 7-bromo-4,4,6-trimethyl-3,4-dihydro-1H-quinoline-2-one. The mother liquor was further chromatographed on silica gel (20% ethyl acetate in hexane) to give 6.2 g more of product. (75%). ¹H NMR (300 MHz; CDCl₃): 1.30 (s, 6 H), 2.33 (s, 3 H), 2.46 (s, 2 H), 7.07 (s, 1 H), 7.10 (s, 1 H), 9.87 (br s, 1 H).

f. 3-Methyl-but-2-enoic acid (3-bromo-4-methyl-phenyl)-amide.

To a biphasic mixture of 3-bromo-4-methylaniline (50 g, 0.269 mol), 10% NaOH (270 mL) and dichloromethane (160 mL) was added dropwise over a period of 2 hours 3,3-dimethylacryloyl chloride (36 mL, 0.322 mol) in dichloromethane (95 mL). The solution was stirred at room temperature for 48 hours then diluted with water (100 mL). The aqueous layer was further extracted with dichloromethane. The organic layers were combined and washed with water and brine, dried (Mg₂SO₄), filtered and evaporated. The white solid was triturated with hexane and collected to give 70 g (97%) of 3-Methyl-but-2-enoic acid (3-bromo-4-methyl-phenyl)-amide. ¹H NMR (300 MHz; CDCl₃): 1.89 (s, 3 H), 2.21 (s, 3 H), 2.33 (s, 3 H), 5.68 (s, 1 H), 7.14 (d, J=8.0 Hz, 1 H), 7.17 (br s, 1 H), 7.33 (d, J=8.0 Hz, 1 H), 7.79 (s, 1 H).

g. 3-bromo-4-methylaniline.

To a solution of 2-bromo-4-nitrotoluene (50 g, 0.231 mol in ethylacetate (330 mL) and Ethanol (150 mL) was added Tin(II)chloride dihydrate (208 g, 0.924 mol) portionwise. The reaction mixture was stirred at room temperature overnight. The solution was then treated with potassium carbonate until pH=7 and filtered over celite. The filtrate was washed with water, aqueous NaHCO₃, water and brine, dried (Mg₂SO₄), filtered and evaporated to give 42.71 g (100%) of 3-bromo-4-methylaniline. ¹H NMR (300 MHz; CDCl₃): 2.27 (s, 3 H), 3.57 (br s, 2 H), 6.54 (dd, J=2.7 Hz and 8.1 Hz, 1 H), 6.90 (d, J=2.1 Hz, 1 H), 6.98 (d, J=8.1 Hz, 1 H).

Example 18

5-[3-(1-Ethyl-4,4,6-trimethyl-2-oxo-1,2,3,4-tetrahydro-quinolin-7-yl)-4-trifluoromethoxy-benzylidene]-3-methyl-thiazolidine-2,4-dione, as shown below where R2 is methyl, can be prepared in a similar manner to example 1 using 3-(1-ethyl-4,4,6-trimethyl-2-oxo-1,2,3,4-tetrahydro-quinolin-7-yl)-4-trifluoromethoxy-benzaldehyde as an aldehyde intermediate comprising the specified lactam functionality.

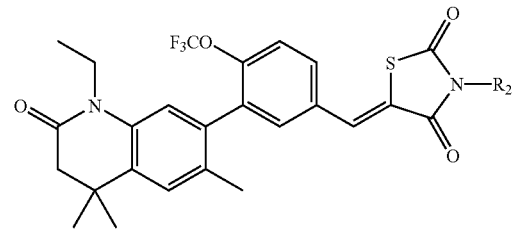

The intermediate 3-(1-Ethyl-4,4,6-trimethyl-2-oxo-1,2,3,4-tetrahydro-quinolin-7-yl)-4-trifluoromethoxy-benzaldehyde was prepared as follows:

a. 3-(1-Ethyl-4,4,6-trimethyl-2-oxo-1,2,3,4-tetrahydro-quinolin-7-yl)-4-trifluoromethoxy-benzaldehyde.

A mixture of 3-formyl-6-trifluoromethoxy-1-phenyl boronic acid (Example 1b) (8.2 g, 34.84 mmol), 7-bromo-1-ethyl-4,4,6-trimethyl-3,4-dihydro-1H-quinoline-2-one (8.6 g, 29.03 mmol) and potassium carbonate (8 g, 58.06 mmol) in toluene (80 mL), ethanol (16 mL) and water (12 mL) was degassed with argon for 30 minutes. Tetrakis(triphenylphosphine)palladium(0) (1.34 g, 0.04 mmol) was added and the mixture heated at reflux under argon for 48 hrs. The solution was cooled to room temperature, diluted with ethyl acetate and washed successively with water and brine, dried over anhydrous magnesium sulfate, filtered and evaporated. The residue was purified on silica gel (30% ethyl acetate in hexane) to give 6.66 g of 3-(1-ethyl-4,4,6-trimethyl-2-oxo-1,2,3,4-tetrahydro-quinolin-7-yl)-4-trifluoromethoxy-benzaldehyde (57%). ¹H NMR (300 MHz; CDCl₃): 1.20 (t, J=7.2 Hz, 3 H), 1.33 (s, 6 H), 1.62 (s, 3 H), 2.10 (s, 3 H), 2.53 (s, 2 H), 4.00 (br d, 2 H), 6.81 (s, 1 H), 7.19 (s, 1 H), 7.55 (dd, J=1.8 and 8.4 Hz, 1 H), 7.85 (d, J=2.4 Hz, 1 H), 7.97 (dd, J=2.1 and 8.4 Hz, 1 H), 10.05 (s, 1 H).

b. 7-bromo-1-ethyl-4,4,6-trimethyl-3,4-dihydro-1H-quinoline-2-one.

A mixture of powdered potassium hydroxide (3.35 g, 59.67 mmol) in DMSO (40 mL) was stirred at 0° C. for 10 min. 7-bromo-4,4,6-trimethyl-3,4-dihydro-1H-quinoline-2-one (Example 1e) (8.0 g, 29.83 mmol) was added cautiously, followed immediately by the addition of ethyl iodide (12 mL, 149.17 mmol). The reaction mixture was kept at 0° C. for 30 min then slowly warmed up to room temperature and stirred overnight at room temperature. The reaction mixture was poured into water and extracted with dichloromethane washed with water and brine, dried (Mg₂SO₄), filtered and evaporated to give 8.8 g of 7-bromo-1,4,4,6-tetramethyl-3,4-dihydro-1H-quinoline-2-one and used without further purification in the Suzuki coupling (step a). $^1$H NMR (300 MHz; CDCl$_3$): 1.24 (t, J=7.2 Hz, 1 H), 1.25 (s, 6 H), 2.37 (s, 3 H), 2.45 (s, 2 H), 3.98 (q, 2 H), 7.13 (s, 1 H), 7.18 (s, 1 H).

Example 19

6-[2-Dimethylamino-5-(3-alkyl-2,4-dioxo-thiazolidin-5-ylidenemethyl)-phenyl]-1,4,7-trimethyl-1,4-dihydro-quinoxaline-2,3-diones, as Shown below, such as 6-[2-Dimethylamino-5-(3-methyl-2,4-dioxo-thiazolidin-5-ylidenemethyl)-phenyl]-1,4,7-trimethyl-1,4-dihydro-quinoxaline-2,3-dione, wherein R$_2$ is Methyl, can be Prepared in a Similar Manner to Example 1 using 4-Dimethylamino-3-(1,4,7-trimethyl-2,3-dioxo-1,2,3,4-tetrahydro-quinoxalin-6-yl)-benzaldehyde as an Intermediate.

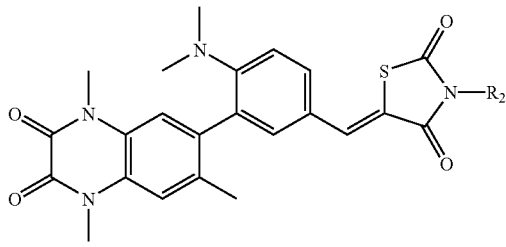

The intermediate 4-Dimethylamino-3-(1,4,7-trimethyl-2,3-dioxo-1,2,3,4-tetrahydro-quinoxalin-6-yl)-benzaldehyde was prepared in a similar manner to example 3a using 6-dimethylamino-3-formyl-1-phenyl boronic acid (example 3b) and 6-bromo-1,4,7-trimethyl-1,4-dihydro-quinoxaline-2,3-dione (18%). $^1$H NMR (300 MHz; CDCl$_3$): 2.12 (s, 3 H), 2.69 (s, 6 H), 3.65 (s, 6 H), 7.1–7.6 (m, 5 H), 9.84 (s, 1 H).

a. 6-bromo-1,4,7-trimethyl-1,4-dihydro-quinoxaline-2,3-dione.

To a solution of 1,4,6-trimethyl-1,4-dihydro-quinoxaline-2,3-dione (0.66 g, 3.2 mmol) in acetic acid (40 mL) was added bromine (0.52 g, 3.2 mmol) and the solution stirred at 50° C. overnight. The reaction mixture was cooled to room temperature and poured into water. The solution was neutralized with aqueous NaOH to Ph=7, extracted with dichloromethane and washed with brine, dried (Mg$_2$SO$_4$), filtered and evaporated to give 0.9 g of 6-bromo-1,4,7-trimethyl-1,4-dihydro-quinoxaline-2,3-dione used without further purification in the Suzuki coupling (step a). $^1$H NMR (300 MHz; CDCl$_3$): 2.47 (s, 3 H), 3.64 (s, 6 H), 7.09 (s, 1 H), 7.40 (s, 1 H).

b. 1,4,6-trimethyl-1,4-dihydro-quinoxaline-2,3-dione.

To a solution of 6-methyl-1,4-dihydro-quinoxaline-2,3-dione (5.3 g, 30 mmol) in THF (150 mL) was added, at 0° C. under argon, sodium hydride (3.68 g, 80% in mineral oil, 120 mmol) followed by methyl iodide (7.5 mL, 120 mmol). The solution was stirred at 0° C. for 3 hrs and at room temperature overnight. The reaction mixture was cooled to 0° C. and acidified with 1N HCl. The solution was extracted with dichloromethane washed with brine, dried (Mg$_2$SO$_4$), filtered and evaporated. The residue was chromatographed on silica gel (10 to 25% acetonitrile in dichloromethane) to give 1.1 g of 1,4,6-trimethyl-1,4-dihydro-quinoxaline-2,3-dione (18%). $^1$H NMR (300 MHz; CDCl$_3$): 2.44 (s, 3 H), 3.66 (s, 6 H), 7.06–7.15 (m, 3 H).

c. 6-methyl-1,4-dihydro-quinoxaline-2,3-dione.

3,4-Diaminotoluene (24.4 g, 0.2 mmol) was dissolved in 2N HCl (300 mL), oxalic acide dihydrate (27.7 g, 0.22 mmol) was added and the mixture was heated at reflux for 3.5 hrs. The reaction mixture was cooled to room temperature, filtered, washed with water, dried (Mg$_2$SO$_4$), filtered and evaporated to give 34 g of 6-methyl-1,4-dihydro-quinoxaline-2,3-dione (96%). $^1$H NMR (300 MHz; CDCl$_3$): 2.25 (s, 3 H), 6.87–6.99 (m, 3 H), 11.87 (br s, 2 H).

Example 20

5-[3-(1-Benzyl-3,3,5-trimethyl-2-oxo-2,3-dihydro-1H-indol-6-yl)-4-trifluoromethoxy-benzylidene]-3-alkyl-thiazolidine-2,4-diones, as shown below, such as 5-[3-(1-benzyl-3,3,5-trimethyl-2-oxo-2,3-dihydro-1H-indol-6-yl)-4-trifluoromethoxy-benzylidene]-3-methyl-thiazolidine-2,4-dione, wherein R$_2$ is Methyl, can be prepared in a similar manner to example 1 using 3-(1-Benzyl-3,3,5-trimethyl-2-oxo-2,3-dihydro-1H-indol-6-yl)-4-trifluoromethoxy-benzaldehyde as an intermediate.

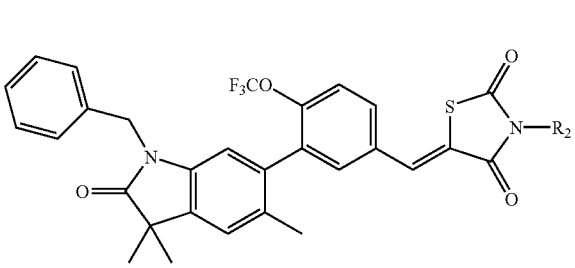

a. 3-(1-Benzyl-3,3,5-trimethyl-2-oxo-2,3-dihydro-1H-indol-6-yl)-4-trifluoromethoxy-benzaldehyde.

The intermediate 3-(1-Benzyl-3,3,5-trimethyl-2-oxo-2,3-dihydro-1H-indol-6-yl)-4-trifluoromethoxy-benzaldehyde was prepared in a similar manner to example 1 a using 3-formyl-6-trifluoromethoxy-1-phenyl boronic acid (Example 1b) and trifluoro-methanesulfonic acid 1-benzyl-3,3,5-trimethyl-2-oxo-2,3-dihydro-1H-indol-6-yl ester. 27% yield. $^1$H NMR (300 MHz; CDCl$_3$): 1.48 (s, 6 H), 2.07 (s, 3 H), 4.89 (s, 2 H), 6.50 (s, 1 H), 1.74 (t, J=6.0 Hz, 2 H), 2.01 (s, 3 H), 2.69 (s, 6 H), 2.91 (dd, J=7.2 and 14.7 Hz, 1 H), 7.13 (s, 1 H), 7.27 (m, 5 H), 7.47 (d, J=8.4 Hz, 1 H), 7.71 (s, 1 H), 7.93 (d, J=8.4 Hz, 1 H)), 9.99 (s, 1 H).

b. Trifluoro-methanesulfonic acid 1-benzyl-3,3,5-trimethyl-2-oxo-2,3-dihydro-1H-indol-6-yl ester.

To a solution of 1-benzyl-6-hydroxy-3,3,5-trimethyl-1,3-dihydro-indol-2-one (1.85 g, 6.60 mmol) in anhydrous dichloromethane (30 mL) was added slowly, under argon at 0° C., pyridine (0.64 mL, 7.92 mmol) followed by triflic anhydride (1.33 mL, 7.92 mmol). The reaction was warmed up to room temperature and stirred overnight. The mixyure was washed successively with water, 1N HCl, water, saturated aqueous NaHCO$_3$, water and brine. The organic extract was dried over MgSO$_4$, filtered and evaporated to give 2.6 g of trifluoro-methanesulfonic acid 1-benzyl-3,3,5-trimethyl-2-oxo-2,3-dihydro-1H-indol-6-yl ester (95% yield). $^1$H NMR (300 MHz; CDCl$_3$): 1.42 (s, 6 H), 2.31 (s, 3 H), 4.87 (s, 2 H), 6.55 (s, 1 H), 7.09 (s, 1 H), 7.29 (m, 5 H).

c. 1-benzyl-6-hydroxy-3,3,5-trimethyl-1,3-dihydro-indol-2-one.

To a solution of 1-benzyl-6-methoxy-3,3,5-trimethyl-1,3-dihydro-indol-2-one (1.52 g, 5.15 mmol) in anhydrous dichloromethane (50 mL) was added slowly, under argon at −78° C., BBr$_3$ (0.87 mL, 9.27 mmol). The reaction was warmed up to −20° C. and stirred overnight at room temperature. Water and the layer separated. The aqueous layer was neutralized with NaHCO$_3$ and extracted with dichloromethane. The organic combined extract was washed with aqueous NaHCO$_3$, water and brine, dried over MgSO$_4$, filtered and evaporated to give 1-benzyl-6-hydroxy-3,3,5-trimethyl-1,3-dihydro-indol-2-one (93% yield). $^1$H NMR (300 MHz; CDCl$_3$): 1.38 (s, 6 H), 2.19 (s, 3 H), 4.82 (s, 2 H), 5.47 (br s, 1 H), 6.26 (s, 1 H), 6.93 (s, 1 H), 7.26 (m, 5 H).

d. 1-benzyl-6-methoxy-3,3,5-trimethyl-1,3-dihydro-indol-2-one.

To a solution of N-benzyl-N-(2-bromo-5-methoxy-4-methyl-phenyl)-isobutyramide (4.35 g, 11.56 mmol) in 1,4-dioxane (115 mL) was added sodium tert-butoxide (1.66 g, 17.34 mmol). The mixture was degassed under argon for 30 minutes, then palladium (II) acetate (130 mg, 0.58 mmol) and tricyclohexylphosphine (162 mg, 0.58 mmol) were added and the mixture refluxed overnight. A solution of saturated aqueous ammonium chloride was added and the solution extracted with ethyl acetate. The organic extract was washed successively with water and brine, dried over MgSO$_4$, filtered and evaporated. The residue was chromatographed on silica gel (20% ethyl acetate in hexane) to give 1.94 g of 1-benzyl-6-methoxy-3,3,5-trimethyl-1,3-dihydro-indol-2-one (57% yield). $^1$H NMR (300 MHz; CDCl$_3$): 1.40 (s, 6 H), 2.16 (s, 3 H), 3.67 (s, 3 H), 4.90 (s, 2 H), 6.26 (s, 1 H), 6.96 (s, 1 H), 7.27 (m, 5 H).

e. N-benzyl-N-(2-bromo-5-methoxy-4-methyl-phenyl)-isobutyramide.

A mixture of powdered KOH (1.3 g, 23.13 mmol) in DMSO (25 mL) was stirred at 0° C. for 5 minutes. N-(2-bromo-5-methoxy-4-methyl-phenyl)-isobutyramide (3.30 g, 11.56 mmol) was added cautiously followed immediately by the addition of benzylbromide (2.75 mL, 23.13 mmol) and the reaction stirred at room temperature for 48 hrs. Water was added and the mixture extracted with ethyl acetate. The organic extract was washed successively with water and brine, dried over MgSO$_4$, filtered and evaporated. The residue was chromatographed on silica gel (20% ethyl acetate in hexane) to give 4.3 g of N-benzyl-N-(2-bromo-5-methoxy-4-methyl-phenyl)-isobutyramide (99% yield). $^1$H NMR (300 MHz; CDCl$_3$): 1.02 (d, J=6.6 Hz, 3 H), 1.15 (d, J=6.6 Hz, 3 H), 2.16 (s, 3 H), 2.29 (m, 1 H), 3.43 (s, 3 H), 3.85 (d, J=14.1 Hz, 1 H), 5.75 (d, J=14.1 Hz, 1 H), 6.02 (s, 1 H), 7.18–7.27 (m, 5 H), 7.38 (s, 1 H).

f. N-(2-bromo-5-methoxy-4-methyl-phenyl)-isobutyramide.

To a biphasic mixture of 2-bromo-5-methoxy-4-methyl-aniline (5.6 g, 25.96 mmol), 10% KOH (27 mL) and dichloromethane (30 mL), was added dropwise isobutyryl chloride (3 mL, 28.55 mmol) in dichloromethane (10 mL). The reaction mixture was stirred at room temperature for 48 hrs. The layers were separated. The aqueous layer was further extracted with dichloromethane and the combined organics washed successively with water and brine, dried over MgSO$_4$, filtered and evaporated to give 7.38 g of N-(2-bromo-5-methoxy-4-methyl-phenyl)-isobutyramide (99% yield). $^1$H NMR (300 MHz; CDCl$_3$): 1.29 (d, J=6.9 Hz, 6 H), 2.14 (s, 3 H), 2.59 (m, 1 H), 3.84 (s, 3 H), 7.24 (s, 1 H), 7.66 (br s, 1 H), 8.07 (s, 1 H).

g. 2-bromo-5-methoxy-4-methyl-aniline.

To a solution of 3-methoxy-4-methyl-aniline (8.19 g, 59.71 mmol) in dichloromethane (200 mL), was added tetrabutylammonium tribromide (28.79 g, 59.71 mmol) and the reaction mixture was stirred at room temperature for 2.5 hrs. Aqueous NaHCO$_3$ was added and the layers separated. The aqueous layer was further extracted with dichloromethane and the combined organics washed successively with water and brine, dried over MgSO$_4$, filtered and evaporated. The residue was chromatographed on silica gel (20% ethyl acetate in hexane) to give 11.05 g of 2-bromo-5-methoxy-4-methyl-aniline (85% yield). $^1$H NMR (300 MHz; CDCl$_3$): 2.09 (s, 3 H), 3.75 (s, 3 H), 3.95 (br s, 1 H), 6.27 (s, 1 H), 7.13 (s, 1 H).

h. 3-methoxy-4-methyl-aniline.

To a solution of 2-methyl-5-nitroanisole (11.56 g, 69.2 mmol) in a mixture of ethyl acetate (200 mL) and ethanol (70 mL) was added portionwise tin (II) chloride dihydrate (109 g, 0.483 mol) and the mixture was stirred at room temperature overnight. The reaction mixture was basified with aq. K$_2$CO$_3$ and filtered over celite. The layers were separated. The aqueous layer was further extracted with ethyl acetate and the combined organics washed successively with water and brine, dried over MgSO$_4$, filtered and evaporated to give 8.02 g of 3-methoxy-4-methyl-aniline (86% yield). $^1$H NMR (300 MHz; CDCl$_3$): 2.09 (s, 3 H), 3.76 (s, 3 H), 4.01 (br s, 1 H), 6.20 (m, 2 H), 6.90 (d, J=8.4 Hz, 1 H).

Example 21

5-[3-(5-Isobutyl-3,3-dimethyl-2,3-dihydro-benzofuran-7-yl)-4-trifluoromethoxy-benzylidene]-3-substituted-thiazolidine-2,4-diones

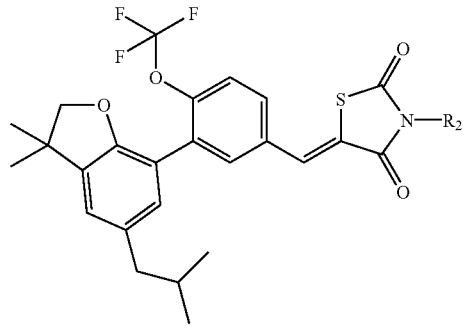

Compounds of the formula shown above, having R$_2$ substituents at the nitrogen atom of the thiazolidine-2,4-dione radical can be prepared as follows.

A mixture of toluene (35 mL), piperidine (145 μL), acetic acid (145 μL), 3-(5-isobutyl-3,3-dimethyl-2,3-dihydro-benzofuran-7-yl)-4-trifluoromethoxy-benzaldehyde (5.7 g, 14.53 mmol) and a 3-substituted 2,4-thiazolidinedione (14.53 mmol) is heated at reflux for 20 hrs. The reaction mixture is cooled to room temperature, diluted with ethyl acetate, washed with water and brine, dried over MgSO$_4$, filtered and evaporated. The residue can be chromatographed on silica gel (0 to 20% ethylacetate in hexane) and/or further recrystallised. The intermediate 3-(5-isobutyl-3,3-dimethyl-2,3-dihydro-benzofuran-7-yl)-4-trifluoromethoxy-benzaldehyde was prepared as follows:

a. 3-(5-isobutyl-3,3-dimethyl-2,3-dihydro-benzofuran-7-yl)-4-trifluoromethoxy-benzaldehyde.

A mixture of 3-bromo-4-trifluoromethoxy benzaldehyde (4.24 g, 15.75 mmol), 5-isobutyl-3,3-dimethyl-2,3-dihydro-benzofuran-7-boronic acid (4.3 g, 17.33 mmol) and potassium carbonate (4.35 g, 31.5 mmol) in toluene (39 mL), ethanol (7.5 mL) and water (2.5 mL) was degassed with argon for 15 minutes.

Tetrakis(triphenylphosphine)palladium(0) (0.728 g, 0.63 mmol) was added and the mixture heated at reflux under argon for 20 hrs. The solution was cooled to room temperature, diluted with ethyl acetate and washed successively with water and brine, dried over anhydrous magnesium sulfate, filtered and evaporated. The residue was purified on silica gel (0 to 5% ethyl acetate in hexane) to give 5.76 g of 3-(5-isobutyl-3,3-dimethyl-2,3-dihydro-benzofuran-7-yl)-4-trifluoromethoxy-benzaldehyde (93%). $^1$H NMR (300 MHz; CDCl$_3$): 0.92 (d, J=6.9 Hz, 6 H), 1.36 (s, 6 H), 1.84 (m, 1 H), 2.47 (d, J=7.5 Hz, 2 H), 4.22 (s, 2 H), 6.92 (d, J=4.8 Hz, 2 H), 7.46 (dd, J=1.5 Hz and 8.7 Hz, 1 H), 7.90 (dd, J=2.1 Hz and 8.7 Hz, 1 H), 8.03 (d, J=2.1 Hz, 1 H), 10.03 (s, 1 H).

b. 5-isobutyl-3,3-dimethyl-2,3-dihydro-benzofuran-7-boronic acid.

To a mixture of 7-bromo-5-isobutyl-3,3-dimethyl-2,3-dihydro-benzofuran (9.9 g, 34.96 mmol) in THF (50 mL) cooled to −78° C. under an atmosphere of argon was added n-BuLi (25.17 mL, 2.5 M, 62.93 mmol) dropwise. The reaction mixture was stirred for 5 minutes and triisopropylborate (24.2 mL, 104.87 mmol) was added dropwise. The mixture was stirred at −50° C. for 2 hours then warmed up to room temperature and stirred overnight at room temperature. 1.0 N HCl (100 mL) was slowly added to the reaction mixture. After 1 hour the mixture was diluted with ethyl acetate and the layers separated. The organic layer was further washed with water, brine, dried (Mg$_2$SO$_4$), filtered and evaporated. The residue was chromatographed on silica gel (0 to 20% ethyl acetate in hexane) to give 4.3 g of 5-isobutyl-3,3-dimethyl-2,3-dihydro-benzofuran-7-boronic acid (46%). $^1$H NMR (300 MHz; CDCL$_3$): 0.90 (d, J=6.6 Hz, 6 H), 1.33 (s, 6 H), 1.81 (m, 1 H), 2.43 (d, J=7.5 Hz, 2 H), 4.28 (s, 2 H), 5.86 (br s, 2 H), 6.98 (d, J=2.1 Hz, 1 H), 7.33 (d, J=2.1 Hz, 1 H).

c. 7-bromo-5-isobutyl-3,3-dimethyl-2,3-dihydro-benzofuran.

To a solution of 5-isobutyl-3,3-dimethyl-2,3-dihydro-benzofuran (1.59 g, 7.78 mmol) in dichloromethane (40 mL) was added pyridinium tribromide (2.49 g, 7.78 mmol) and the reaction mixture stirred at room temperature overnight. The solution was washed with water and brine, dried (Mg$_2$SO$_4$), filtered and evaporated. The residue was purified on silica gel (0% to 2% ethyl acetate in hexane) to give 1.51 g of 7-bromo-5-isobutyl-3,3-dimethyl-2,3-dihydro-benzofuran (68%). $^1$H NMR (300 MHz; CDCl$_3$): δ 0.90 (d, J=6.3 Hz, 6 H), 1.33 (s, 6 H), 1.77 (m, 1 H), 2.39 (d, J=7.5 Hz, 2 H), 4.30 (s, 2 H), 6.80 (d, J=1.5 Hz, 1 H), 7.05 (d, J=1.5 Hz, 1 H).

d. 5-isobutyl-3,3-dimethyl-2,3-dihydro-benzofuran.

To a cold solution (0° C.) of 1-(3,3-dimethyl-2,3-dihydro-benzofuran-5-yl)-2-methyl-propan-1-ol (1.97 g, 8.93 mmol) in dry dichloromethane (40 mL) was added triethylsilane (2.85 mL, 17.86 mmol). After 10 minutes, trifluoroacetic acid was the reaction mixture stirred at 0° C. for 30 minutes. Water was poured into the reaction mixture and the layers separated. The organic layer was further washed with water, aqueous NaHCO$_3$ and brine, dried (Mg$_2$SO$_4$), filtered and evaporated. The residue was purified on silica gel (0% to 5% ethyl acetate in hexane) to give 1.6 g of 5-isobutyl-3,3-dimethyl-2,3-dihydro-benzofuran (87%). $^1$H NMR (300 MHz; CDCl$_3$): δ 0.90 (d, J=6.3 Hz, 6 H), 1.32 (s, 6 H), 1.79 (m, 1 H), 2.40 (d, J=6.9 Hz, 2 H), 4.20 (s, 2 H), 6.68 (dd, J=1.2 Hz and 7.5 Hz, 1 H), 6.87 (m, 2 H).

e. 1-(3,3-dimethyl-2,3-dihydro-benzofuran-5-yl)-2-methyl-propan-1-ol.

To a solution of 5-bromo-3,3-dimethyl-2,3-dihydro-benzofuran (2.03 g, 8.93 mmol) in dry THF (10 mL) at −78° C., under argon, was added dropwise n-BuLi (1.6 M in hexane, 13.4 mmol, 8.38 mL). The mixture was stirred for 5 minutes then isobutyraldehyde (1.22 mL, 8.38 mmol) was added and the mixture was slowly warmed up to room temperature and stirred overnight at room temperature. Aqueous ammonium chloride was added and the solution extracted with ethylacetate and the organic extract was dried (Mg$_2$SO$_4$), filtered and evaporated. The residue was purified on silica gel (0% to 20% ethyl acetate in hexane) to give 1.97 g of 1-(3,3-dimethyl-2,3-dihydro-benzofuran-5-yl)-2-methyl-propan-1-ol (100%). $^1$H NMR (300 MHz; CDCl$_3$): δ 0.77 (d, J=6.6 Hz, 3 H), 0.90 (d, J=6.6 Hz, 3 H), 1.33 (s, 6 H), 1.95 (m, 1 H), 4.23 (s, 2 H), 4.28 (d, J=7.2 Hz, 2 H), 6.72 (d, J=8.4 Hz, 1 H), 7.03 (dd, J=8.1 Hz and 1.8 Hz, 1 H), 7.06 (d, J=1.5 Hz, 1 H).

f. 5-bromo-3,3-dimethyl-2,3-dihydro-benzofuran.

A mixture of 4-bromo-2-(2-chloro-1,1-dimethyl-ethyl)-1-methoxy-benzene (65 g, 0.234 mol), pyridine hydrochloride (121.8 g, 1.054 mol) and quinoline (110.67 mL, 0.936 mol) was refluxed at 164° C.–167° C. under argon for 5 hrs. After cooling to room temperature the reaction mixture was treated with ice-cold 6N HCl and extracted twice with ether. The organic layers were combined, dried (Mg$_2$SO$_4$), filtered and evaporated. The residue was purified on silica gel (10% ethyl acetate in hexane) to give 52 g of 5-bromo-3,3-dimethyl-2,3-dihydro-benzofuran (98%). $^1$H NMR (300 MHz; CDCl$_3$): δ 1.32 (s, 6 H), 4.23 (s, 2 H), 6.67 (d, J=8.1 Hz, 1 H), 7.19 (m, 2 H).

g. 4-bromo-2-(2-chloro-1,1-dimethyl-ethyl)-1-methoxy-benzene.

Sulfuric acid (2 mL, 0.033 mol) was added dropwise under argon to 4-bromoanisole (14.6 mL, 0.117 mol). The mixture was warmed to 40–43° C. (warm water bath) and 3-chloro-2-methyl propene was added dropwise in 4 equal portions over 2 hrs. After 2 hrs at 40–43° C. the solution was diluted with dichloromethane and washed successively with water, saturated aqueous NaHCO$_3$, water and brine, dried (Mg$_2$SO$_4$), filtered and evaporated. The residue was crystallized from hexanes to give 14.1 g of 4-bromo-2-(2-chloro-1,1-dimethyl-ethyl)-1-methoxy-benzene. The mother liquor was further purified on silica gel (10% ethyl acetate in hexane) to afford additional 4.8 g of product. 58% yield. $^1$H NMR (300 MHz; CDCl$_3$): δ 1.43 (s, 6 H), 3.82 (s, 3 H), 3.93 (s, 2 H), 6.75 (dd, J=2.4 Hz and 7.2 Hz, 1 H), 7.32 (m, 2 H).

Example 22

3,3-Dimethyl-7-[5-(3-substituted-2,4-dioxo-thiazolidin-5-ylidenemethyl)-2-trifluoromethoxy-phenyl]-2,3-dihydro-benzofuran-5-carboxylic acid dimethylamides can be prepared in a similar manner to example 19 using 7-[5-formyl-2-trifluoromethoxy-phenyl]-3,3-dimethyl-2,3-dihydro-benzofuran-5-carboxylic acid dimethylamide as an intermediate.

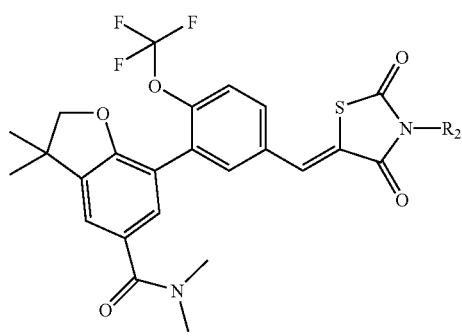

The intermediate 7-[5-formyl-2-trifluoromethoxy-phenyl]-3,3-dimethyl-2,3-dihydro-benzofuran-5-carboxylic acid dimethylamide was prepared as followed:

a. 7-[5-formyl-2-trifluoromethoxy-phenyl]-3,3-dimethyl-2,3-dihydro-benzofuran-5-carboxylic acid dimethylamide.

To a solution of 7-bromo-3,3-dimethyl-2,3-dihydro-benzofuran-5-carboxylic acid dimethylamide (437 mg, 1.46 mmol) in dioxane (4 mL), were added under argon, triethylamine (0.82 mL, 5.86 mmol), Pd(OAc)$_2$ (16 mg, 0.07 mmol), 2-(dicyclohexylphosphino)biphenyl (103 mg, 0.29 mmol) and pinacolborane (0.64 mL, 4.40 mmol) dropwise. The mixture was heated at 80° C. under argon for 2 hrs then cooled to room temperature. Water (0.5 mL) was added dropwise, then Ba(OH)$_2$.8H$_2$O (1.38 g, 4.40 mmol) followed by 3-bromo-4-trifluoromethoxy benzaldehyde (473 mg, 1.76 mmol) dissolved in dioxane (1.2 mL). The mixture was refluxed for 4 hours then cooled to room temperature, diluted with ethyl acetate and filtered over celite. The solution was further washed with water and brine, dried over anhydrous magnesium sulfate, filtered and evaporated. The residue was purified on silica gel (5% methanol in dichloromethane) to give 264 mg of 7-[5-formyl-2-trifluoromethoxy-phenyl]-3,3-dimethyl-2,3-dihydro-benzofuran-5-carboxylic acid dimethylamide (containing 50% of 3,3-dimethyl-2,3-dihydro-benzofuran-5-carboxylic acid dimethylamide as determined by $^1$H NMR) use as this in the next step.

b. 7-bromo-3,3-dimethyl-2,3-dihydro-benzofuran-5-carboxylic acid dimethylamide.

Prepared in a similar manner to example 3a using 7-bromo-3,3-dimethyl-2,3-dihydro-benzofuran-5-carboxylic acid (example 3b) and dimethylamine hydrochloride. 45% yield. $^1$H NMR (300 MHz; CDCl$_3$): 1.36 (s, 6 H), 3.05 (br s, 6 H), 4.37 (s, 2 H), 7.16 (d, J=1.5 Hz, 1 H), 7.38 (d, J=1.5 Hz, 1 H).

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A compound having the formula

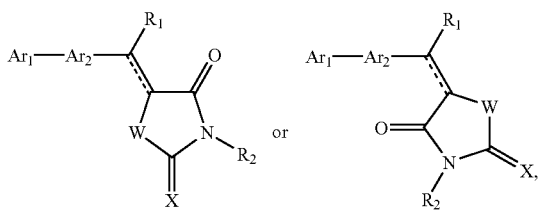

wherein, a) "- - -" is absent or present;

b) Ar$_1$ has from six to 25 carbon atoms and has the formula

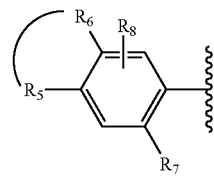

wherein R$_5$ and R$_6$ together with the aromatic ring form a five, six, or seven membered non-aromatic cycloalkyl or substituted cycloalkyl ring which can optionally comprise one, or two ring heteroatoms independently selected from O, S, N, and NR$_N$, wherein R$_N$ is hydrogen, hydroxyl, halogen, amino, or an organic radical comprising one to twelve carbon atoms; and wherein R$_7$ and R$_8$ are independently selected from hydrogen, alkyl, substituted alkyl, amino, mono-substituted amino, or di-substituted amino;

c) Ar$_2$ comprises from four to twenty carbon atoms and an aryl ring or heteroaryl ring, and d) R$_1$ is hydrogen or a substituted or unsubstituted organic radical comprising from one to four carbon atoms;

e) R$_2$ is a substituted or unsubstituted organic radical comprising one to twelve carbon atoms;

f) W is —S—, —O— or —N—R$_3$ wherein R$_3$ is hydrogen, or a substituted or unsubstituted radical comprising from one to 12 carbon atoms; and g) X is O or S;

or a pharmaceutically acceptable salt thereof.

2. The compound of claim 1 wherein R$_2$ is an alkyl or substituted alkyl group.

3. The compound of claim 1 wherein R$_2$ is a —CH$_2$CO$_2$H group.

4. The compound of claim 1 wherein "- - -" is present.

5. The compound of claim 1 wherein R$_7$ is hydrogen.

6. The compound of claim 1 wherein R$_8$ is hydrogen.

7. The compound of claim 1 wherein R$_1$ is hydrogen.

8. The compound of claim 1 wherein W is —S—.

9. The compound of claim 1 wherein X is —O—, or —S—.

10. The compound of claim 1 wherein X is —O—.

11. The compound of claim 1 wherein W is —S—, and X is —O—.

12. The compound of claim 1 wherein W is —S—, and X is —S—.

13. The compound of claim 1 wherein R$_5$ and R$_6$ together with the aromatic ring form a cycloalkyl ring, or a substituted cyloalkyl ring having from one to four substituent groups independently selected from inorganic radicals selected from halogen, cyano, nitro, hydroxyl, amino, and from organic radicals comprising from one to four carbon atoms independently selected from alkyl, substituted alkyl, acyloxy, alkoxy, substituted alkoxy, acyl, mono-substituted amino, di-substituted amino, carboxy, carboalkoxy, alkylcarboxamide, or dialkylcarboxamide groups.

14. The compound of claim 13 wherein the cycloalkyl ring, or substituted cyloalkyl ring together with the aromatic ring comprise a fused ring having the structures

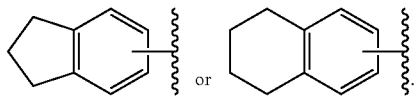

15. The compound of claim 13 wherein the cycloalkyl ring, or substituted cyloalkyl ring comprises 1, 2 or 3 heteroatoms or heteroatomic groups that can include O, S, SO, $SO_2$ and N, wherein N can be optionally further substituted with hydrogen, alkyl or substituted alkyl groups comprising one to ten carbon atoms.

16. The compound of claim 1 wherein $Ar_1$ has the structure

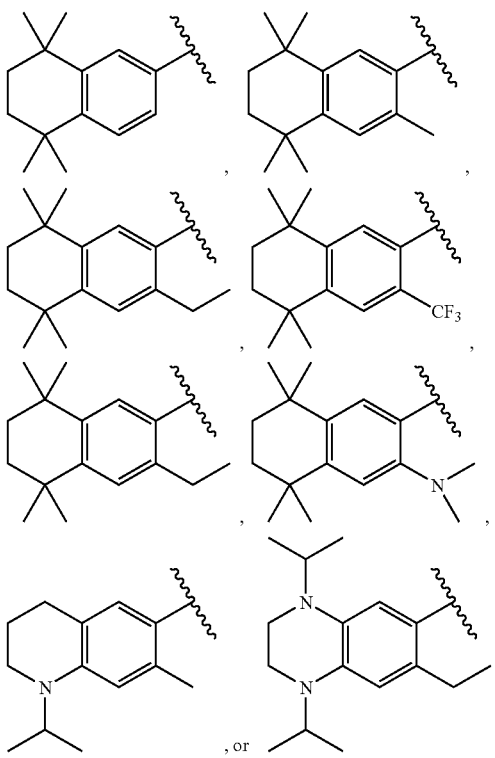

17. The compound of claim 1 wherein $R_5$ and $R_6$ together with the aromatic ring form a cycloalkenyl ring, or a substituted cyloalkenyl ring having from one to four substituent groups independently selected from inorganic radicals selected from halogen, cyano, nitro, hydroxyl, amino, and from organic radicals comprising from one to four carbon atoms independently selected from alkyl, substituted alkyl, acyloxy, alkoxy, substituted alkoxy, acyl, mono-substituted amino, di-substituted amino, carboxy, carboalkoxy, alkylcarboxamide, or dialkylcarboxamide groups.

18. The compound of claim 1 wherein $Ar_2$ is an aryl ring optionally substituted with one, two, or three substituent groups independently selected from inorganic radicals selected from halogen, cyano, nitro, hydroxyl, amino, and from organic radicals comprising from one to four carbon atoms independently selected from alkyl, substituted alkyl, haloalkyl, haloalkoxy, acyloxy, alkoxy, substituted alkoxy, acyl, mono-substituted amino, di-substituted amino, carboxy, carboalkoxy, alkylcarboxamide, or dialkylcarboxamide groups.

19. The compound of claim 1 wherein $Ar_2$ has the structure

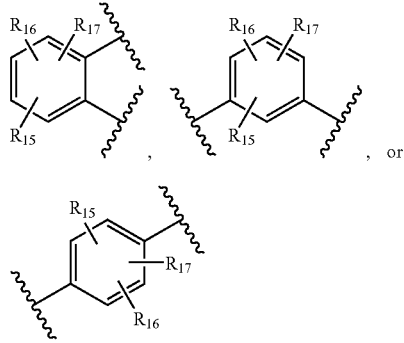

wherein $R_{15}$, $R_{16}$, and $R_{17}$ are independently selected from inorganic radicals selected from halogen, cyano, nitro, hydroxyl, amino, and from organic radicals comprising from one to four carbon atoms independently selected from alkyl, substituted alkyl, acyloxy, alkoxy, substituted alkoxy, acyl, mono-substituted amino, di-substituted amino, carboxy, carboalkoxy, alkylcarboxamide, or dialkylcarboxamide radicals.

20. The compound of claim 1 wherein $Ar_2$ has the structure

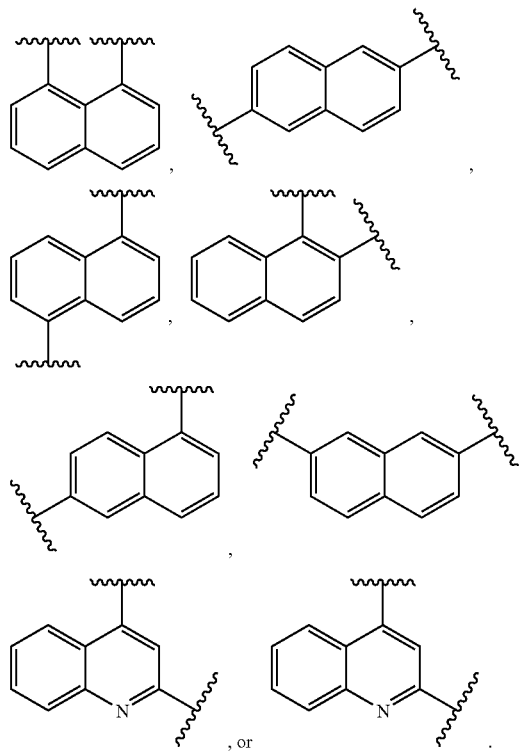

21. The compound of claim 1 wherein Ar$_2$ has the structure

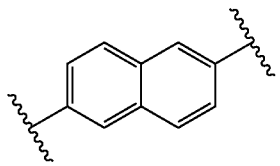

22. The compound of claim 1 wherein Ar$_2$ is a heteroaryl ring optionally substituted with one, two, or three substituent groups independently selected from inorganic radicals selected from halogen, cyano, nitro, hydroxyl, amino, and from organic radicals comprising from one to four carbon atoms independently selected from alkyl, substituted alkyl, acyloxy, alkoxy, substituted alkoxy, acyl, mono-substituted amino, di-substituted amino, carboxy, carboalkoxy, alkylcarboxamide, or dialkylcarboxamide radicals.

23. The compound of claim 1 wherein Ar$_2$ has the structure

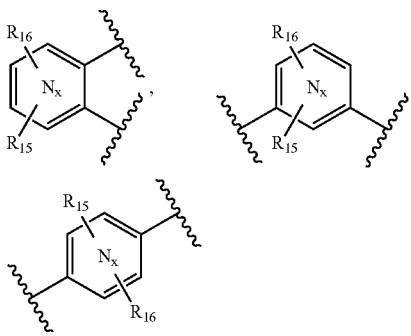

wherein x is one or two, and R$_{15}$, and R$_{16}$ are independently selected from inorganic radicals selected from halogen, cyano, nitro, hydroxyl, amino, and from organic radicals comprising from one to four carbon atoms independently selected from alkyl, substituted alkyl, acyloxy, alkoxy, substituted alkoxy, acyl, mono-substituted amino, di-substituted amino, carboxy, carboalkoxy, alkylcarboxamide, or dialkylcarboxamide groups.

24. The compound of claim 23 wherein Ar$_2$ comprises a heteroaryl ring having the structure

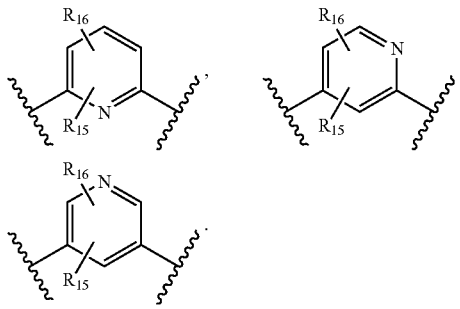

25. The compound of claim 23 wherein Ar$_2$ comprises a heteroaryl ring having the structure

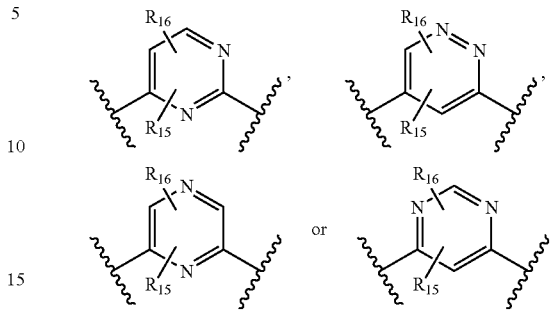

26. The compound of claim 1 that when applied at a concentration of about 10 uM to a human tumor cell line culture for leukemia, lung cancer, colon cancer, CNS cancer, melanoma, ovarian cancer, renal cancer, prostate cancer, breast cancer, or pancreatic cancer is effective to inhibit cell growth of the tumor cells by 50% or more.

27. A compound of claim 1 that is effective, when applied at a concentration of about 10 uM, to inhibit by at least 25% the adipocite differentiation induced by rosiglitazone which is applied at a concentration of 0.1 uM.

28. A compound having the formula

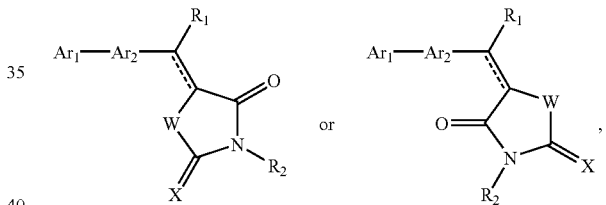

wherein,
a) "- - -" is absent or present;
b) Ar$_1$ has the formula

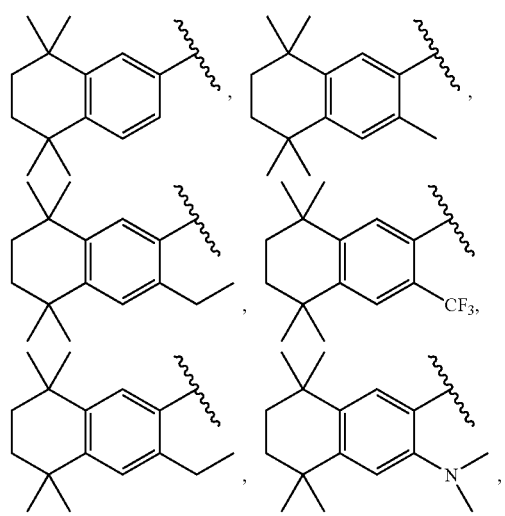

-continued

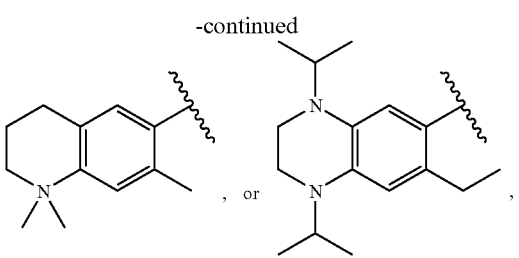

Ar$_2$ has the formula

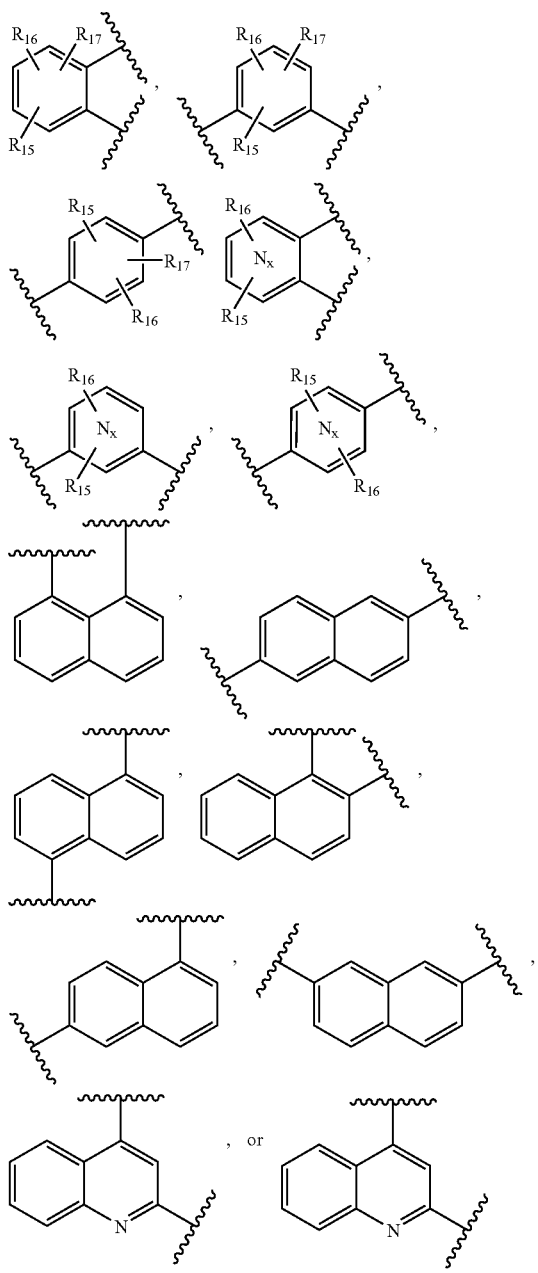

wherein x is one or two, and R$_{15}$, R$_{16}$ and R$_{17}$ are independently selected from hydrogen, halogen, cyano, nitro, hydroxyl, amino, or an organic radicals comprising one to four carbon atoms selected from an alkyl, substituted alkyl, haloalkyl, haloalkoxy, alkoxy, substituted alkoxy, mono-substituted amino, di-substituted amino having from one to four carbon atoms.

c) R$_1$ is hydrogen, or an alkyl or substituted alkyl group having one to four carbon atoms;

d) R$_2$ is a an alkyl or substituted alkyl group having one to four carbon atoms, e) W is —S—; and f) X is O or S;

or a pharmaceutically acceptable salt thereof.

29. The compound of claim 28 wherein "- - -" is present.

30. The compound of claim 28 wherein R$_1$ is hydrogen.

31. The compound of claim 28 wherein Ar$_2$ has the formula

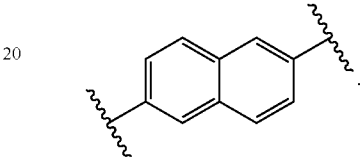

32. A compound present as:
{5-[4-Methoxy-3-(3,5,5,8,8-pentamethyl-5,6,7,8-tetrahydro-naphthalen-2-yl)-benzylidene]-4-oxo-2-thioxo-thiazolidin-3-yl}-acetic acid;

{5-[4-Trifluoromethoxy-3-(3,5,5,8,8-pentamethyl-5,6,7,8-tetrahydro-naphthalen-2-yl)-benzylidene]-4-oxo-2-thioxo-thiazolidin-3-yl}-acetic acid;

{5-[6-Methoxy-5-(3,5,5,8,8-pentamethyl-5,6,7,8-tetrahydro-naphthalen-2-yl)-pyridin-3-yl methylene]-4-oxo-2-thioxo-thiazolidin-3-yl}-acetic acid;

3-Ethyl-{5-[4-Trifluoromethoxy-3-(3,5,5,8,8-pentamethyl-5,6,7,8-tetrahydro-naphthalen-2-yl)-benzylidene]-2-thioxo-thiazolidin-4-one;

3-Methyl-{5-[4-Trifluoromethoxy-3-(3,5,5,8,8-pentamethyl-5,6,7,8-tetrahydro-naphthalen-2-yl)-benzylidene]-2-thioxo-thiazolidin-4-one;

5-[4-Methoxy-3-(3,5,5,8,8-pentamethyl-5,6,7,8-tetrahydro-naphthalen-2-yl)-benzylidene]-3-(2-pyridin-2-yl-ethyl)-thiazolidine-2,4-dione;

{5-[6-(3-Dimethylamino-5,5,8,8-tetramethyl-5,6,7,8-tetrahydro-naphthalen-2-yl)-naphthalen-2-yl methylene]-4-oxo-2-thioxo-thiazolidin-3-yl}-acetic acid;

{5-[5-Phenyl-3-methoxy-2-(3-methoxy-5,5,8,8-tetramethyl-5,6,7,8-tetrahydro-naphthalen-2-yl)-benzylidene]-4-oxo-2-thioxo-thiazolidin-3-yl}-acetic acid;

{5-[3-Methoxy-2-(3,5,5,8,8-pentamethyl-5,6,7,8-tetrahydro-naphthalen-2-yl)-benzylidene]-4-oxo-2-thioxo-thiazolidin-3-yl}-acetic acid;

{5-[4-Dimethylamino-3-(3-dimethylamino-5,5,8,8-tetramethyl-5,6,7,8-tetrahydro-naphthalen-2-yl)-benzylidene]4-oxo-2-thioxo-thiazolidin-3-yl}-acetic acid; or {5-[(3-t-Butyl-4-methoxyphenyl)-6-ethoxy-benzylidene]-4-oxo-2-thioxo-thiazolidin-3-yl}-acetic acid; or a pharmaceutically acceptable salt thereof.

33. A pharmaceutical composition for administration in mammals comprising one or more pharmaceutically acceptable carriers and one or more compounds of claim 1 in an amount effective for modulating lipid metabolism or adipocyte differentiation.

34. A method of modulating lipid metabolism or adipocyte differentiation comprising administering to a mammal diagnosed as needing such modulation the pharmaceutical composition of claim 33.

35. A method of treating hypercholesterimia comprising administering to a mammal diagnosed as needing such treatment the pharmaceutical composition of claim 33.

36. The method of claim 35, wherein the compound is applied in an amount effective to decrease serum cholesterol levels by at least about 5%.

37. A method of treating dyslipidemia comprising administering to a mammal diagnosed as needing such treatment the pharmaceutical composition of claim 33 in an amount effective to decrease serum cholesterol levels.

38. The method of claim 37, wherein the compound is applied in an amount effective to decrease serum cholestrol levels by at least about by at least 5%.

39. A pharmaceutical composition comprising one or more pharmaceutically acceptable carriers and one or more compounds of claim 1.

40. A method of treatment for a disease of uncontrolled cellular proliferation selected from the group consisting of lung cancer, brest cancer, prostate cancer, or pancreatic cancer comprising administering to a mammal diagnosed as having lung cancer, breast cancer, prostate cancer, or pancreatic cancer the pharmaceutical composition of claim 39 in an amount that is effective to treat the disease of uncontrolled cellular proliferation selected from the group consisting of lung cancer, breast cancer, prostate cancer, or pancreatic cancer.

41. The method of claim 40, wherein the disease of uncontrolled cellular proliferation is lung cancer.

42. The method of claim 40, wherein the disease of uncontrolled cellular proliferation is prostate cancer.

43. The method of claim 40, wherein the disease of uncontrolled cellular proliferation is pancreatic cancer.

44. A method of claim 40, wherein the disease of uncontrolled cellular proliferation is breast cancer.

45. The method of claim 40 wherein the mammal is a human.

* * * * *